United States Patent
Carr, Jr. et al.

(10) Patent No.: US 9,498,318 B2
(45) Date of Patent: *Nov. 22, 2016

(54) REMOVABLE EMBOLUS BLOOD CLOT FILTER

(71) Applicant: C. R. Bard, Inc., Murray Hill, NJ (US)

(72) Inventors: Robert M. Carr, Jr., Paradise Valley, AZ (US); Andrzej J. Chanduszko, Chandler, AZ (US); John D. McDermott, Coto de Caza, AZ (US); John A. Kaufman, Lake Oswego, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/070,873

(22) Filed: Nov. 4, 2013

(65) Prior Publication Data
US 2014/0058437 A1    Feb. 27, 2014

Related U.S. Application Data

(63) Continuation of application No. 13/170,054, filed on Jun. 27, 2011, now Pat. No. 8,574,261, which is a continuation of application No. 11/429,975, filed on May 9, 2006, now Pat. No. 7,967,838.

(60) Provisional application No. 60/680,601, filed on May 12, 2005.

(51) Int. Cl.
*A61F 2/01* (2006.01)

(52) U.S. Cl.
CPC ............... *A61F 2/01* (2013.01); *A61B 90/39* (2016.02); *A61F 2002/016* (2013.01);
(Continued)

(58) Field of Classification Search
CPC .................................. A61M 29/00; A61F 2/01
USPC ................. 606/200, 198, 194, 191, 127, 113
See application file for complete search history.

(56) References Cited

U.S. PATENT DOCUMENTS

| 893,055 A | 7/1908 | Conner |
| 2,212,334 A | 8/1940 | Wallerich |

(Continued)

FOREIGN PATENT DOCUMENTS

| CA | 2173118 A1 | 4/1995 |
| CA | 2648325 A1 | 4/2000 |

(Continued)

OTHER PUBLICATIONS

"Staff Development Special, Get the Edge on Deep Vein Thrombosis", Nursing Management, Jan. 2004, pp. 21-29.
(Continued)

*Primary Examiner* — Vy Bui
(74) *Attorney, Agent, or Firm* — C. R. Bard Intellectual Property; Buchalter Nemer

(57) ABSTRACT

A removable blood clot filter includes a number of locator members and anchor members disposed radially and extending angularly downward from a hub. The locator members include a number of linear portions having distinct axes configured to place a tip portion approximately parallel to the walls of a blood vessel when implanted and to apply sufficient force to the vessel walls to position the filter near the vessel centerline. The anchor members each include a hook configured to penetrate the vessel wall to prevent longitudinal movement due to blood flow. The hooks may have a cross section sized to allow for a larger radius of curvature under strain so that the filter can be removed without damaging the vessel wall.

15 Claims, 15 Drawing Sheets

(52) U.S. Cl.
CPC . *A61F 2220/0016* (2013.01); *A61F 2230/005* (2013.01); *A61F 2230/008* (2013.01); *A61F 2250/0037* (2013.01); *A61F 2250/0039* (2013.01); *A61F 2250/0067* (2013.01); *A61F 2250/0098* (2013.01)

(56) References Cited

U.S. PATENT DOCUMENTS

| | | |
|---|---|---|
| 2,767,703 A | 10/1956 | Nieburgs |
| 3,334,629 A | 8/1967 | Cohn |
| 3,472,230 A | 10/1969 | Fogarty |
| 3,540,431 A | 11/1970 | Mobin-Uddia |
| 3,579,798 A | 5/1971 | Henderson |
| 3,620,212 A | 11/1971 | Fannon, Jr. et al. |
| 3,657,744 A | 4/1972 | Ersek |
| 3,875,928 A | 4/1975 | Angelchik |
| 3,885,562 A | 5/1975 | Lampkin |
| 3,952,747 A | 4/1976 | Kimmell, Jr. |
| 4,000,739 A | 1/1977 | Stevens |
| 4,041,931 A | 8/1977 | Elliott et al. |
| 4,198,960 A | 4/1980 | Utsugi et al. |
| 4,256,132 A | 3/1981 | Gunter |
| 4,282,876 A | 8/1981 | Flynn |
| 4,283,447 A | 8/1981 | Flynn |
| 4,317,446 A | 3/1982 | Ambrosio et al. |
| 4,334,536 A | 6/1982 | Pfleger |
| 4,343,048 A | 8/1982 | Ross et al. |
| 4,411,655 A | 10/1983 | Schreck |
| 4,419,095 A | 12/1983 | Nebergall et al. |
| 4,425,908 A | 1/1984 | Simon |
| 4,494,531 A | 1/1985 | Gianturco |
| 4,562,596 A | 1/1986 | Kornberg |
| 4,572,186 A | 2/1986 | Gould et al. |
| 4,586,501 A | 5/1986 | Claracq et al. |
| 4,588,399 A | 5/1986 | Nebergall et al. |
| 4,590,938 A | 5/1986 | Segura et al. |
| 4,611,594 A | 9/1986 | Grayhack et al. |
| 4,619,246 A | 10/1986 | Molgaard-Nielsen et al. |
| 4,643,184 A | 2/1987 | Mobin-Uddin |
| 4,655,219 A | 4/1987 | Petruzzi |
| 4,655,771 A | 4/1987 | Wallsten |
| 4,657,024 A | 4/1987 | Coneys |
| 4,665,906 A | 5/1987 | Jervis |
| 4,680,573 A | 7/1987 | Ciordinik et al. |
| 4,688,553 A | 8/1987 | Metals et al. |
| 4,710,192 A | 12/1987 | Liotta et al. |
| 4,722,344 A | 2/1988 | Cambron et al. |
| 4,727,873 A | 3/1988 | Mobin-Uddin |
| 4,735,616 A | 4/1988 | Eibl et al. |
| 4,781,177 A | 11/1988 | Lebigot et al. |
| 4,793,348 A | 12/1988 | Palmaz |
| 4,798,591 A | 1/1989 | Okada et al. |
| 4,817,600 A | 4/1989 | Herms et al. |
| 4,832,055 A | 5/1989 | Palestrant |
| 4,838,879 A | 6/1989 | Tanabe et al. |
| 4,857,062 A | 8/1989 | Russell |
| 4,863,442 A | 9/1989 | DeMello et al. |
| 4,873,978 A | 10/1989 | Ginsburg |
| 4,886,506 A | 12/1989 | Lovgren et al. |
| 4,888,506 A | 12/1989 | Umehara et al. |
| 4,898,591 A | 2/1990 | Jang et al. |
| 4,915,695 A | 4/1990 | Koobs |
| 4,922,905 A | 5/1990 | Strecker et al. |
| 4,943,297 A | 7/1990 | Saveliev et al. |
| 4,950,227 A | 8/1990 | Savin et al. |
| 4,957,501 A | 9/1990 | Lahille et al. |
| 4,969,891 A | 11/1990 | Gewertz |
| 4,990,151 A | 2/1991 | Wallsten |
| 4,990,156 A | 2/1991 | Lefebvre |
| 5,045,072 A | 9/1991 | Castillo et al. |
| 5,059,205 A | 10/1991 | El-Nounou et al. |
| 5,067,957 A | 11/1991 | Jervis |
| 5,074,867 A | 12/1991 | Wilk |
| 5,098,440 A | 3/1992 | Hillstead |
| 5,108,418 A | 4/1992 | Lefebvre et al. |
| 5,114,408 A | 5/1992 | Fleischhaker et al. |
| 5,120,308 A | 6/1992 | Hess |
| 5,133,733 A | 7/1992 | Rasmussen et al. |
| 5,147,378 A | 9/1992 | Markham |
| 5,147,379 A | 9/1992 | Sabbaghian et al. |
| 5,152,777 A | 10/1992 | Goldberg et al. |
| 5,171,232 A | 12/1992 | Castillo et al. |
| 5,188,616 A | 2/1993 | Nadal et al. |
| 5,190,546 A | 3/1993 | Jervis |
| 5,203,776 A | 4/1993 | Durfee |
| 5,219,358 A | 6/1993 | Bendel et al. |
| 5,234,416 A | 8/1993 | Macaulay et al. |
| 5,234,458 A | 8/1993 | Metais et al. |
| 5,242,462 A | 9/1993 | El-Nounou et al. |
| 5,292,331 A | 3/1994 | Boneau |
| 5,300,086 A | 4/1994 | Gory et al. |
| 5,304,156 A | 4/1994 | Sylvanowicz et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,358,493 A | 10/1994 | Schweich, Jr. et al. |
| 5,370,657 A | 12/1994 | Irie |
| 5,375,612 A | 12/1994 | Cottenceau et al. |
| 5,383,887 A | 1/1995 | Nadal et al. |
| 5,397,310 A | 3/1995 | Chu et al. |
| 5,397,355 A | 3/1995 | Marin et al. |
| 5,413,586 A | 5/1995 | Dibie et al. |
| 5,421,832 A | 6/1995 | Lefebvre et al. |
| 5,423,851 A | 6/1995 | Samuels |
| 5,443,497 A | 8/1995 | Venbrux |
| 5,464,408 A | 11/1995 | Duc |
| 5,485,667 A | 1/1996 | Kleshinski |
| 5,514,154 A | 5/1996 | Lau et al. |
| 5,531,788 A | 7/1996 | Dibie et al. |
| 5,545,151 A | 8/1996 | O'Connor et al. |
| 5,545,210 A | 8/1996 | Hess et al. |
| 5,549,576 A | 8/1996 | Patterson et al. |
| 5,549,626 A | 8/1996 | Miller et al. |
| 5,554,181 A | 9/1996 | Das |
| 5,558,652 A | 9/1996 | Henke |
| 5,562,698 A | 10/1996 | Parker |
| 5,562,728 A | 10/1996 | Lazarus et al. |
| 5,591,197 A | 1/1997 | Orth et al. |
| 5,593,417 A | 1/1997 | Rhodes |
| 5,593,434 A | 1/1997 | Williams |
| 5,597,378 A | 1/1997 | Jervis |
| 5,601,568 A | 2/1997 | Chevillon et al. |
| 5,601,595 A | 2/1997 | Smith |
| 5,603,721 A | 2/1997 | Lau et al. |
| 5,624,508 A | 4/1997 | Flomenblit et al. |
| 5,626,605 A | 5/1997 | Irie et al. |
| 5,630,822 A | 5/1997 | Hermann et al. |
| 5,634,942 A | 6/1997 | Chevillon et al. |
| 5,641,364 A | 6/1997 | Golberg et al. |
| 5,649,906 A | 7/1997 | Gory et al. |
| 5,669,879 A | 9/1997 | Duer et al. |
| 5,669,933 A | 9/1997 | Simon et al. |
| 5,672,153 A | 9/1997 | Lax et al. |
| 5,672,158 A | 9/1997 | Okada et al. |
| 5,674,278 A | 10/1997 | Boneau |
| 5,681,347 A | 10/1997 | Cathcart et al. |
| 5,683,411 A | 11/1997 | Kavteladze et al. |
| 5,695,518 A | 12/1997 | Laerum et al. |
| 5,695,519 A | 12/1997 | Summers et al. |
| 5,702,370 A | 12/1997 | Sylvanowicz et al. |
| 5,704,910 A | 1/1998 | Humes |
| 5,704,926 A | 1/1998 | Sutton |
| 5,704,928 A | 1/1998 | Morita et al. |
| 5,707,376 A | 1/1998 | Kavteladze et al. |
| 5,709,704 A | 1/1998 | Nott et al. |
| 5,720,762 A | 2/1998 | Bass |
| 5,720,764 A | 2/1998 | Naderlinger |
| 5,720,776 A | 2/1998 | Chuter et al. |
| 5,725,550 A | 3/1998 | Nadal et al. |
| 5,746,767 A | 5/1998 | Smith |
| 5,755,790 A | 5/1998 | Chevillon et al. |
| 5,759,192 A | 6/1998 | Saunders |
| 5,769,816 A | 6/1998 | Barbut et al. |

(56) References Cited

U.S. PATENT DOCUMENTS

| | | |
|---|---|---|
| 5,775,790 A | 7/1998 | Ohtake |
| 5,776,162 A | 7/1998 | Kleshinski |
| 5,776,181 A | 7/1998 | Lee et al. |
| 5,780,807 A | 7/1998 | Saunders |
| 5,800,457 A | 9/1998 | Gelbfish |
| 5,800,515 A | 9/1998 | Nadal et al. |
| 5,800,526 A | 9/1998 | Anderson et al. |
| 5,830,222 A | 11/1998 | Makower |
| 5,836,968 A | 11/1998 | Simon et al. |
| 5,836,969 A | 11/1998 | Kim et al. |
| 5,843,164 A | 12/1998 | Frantzen et al. |
| 5,843,167 A | 12/1998 | Dwyer et al. |
| 5,853,420 A | 12/1998 | Chevillon et al. |
| 5,879,382 A | 3/1999 | Boneau |
| 5,891,190 A | 4/1999 | Boneau |
| 5,893,867 A | 4/1999 | Bagaoisan et al. |
| 5,893,869 A | 4/1999 | Barnhart et al. |
| 5,896,869 A | 4/1999 | Maniscalco et al. |
| 5,897,497 A | 4/1999 | Fernandez |
| 5,911,704 A | 6/1999 | Humes |
| 5,919,224 A | 7/1999 | Thompson et al. |
| 5,928,261 A | 7/1999 | Ruiz |
| 5,935,162 A | 8/1999 | Dang |
| 5,938,683 A | 8/1999 | Lefebvre |
| 5,944,728 A | 8/1999 | Bates |
| 5,951,585 A | 9/1999 | Cathcart et al. |
| 5,954,741 A | 9/1999 | Fox et al. |
| 5,961,546 A | 10/1999 | Robinson et al. |
| 5,968,052 A | 10/1999 | Sullivan, III et al. |
| 5,968,071 A | 10/1999 | Chevillon et al. |
| 5,972,019 A | 10/1999 | Engelson et al. |
| 5,976,172 A | 11/1999 | Homsma et al. |
| 5,984,947 A | 11/1999 | Smith |
| 5,989,266 A | 11/1999 | Foster |
| 6,001,118 A | 12/1999 | Daniel et al. |
| 6,004,347 A | 12/1999 | McNamara et al. |
| 6,007,558 A | 12/1999 | Ravenscroft et al. |
| 6,013,093 A | 1/2000 | Nott et al. |
| 6,036,723 A | 3/2000 | Anidjar et al. |
| 6,051,015 A | 4/2000 | Maahs |
| 6,059,814 A | 5/2000 | Ladd |
| 6,059,825 A | 5/2000 | Hobbs et al. |
| 6,066,158 A | 5/2000 | Engelson et al. |
| 6,068,638 A | 5/2000 | Makower |
| 6,068,645 A | 5/2000 | Tu |
| 6,071,292 A | 6/2000 | Makower et al. |
| 6,071,307 A | 6/2000 | Rhee et al. |
| 6,077,297 A | 6/2000 | Robinson et al. |
| 6,077,880 A | 6/2000 | Castillo et al. |
| 6,080,178 A | 6/2000 | Meglin |
| 6,099,534 A | 8/2000 | Bates et al. |
| 6,099,549 A | 8/2000 | Bosma et al. |
| 6,102,932 A | 8/2000 | Kurz |
| 6,113,608 A | 9/2000 | Monroe et al. |
| 6,126,645 A | 10/2000 | Thompson |
| 6,126,673 A | 10/2000 | Kim et al. |
| 6,131,266 A | 10/2000 | Saunders |
| 6,132,388 A | 10/2000 | Fleming et al. |
| 6,146,404 A | 11/2000 | Kim et al. |
| 6,156,055 A | 12/2000 | Ravenscroft |
| 6,159,225 A | 12/2000 | Makower |
| 6,162,357 A | 12/2000 | Pakki et al. |
| 6,165,179 A | 12/2000 | Cathcart et al. |
| 6,165,200 A | 12/2000 | Tsugita et al. |
| 6,171,297 B1 | 1/2001 | Pedersen et al. |
| 6,190,353 B1 | 2/2001 | Makower et al. |
| 6,193,739 B1 | 2/2001 | Chevillon et al. |
| 6,193,748 B1 | 2/2001 | Thompson et al. |
| 6,206,888 B1 | 3/2001 | Bicek et al. |
| 6,214,025 B1 | 4/2001 | Thistle et al. |
| 6,217,600 B1 | 4/2001 | DiMatteo |
| 6,228,052 B1 | 5/2001 | Pohndorf |
| 6,231,581 B1 | 5/2001 | Shank et al. |
| 6,231,587 B1 | 5/2001 | Makower |
| 6,231,588 B1 | 5/2001 | Zadno-Azizi |
| 6,231,589 B1 | 5/2001 | Wessman et al. |
| 6,235,045 B1 | 5/2001 | Barbut et al. |
| 6,241,738 B1 | 6/2001 | Dereume |
| 6,241,746 B1 | 6/2001 | Bosma et al. |
| 6,245,012 B1 | 6/2001 | Kleshinski |
| 6,245,099 B1 | 6/2001 | Edwin et al. |
| 6,251,122 B1 | 6/2001 | Tsukernik |
| 6,254,609 B1 | 7/2001 | Vrba et al. |
| 6,254,633 B1 | 7/2001 | Pinchuk et al. |
| 6,258,026 B1 * | 7/2001 | Ravenscroft et al. ......... 600/200 |
| 6,258,101 B1 | 7/2001 | Blake, III |
| 6,264,664 B1 | 7/2001 | Avellanet |
| 6,264,671 B1 | 7/2001 | Stack et al. |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,280,451 B1 | 8/2001 | Bates et al. |
| 6,280,459 B1 | 8/2001 | Doble |
| 6,282,222 B1 | 8/2001 | Wieser et al. |
| 6,283,983 B1 | 9/2001 | Makower et al. |
| 6,287,317 B1 | 9/2001 | Makower et al. |
| 6,287,332 B1 | 9/2001 | Bolz et al. |
| 6,287,335 B1 | 9/2001 | Drasler et al. |
| 6,290,710 B1 | 9/2001 | Cryer et al. |
| 6,302,875 B1 | 10/2001 | Makower et al. |
| 6,302,891 B1 | 10/2001 | Nadal et al. |
| 6,306,163 B1 | 10/2001 | Fitz |
| 6,322,541 B2 | 11/2001 | West et al. |
| 6,325,790 B1 | 12/2001 | Trotta |
| 6,328,755 B1 | 12/2001 | Marshall |
| 6,331,183 B1 | 12/2001 | Suon |
| 6,336,934 B1 | 1/2002 | Gilson et al. |
| 6,342,062 B1 | 1/2002 | Suon et al. |
| 6,342,063 B1 | 1/2002 | DeVries et al. |
| 6,344,053 B1 | 2/2002 | Boneau |
| 6,355,056 B1 | 3/2002 | Pinheiro |
| 6,361,546 B1 | 3/2002 | Khosravi |
| 6,383,193 B1 | 5/2002 | Cathcart et al. |
| 6,383,195 B1 | 5/2002 | Richard |
| 6,383,206 B1 | 5/2002 | Gillick et al. |
| 6,391,045 B1 | 5/2002 | Kim et al. |
| 6,402,771 B1 | 6/2002 | Palmer et al. |
| 6,416,530 B2 | 7/2002 | DeVries et al. |
| 6,425,909 B1 | 7/2002 | Dieck et al. |
| 6,428,559 B1 | 8/2002 | Johnson |
| 6,432,127 B1 | 8/2002 | Kim et al. |
| 6,436,120 B1 | 8/2002 | Meglin |
| 6,436,121 B1 | 8/2002 | Blom |
| 6,440,077 B1 | 8/2002 | Jung et al. |
| 6,442,413 B1 | 8/2002 | Silver |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,458,145 B1 | 10/2002 | Ravenscroft et al. |
| 6,468,290 B1 * | 10/2002 | Weldon ............ A61F 2/01 606/127 |
| 6,482,222 B1 | 11/2002 | Bruckheimer et al. |
| 6,485,500 B1 | 11/2002 | Kokish et al. |
| 6,485,501 B1 | 11/2002 | Green |
| 6,485,502 B2 | 11/2002 | Don Michael et al. |
| 6,488,662 B2 | 12/2002 | Sirimanne |
| 6,497,709 B1 | 12/2002 | Heath |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,503 B1 | 1/2003 | Burkett et al. |
| 6,517,559 B1 | 2/2003 | O'Connell |
| 6,517,573 B1 | 2/2003 | Pollock et al. |
| 6,527,962 B1 | 3/2003 | Nadal |
| 6,537,294 B1 | 3/2003 | Boyle et al. |
| 6,537,295 B2 | 3/2003 | Petersen |
| 6,537,296 B2 | 3/2003 | Levinson et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,280 B1 | 4/2003 | Daniel et al. |
| 6,551,303 B1 | 4/2003 | Van Tassel et al. |
| 6,551,340 B1 | 4/2003 | Konya et al. |

(56) References Cited

U.S. PATENT DOCUMENTS

| | | |
|---|---|---|
| 6,551,342 B1 | 4/2003 | Shen et al. |
| 6,558,404 B2 | 5/2003 | Tsukernik |
| 6,558,405 B1 | 5/2003 | McInnes |
| 6,558,406 B2 | 5/2003 | Okada et al. |
| 6,563,080 B2 | 5/2003 | Shapovalov et al. |
| 6,569,183 B1 | 5/2003 | Kim et al. |
| 6,569,184 B2 | 5/2003 | Huter |
| 6,572,605 B1 | 6/2003 | Humes |
| 6,575,997 B1 | 6/2003 | Palmer et al. |
| 6,579,314 B1 | 6/2003 | Lombardi et al. |
| 6,582,447 B1 | 6/2003 | Patel et al. |
| 6,589,266 B2 | 7/2003 | Whitcher et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,602,226 B1 | 8/2003 | Smith et al. |
| 6,602,273 B2 | 8/2003 | Marshall |
| 6,607,553 B1 | 8/2003 | Healy et al. |
| 6,610,077 B1 | 8/2003 | Hancock et al. |
| 6,616,680 B1 | 9/2003 | Thielen |
| 6,616,681 B2 | 9/2003 | Hanson et al. |
| 6,620,183 B2 | 9/2003 | DiMatteo |
| 6,623,450 B1 | 9/2003 | Dutta |
| 6,623,506 B2 | 9/2003 | McGuckin, Jr. et al. |
| 6,629,993 B2 | 10/2003 | Voinov et al. |
| 6,638,293 B1 | 10/2003 | Makower et al. |
| 6,640,077 B2 | 10/2003 | Suzuki et al. |
| 6,641,590 B1 | 11/2003 | Palmer et al. |
| 6,645,152 B1 | 11/2003 | Jung et al. |
| 6,645,224 B2 | 11/2003 | Gilson et al. |
| 6,652,555 B1 | 11/2003 | VanTassel et al. |
| 6,652,556 B1 | 11/2003 | VanTassel et al. |
| 6,652,558 B2 | 11/2003 | Patel et al. |
| 6,652,692 B2 | 11/2003 | Pedersen et al. |
| 6,656,203 B2 | 12/2003 | Roth et al. |
| 6,660,021 B1 | 12/2003 | Palmer et al. |
| 6,660,031 B2 | 12/2003 | Tran et al. |
| 6,663,650 B2 | 12/2003 | Sepetka et al. |
| 6,679,902 B1 | 1/2004 | Boyle et al. |
| 6,679,903 B2 | 1/2004 | Kurz |
| 6,682,540 B1 | 1/2004 | Sancoff et al. |
| 6,685,722 B1 | 2/2004 | Rosenbluth et al. |
| 6,685,738 B2 | 2/2004 | Chouinard et al. |
| 6,689,150 B1 | 2/2004 | VanTassel et al. |
| 6,695,813 B1 | 2/2004 | Boyle et al. |
| 6,696,667 B1 | 2/2004 | Flanagan et al. |
| 6,702,834 B1 | 3/2004 | Boylan et al. |
| 6,702,843 B1 | 3/2004 | Brown et al. |
| 6,706,054 B2 | 3/2004 | Wessman et al. |
| 6,712,834 B2 | 3/2004 | Yassour et al. |
| 6,716,208 B2 | 4/2004 | Humes |
| 6,719,717 B1 | 4/2004 | Johnson et al. |
| 6,719,772 B2 | 4/2004 | Trask et al. |
| 6,726,621 B2 | 4/2004 | Suon et al. |
| 6,730,108 B2 | 5/2004 | Van Tassel et al. |
| 6,736,842 B2 | 5/2004 | Healy et al. |
| 6,752,819 B1 | 6/2004 | Brady et al. |
| 6,755,846 B1 | 6/2004 | Yadav |
| 6,761,732 B2 | 7/2004 | Burkett et al. |
| 6,773,448 B2 | 8/2004 | Kusleika et al. |
| 6,776,770 B1 | 8/2004 | Trerotola |
| 6,776,774 B2 | 8/2004 | Tansey, Jr. et al. |
| 6,783,538 B2 | 8/2004 | McGuckin, Jr. et al. |
| 6,792,979 B2 | 9/2004 | Konya et al. |
| 6,793,665 B2 | 9/2004 | McGuckin, Jr. et al. |
| 6,818,006 B2 | 11/2004 | Douk et al. |
| 6,837,898 B2 | 1/2005 | Boyle et al. |
| 6,840,950 B2 | 1/2005 | Stanford et al. |
| 6,843,798 B2 * | 1/2005 | Kusleika et al. ............. 606/200 |
| 6,849,061 B2 | 2/2005 | Wagner |
| 6,852,076 B2 | 2/2005 | Nikolic et al. |
| 6,872,217 B2 | 3/2005 | Walak et al. |
| 6,881,218 B2 | 4/2005 | Beyer et al. |
| 6,884,259 B2 | 4/2005 | Tran et al. |
| 6,887,256 B2 | 5/2005 | Gilson et al. |
| 6,972,025 B2 | 12/2005 | WasDyke |
| 6,989,021 B2 | 1/2006 | Bosma et al. |
| 6,991,641 B2 | 1/2006 | Diaz et al. |
| 6,991,642 B2 | 1/2006 | Petersen |
| 7,001,424 B2 | 2/2006 | Patel et al. |
| 7,011,094 B2 | 3/2006 | Rapacki et al. |
| 7,033,376 B2 | 4/2006 | Tsukernik |
| 7,041,117 B2 | 5/2006 | Suon et al. |
| 7,052,511 B2 | 5/2006 | Weldon et al. |
| 7,056,286 B2 | 6/2006 | Ravenscroft et al. |
| 7,147,649 B2 | 12/2006 | Thomas |
| 7,163,550 B2 | 1/2007 | Boismier |
| 7,179,275 B2 | 2/2007 | McGuckin, Jr. et al. |
| 7,220,257 B1 | 5/2007 | Lafontaine |
| 7,232,462 B2 | 6/2007 | Schaeffer |
| 7,261,731 B2 | 8/2007 | Patel et al. |
| 7,279,000 B2 | 10/2007 | Cartier et al. |
| 7,303,571 B2 | 12/2007 | Makower et al. |
| 7,314,477 B1 | 1/2008 | Ravenscroft et al. |
| 7,323,003 B2 | 1/2008 | Lowe |
| 7,331,992 B2 | 2/2008 | Randall et al. |
| 7,338,512 B2 | 3/2008 | McGuckin, Jr. et al. |
| 7,534,251 B2 | 5/2009 | WasDyke |
| 7,544,202 B2 | 6/2009 | Cartier et al. |
| 7,572,289 B2 | 8/2009 | Sisken et al. |
| 7,582,100 B2 | 9/2009 | Johnson et al. |
| 7,625,390 B2 | 12/2009 | Hendriksen et al. |
| 7,699,867 B2 * | 4/2010 | Hendriksen et al. ......... 606/200 |
| 7,704,266 B2 | 4/2010 | Thinnes, Jr. et al. |
| 7,704,267 B2 | 4/2010 | Tessmer |
| 7,722,635 B2 | 5/2010 | Beyer et al. |
| 7,722,638 B2 | 5/2010 | Deyette, Jr. et al. |
| 7,736,383 B2 | 6/2010 | Bressler et al. |
| 7,736,384 B2 | 6/2010 | Bressler et al. |
| 7,749,244 B2 | 7/2010 | Brucheimer et al. |
| 7,749,246 B2 | 7/2010 | McGuckin, Jr. et al. |
| 7,766,932 B2 | 8/2010 | Melzer et al. |
| 7,794,472 B2 | 9/2010 | Eidenschink et al. |
| 7,799,049 B2 | 9/2010 | Ostrovsky et al. |
| 7,887,580 B2 | 2/2011 | Randall et al. |
| 7,967,838 B2 | 6/2011 | Chanduszko et al. |
| 7,972,353 B2 | 7/2011 | Hendriksen et al. |
| 7,993,362 B2 | 8/2011 | Lowe et al. |
| 8,029,529 B1 | 10/2011 | Chanduszko |
| 8,062,327 B2 | 11/2011 | Chanduszko et al. |
| 8,075,606 B2 | 12/2011 | Dorn |
| 8,133,251 B2 | 3/2012 | Ravenscroft et al. |
| 8,241,350 B2 | 8/2012 | Randall et al. |
| 8,267,954 B2 | 9/2012 | Decant, Jr. et al. |
| 8,333,785 B2 | 12/2012 | Chanduszko et al. |
| 8,372,109 B2 | 2/2013 | Tessmer |
| 8,430,903 B2 | 4/2013 | Chanduszko et al. |
| 8,574,261 B2 | 11/2013 | Carr et al. |
| 2001/0000799 A1 | 5/2001 | Wessman et al. |
| 2001/0001317 A1 | 5/2001 | Duerig et al. |
| 2001/0016770 A1 | 8/2001 | Allen et al. |
| 2001/0020175 A1 | 9/2001 | Yassour et al. |
| 2001/0023358 A1 | 9/2001 | Tsukernik |
| 2001/0027339 A1 | 10/2001 | Boatman et al. |
| 2001/0039431 A1 | 11/2001 | DeVries et al. |
| 2002/0002401 A1 | 1/2002 | McGuckin et al. |
| 2002/0004060 A1 | 1/2002 | Heublein et al. |
| 2002/0010350 A1 | 1/2002 | Tatsumi et al. |
| 2002/0022853 A1 | 2/2002 | Swanson et al. |
| 2002/0032461 A1 | 3/2002 | Marshall |
| 2002/0038097 A1 | 3/2002 | Corvi et al. |
| 2002/0042626 A1 | 4/2002 | Hanson et al. |
| 2002/0045918 A1 | 4/2002 | Suon et al. |
| 2002/0052626 A1 | 5/2002 | Gilson et al. |
| 2002/0055767 A1 | 5/2002 | Forde et al. |
| 2002/0072764 A1 | 6/2002 | Sepetka et al. |
| 2002/0116024 A1 | 8/2002 | Goldberg et al. |
| 2002/0123720 A1 | 9/2002 | Kusleika et al. |
| 2002/0138097 A1 | 9/2002 | Ostrovsky et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004540 A1 | 1/2003 | Linder et al. |

(56) References Cited

U.S. PATENT DOCUMENTS

| | | |
|---|---|---|
| 2003/0004541 A1 | 1/2003 | Linder et al. |
| 2003/0004946 A1 | 1/2003 | VanDenAvond et al. |
| 2003/0028241 A1 | 2/2003 | Stinson |
| 2003/0055812 A1 | 3/2003 | Williams et al. |
| 2003/0071285 A1 | 4/2003 | Tsukernik |
| 2003/0093106 A1 | 5/2003 | Brady et al. |
| 2003/0093110 A1 | 5/2003 | Vale |
| 2003/0097145 A1 | 5/2003 | Goldberg et al. |
| 2003/0109824 A1 | 6/2003 | Anderson et al. |
| 2003/0109897 A1 | 6/2003 | Walak et al. |
| 2003/0114735 A1 | 6/2003 | Silver et al. |
| 2003/0114880 A1 | 6/2003 | Hansen et al. |
| 2003/0130680 A1 | 7/2003 | Russell |
| 2003/0139765 A1 | 7/2003 | Patel et al. |
| 2003/0153945 A1 | 8/2003 | Patel et al. |
| 2003/0158595 A1 | 8/2003 | Randall et al. |
| 2003/0163159 A1 | 8/2003 | Patel et al. |
| 2003/0171771 A1 | 9/2003 | Anderson et al. |
| 2003/0176888 A1 | 9/2003 | O'Connell |
| 2003/0176912 A1 | 9/2003 | Chuter et al. |
| 2003/0191516 A1 | 10/2003 | Weldon et al. |
| 2003/0195554 A1 | 10/2003 | Shen et al. |
| 2003/0195556 A1 | 10/2003 | Stack et al. |
| 2003/0199918 A1 | 10/2003 | Patel et al. |
| 2003/0208227 A1 | 11/2003 | Thomas |
| 2003/0208229 A1 | 11/2003 | Kletschka |
| 2003/0208253 A1 | 11/2003 | Beyer et al. |
| 2003/0220683 A1 | 11/2003 | Minasian et al. |
| 2004/0006364 A1 | 1/2004 | Ladd |
| 2004/0006369 A1 | 1/2004 | DiMatteo |
| 2004/0059373 A1 | 3/2004 | Shapiro et al. |
| 2004/0068288 A1 | 4/2004 | Palmer |
| 2004/0073252 A1 | 4/2004 | Goldberg et al. |
| 2004/0082966 A1 | 4/2004 | WasDyke |
| 2004/0087999 A1 | 5/2004 | Bosma et al. |
| 2004/0088000 A1 | 5/2004 | Muller |
| 2004/0088001 A1 | 5/2004 | Bosma et al. |
| 2004/0088002 A1 | 5/2004 | Boyle et al. |
| 2004/0093015 A1 | 5/2004 | Ogle |
| 2004/0093064 A1 | 5/2004 | Bosma |
| 2004/0116959 A1 | 6/2004 | McGuckin et al. |
| 2004/0138693 A1 | 7/2004 | Eskuri et al. |
| 2004/0153110 A1 | 8/2004 | Kurz et al. |
| 2004/0153118 A1 | 8/2004 | Clubb et al. |
| 2004/0153119 A1 | 8/2004 | Kusleika et al. |
| 2004/0158267 A1 | 8/2004 | Sancoff et al. |
| 2004/0158273 A1 | 8/2004 | Weaver et al. |
| 2004/0158274 A1 | 8/2004 | WasDyke |
| 2004/0167568 A1 | 8/2004 | Boyle et al. |
| 2004/0172042 A1 | 9/2004 | Suon et al. |
| 2004/0176672 A1 | 9/2004 | Silver et al. |
| 2004/0186510 A1 | 9/2004 | Weaver |
| 2004/0186512 A1 | 9/2004 | Bruckheimer et al. |
| 2004/0193209 A1 | 9/2004 | Pavenik et al. |
| 2004/0199240 A1 | 10/2004 | Dorn |
| 2004/0199270 A1 | 10/2004 | Wang et al. |
| 2004/0220610 A1 | 11/2004 | Kreidler et al. |
| 2004/0220611 A1 | 11/2004 | Ogle |
| 2004/0230220 A1 | 11/2004 | Osborne |
| 2004/0243173 A1 | 12/2004 | Inoue |
| 2005/0004596 A1 | 1/2005 | McGuckin et al. |
| 2005/0015111 A1 | 1/2005 | McGuckin et al. |
| 2005/0019370 A1 | 1/2005 | Humes |
| 2005/0021075 A1 | 1/2005 | Bonnette et al. |
| 2005/0021076 A1 | 1/2005 | Mazzocchi et al. |
| 2005/0021152 A1 | 1/2005 | Ogle et al. |
| 2005/0027314 A1 | 2/2005 | WasDyke |
| 2005/0027345 A1 | 2/2005 | Horan et al. |
| 2005/0049609 A1 | 3/2005 | Gunderson et al. |
| 2005/0055045 A1 | 3/2005 | DeVries et al. |
| 2005/0055046 A1 | 3/2005 | McGuckin et al. |
| 2005/0059990 A1 | 3/2005 | Ayala et al. |
| 2005/0059993 A1 | 3/2005 | Ramzipoor et al. |
| 2005/0065591 A1 | 3/2005 | Moberg et al. |
| 2005/0070794 A1 | 3/2005 | Deal et al. |
| 2005/0070821 A1 | 3/2005 | Deal et al. |
| 2005/0080447 A1 | 4/2005 | McGuckin et al. |
| 2005/0080449 A1 | 4/2005 | Mulder |
| 2005/0085847 A1 | 4/2005 | Galdonik et al. |
| 2005/0090858 A1 | 4/2005 | Pavlovic |
| 2005/0101982 A1 | 5/2005 | Ravenscroft et al. |
| 2005/0107822 A1 | 5/2005 | WasDyke |
| 2005/0115111 A1 | 6/2005 | Yamashita et al. |
| 2005/0131451 A1 | 6/2005 | Kleshinski et al. |
| 2005/0131452 A1 | 6/2005 | Walak et al. |
| 2005/0159771 A1 | 7/2005 | Petersen |
| 2005/0165441 A1 | 7/2005 | McGuckin et al. |
| 2005/0165442 A1 | 7/2005 | Thinnes et al. |
| 2005/0171473 A1 | 8/2005 | Gerdts et al. |
| 2005/0182439 A1 | 8/2005 | Lowe |
| 2005/0222604 A1 | 10/2005 | Schaeffer |
| 2005/0234503 A1 | 10/2005 | Ravenscroft et al. |
| 2005/0251199 A1 | 11/2005 | Osborne et al. |
| 2005/0267512 A1 | 12/2005 | Osborne et al. |
| 2005/0267513 A1 | 12/2005 | Osborne et al. |
| 2005/0267514 A1 | 12/2005 | Osborne et al. |
| 2005/0267515 A1 | 12/2005 | Oliva et al. |
| 2005/0288703 A1 | 12/2005 | Beyer et al. |
| 2005/0288704 A1 | 12/2005 | Cartier et al. |
| 2006/0004402 A1 | 1/2006 | Voeller et al. |
| 2006/0015137 A1 | 1/2006 | WasDyke et al. |
| 2006/0016299 A1 | 1/2006 | Chen |
| 2006/0030875 A1 | 2/2006 | Tessmer |
| 2006/0036279 A1 | 2/2006 | Eidenschink et al. |
| 2006/0041271 A1 | 2/2006 | Bosma et al. |
| 2006/0047300 A1 | 3/2006 | Eidenschink |
| 2006/0047341 A1 | 3/2006 | Trieu |
| 2006/0069405 A1 | 3/2006 | Schaeffer et al. |
| 2006/0069406 A1 | 3/2006 | Hendriksen et al. |
| 2006/0079928 A1 | 4/2006 | Cartier et al. |
| 2006/0079930 A1 | 4/2006 | McGuckin et al. |
| 2006/0095068 A1 | 5/2006 | WasDyke et al. |
| 2006/0106417 A1* | 5/2006 | Tessmer ............. A61F 2/01 606/200 |
| 2006/0155320 A1 | 7/2006 | Bressler et al. |
| 2006/0157889 A1 | 7/2006 | Chen |
| 2006/0203769 A1 | 9/2006 | Saholt et al. |
| 2006/0206138 A1 | 9/2006 | Eidenschink |
| 2006/0259067 A1 | 11/2006 | Welch et al. |
| 2006/0259068 A1 | 11/2006 | Eidenschink |
| 2007/0005095 A1 | 1/2007 | Osborne et al. |
| 2007/0005104 A1 | 1/2007 | Kusleika et al. |
| 2007/0005105 A1 | 1/2007 | Kusleika et al. |
| 2007/0039432 A1 | 2/2007 | Cutler |
| 2007/0043419 A1 | 2/2007 | Nikolchev et al. |
| 2007/0060944 A1 | 3/2007 | Boldenow et al. |
| 2007/0088381 A1 | 4/2007 | McGuckin et al. |
| 2007/0100372 A1 | 5/2007 | Schaeffer |
| 2007/0112373 A1 | 5/2007 | Carr et al. |
| 2007/0167974 A1 | 7/2007 | Cully et al. |
| 2007/0173885 A1 | 7/2007 | Cartier et al. |
| 2007/0185524 A1 | 8/2007 | Diaz et al. |
| 2007/0191878 A1 | 8/2007 | Segner et al. |
| 2007/0191880 A1 | 8/2007 | Cartier et al. |
| 2007/0198050 A1 | 8/2007 | Ravenscroft et al. |
| 2007/0213685 A1 | 9/2007 | Bressler et al. |
| 2007/0219530 A1 | 9/2007 | Schaeffer |
| 2007/0250106 A1 | 10/2007 | Kim |
| 2008/0014078 A1 | 1/2008 | Suciu et al. |
| 2008/0033479 A1 | 2/2008 | Silver |
| 2008/0039891 A1 | 2/2008 | McGuckin et al. |
| 2008/0091230 A1 | 4/2008 | Lowe |
| 2008/0097518 A1 | 4/2008 | Thinnes et al. |
| 2008/0103582 A1 | 5/2008 | Randall et al. |
| 2008/0119867 A1 | 5/2008 | Delaney |
| 2008/0183206 A1 | 7/2008 | Batiste |
| 2008/0221609 A1 | 9/2008 | McGuckin et al. |
| 2008/0221656 A1 | 9/2008 | Hartley et al. |
| 2008/0255605 A1 | 10/2008 | Weidman |
| 2008/0262506 A1 | 10/2008 | Griffin et al. |
| 2008/0275486 A1 | 11/2008 | Dwyer et al. |
| 2008/0275488 A1 | 11/2008 | Fleming |
| 2008/0294189 A1 | 11/2008 | Moll et al. |
| 2008/0300621 A1 | 12/2008 | Hopkins et al. |

(56) References Cited

U.S. PATENT DOCUMENTS

| | | |
|---|---|---|
| 2009/0005803 A1 | 1/2009 | Batiste |
| 2009/0043332 A1 | 2/2009 | Sullivan et al. |
| 2009/0069840 A2 | 3/2009 | Hallisey |
| 2009/0105747 A1 | 4/2009 | Chanduszko et al. |
| 2009/0131970 A1 | 5/2009 | Chanduszko et al. |
| 2009/0163926 A1 | 6/2009 | Sos |
| 2009/0192543 A1 | 7/2009 | WasDyke |
| 2009/0198270 A1 | 8/2009 | McGuckin, Jr. et al. |
| 2009/0264915 A1 | 10/2009 | WasDyke |
| 2009/0299403 A1 | 12/2009 | Chanduszko et al. |
| 2009/0299404 A1 | 12/2009 | Chanduszko et al. |
| 2009/0318951 A1 | 12/2009 | Kashkarov et al. |
| 2010/0030253 A1 | 2/2010 | Harris et al. |
| 2010/0030254 A1 | 2/2010 | Chanduszko et al. |
| 2010/0049239 A1 | 2/2010 | McGuckin, Jr. et al. |
| 2010/0063535 A1 | 3/2010 | Bressler et al. |
| 2010/0076545 A1 | 3/2010 | Kleshinski et al. |
| 2010/0160956 A1 | 6/2010 | Hendriksen et al. |
| 2010/0174310 A1 | 7/2010 | Tessmer |
| 2010/0222772 A1 | 9/2010 | Kleshinski et al. |
| 2010/0256669 A1 | 10/2010 | Harris et al. |
| 2010/0312269 A1 | 12/2010 | McGuckin, Jr. et al. |
| 2010/0318115 A1 | 12/2010 | Chanduszko et al. |
| 2011/0118823 A1 | 5/2011 | Randall et al. |
| 2011/0257677 A1 | 10/2011 | Carr, Jr. et al. |
| 2012/0065663 A1 | 3/2012 | Chanduszko et al. |
| 2012/0184985 A1 | 7/2012 | Ravenscroft et al. |
| 2013/0006295 A1 | 1/2013 | Chanduszko et al. |
| 2013/0085523 A1 | 4/2013 | Tessmer |
| 2013/0096607 A1 | 4/2013 | Chanduszko et al. |

FOREIGN PATENT DOCUMENTS

| | | |
|---|---|---|
| DE | 3633527 A1 | 4/1988 |
| EP | 0145166 A2 | 6/1985 |
| EP | 0188927 A2 | 7/1986 |
| EP | 0712614 A1 | 5/1996 |
| EP | 1042996 A2 | 10/2000 |
| EP | 1092401 A1 | 4/2001 |
| EP | 1336393 A2 | 8/2003 |
| EP | 1475110 A1 | 11/2004 |
| FR | 2567405 A1 | 1/1986 |
| FR | 2718950 A1 | 10/1995 |
| FR | 2781143 A1 | 1/2000 |
| FR | 2791551 A1 | 10/2000 |
| JP | 08257031 | 10/1996 |
| JP | 2002525183 A | 8/2002 |
| JP | 2003521970 A | 7/2003 |
| JP | 2005503199 A | 2/2005 |
| JP | 4851522 B2 | 1/2012 |
| JP | 5102201 | 10/2012 |
| SV | 07A000025 | 4/1997 |
| WO | 9509567 A1 | 4/1995 |
| WO | 9534339 A1 | 12/1995 |
| WO | 9612448 A1 | 5/1996 |
| WO | 9617634 A2 | 6/1996 |
| WO | 9729794 A1 | 8/1997 |
| WO | 9802203 A1 | 1/1998 |
| WO | 9823322 A1 | 6/1998 |
| WO | 9925252 A1 | 5/1999 |
| WO | 0012011 A1 | 3/2000 |
| WO | 0018467 A1 | 4/2000 |
| WO | 0056390 A1 | 9/2000 |
| WO | 0076422 A1 | 12/2000 |
| WO | 0117457 A1 | 3/2001 |
| WO | 0204060 A1 | 1/2002 |
| WO | 02055125 A2 | 7/2002 |
| WO | 02102436 A2 | 12/2002 |
| WO | 03003927 A1 | 1/2003 |
| WO | 03004074 A3 | 1/2003 |
| WO | 03073961 A1 | 9/2003 |
| WO | 2004012587 A2 | 2/2004 |
| WO | 2004049973 A1 | 6/2004 |
| WO | 2004098459 A1 | 11/2004 |
| WO | 2004098460 A1 | 11/2004 |
| WO | 2005009214 A2 | 2/2005 |
| WO | 2005072645 A1 | 8/2005 |
| WO | 2005102212 A1 | 11/2005 |
| WO | 2005102437 A2 | 11/2005 |
| WO | 2005102439 A2 | 11/2005 |
| WO | 2006036457 A2 | 4/2006 |
| WO | 2006055174 A2 | 5/2006 |
| WO | 2006124405 A2 | 11/2006 |
| WO | 2007021340 A1 | 2/2007 |
| WO | 2007079410 A2 | 7/2007 |
| WO | 2007100619 A2 | 9/2007 |
| WO | 2007106378 A2 | 9/2007 |
| WO | 2007143602 A2 | 12/2007 |
| WO | 2008051294 A2 | 5/2008 |
| WO | 2008076970 A1 | 6/2008 |
| WO | 2008077067 A2 | 6/2008 |
| WO | 2008109131 A2 | 9/2008 |

OTHER PUBLICATIONS

AbuRahma, A.F. et al., "Endovascular Caval Interruption in Pregnant Patients With Deep Vein Thrombosis of the Lower Extremity", Journal of Vascular Surgery, 2001, 33:375-378.

AbuRahma, A.F. et al., "Management of Deep Vein Thrombosis of the Lower Extremity in Pregnancy: A Challenging Dilemma", The American Surgeon, Feb. 1999, vol. 65, No. 2, pp. 164-167A.

AbuRahma, F. et al., "Etiology of Peripheral Arterial Thromboembolism in Young Patients", The American Journal of Surgery, vol. 176, Aug. 1998, pp. 158-161.

Adams, E. et al., "Retrievable Inferior Vena Cava Filter for Thrombolic Disease in Pregnancy", British Journal of Obstetrics and Gynaecology, Sep. 1998, vol. 105, pp. 1039-1042.

Adye, B. A., "Case Report: Errant Percutaneous Greenfield Filter Placement Into the Retroperitoneum", Journal of Vascular Surgery, Jul. 1990, vol. 12, No. 1.

Ahearn, G.S. et al., "Massive Pulmonary Embolism During Pregnancy Successfully Treated With Recombinant Tissue Plasminogen Activator", Archives of Interal Medicine, Jun. 10, 2002, 162(11):1221-1227.

Aklog, L. et al., "Acute Pulmonary Embolectomy", Circulation, 2002, 105:1416-1419.

Alexander, J. J. et al., "Is the Increasing Use of Prophylactic Percutaneous IVC Filters Justified?", The American Journal of Surgery, Aug. 1994, vol. 168, pp. 102-106.

Allen, T.L. et al., "Retrievable Vena Cava Filters in Trauma Patients for High-Risk Prophylaxis and Prevention of Pulmonary Embolism", The American Journal of Surgery, 2005, 189:656-661.

American Gastroenterological Association Clinical Practice Committee, "Technical Review on Obesity," Sep. 2002 123:883-932.

Anderson, J.T. et al., "Bedside Noninvasive Detection of Acute Pulmonary Embolism in Critically Ill Surgical Patients", Archives of Surgery, Aug. 1999, 134(8):869-875.

Andrews, R. T. et al., "Entrapment of J-Tip Guidewires by Venatech and Stainless-Steel Greenfield Vena Cava Filters During Central Venous Catheter Placement: Percutaneous Management in Four Patients", Cardiovasc Intervent Radiol. Sep.-Oct. 1998;21(5):424-8.

Anthone, G.J. et al., The Duodenal Switch Operation for the Treatment of Morbid Obesity, Annals of Surgery, Oct. 2003, 238(4):618-628.

Arcasoy, S.M. et al., "Thrombolytic Therapy of Pulmonary Embolism", Chest, 1999, 115:1695-1707.

Arcelus, J.I. et al, "The Management and Outcome of Acute Venous Thromboembolism: A Prospective Registry Including 4011 Patients", Journal of Vascular Surgery, 2003, 38:916-922.

Arjomand, H. et al., "Right Ventricular Foreign Body: Percutaneous Transvenous Retrieval of a Greenfield Filter From the Right Ventricle", Angiology, 2003, vol. 54, No. 1, pp. 109-113.

Arnold, D.M. et al., "Missed Opportunities for Prevention of Venous Thromboembolism", Chest, 2001, 120:1964-1971.

Ascer, E. et al., "Superior Vena Caval Greenfield Filters: Indications, Techniques, and Results", Journal of Vascular Surgery, Mar. 1996, vol. 23, No. 3.

(56) References Cited

OTHER PUBLICATIONS

Asch, M. R., "Initial Experience in Humans With a New Retrievable Inferior Vena Cava Filter", Radiology, 2002, 225:835-844.
Ascher, E. et al., "Lessons Learned From a 6-Year Clinical Experience With Superior Vena Cava Greenfield Filters", Journal of Vascular Surgery, Nov. 2000, 32:881-887.
Ashley, D.W. et al., "Accurate Deployment of Vena Cava Filters: Comparison of Intravascular Ultrasound and Contrast Venography", The Journal of Trauma Injury, Infection, and Critical Care, Jun. 2001, vol. 50, No. 6, pp. 975-981.
Aswad, M. A. et al., "Early Duplex Scan Evaluation of Four Venal Interruption Devices", Journal of Vascular Surgery, 1996, 24:809-818.
Athanasoulis, C.A. et al., "Inferior Venal Caval Filters: Review of a 26-Year Single-Center Clinical Experience", Radiology, 2000, 216:54-66.
Authors' Abstract, "Abstracts of Current Literature", Journal of Vascular and Interventional Radiology, Mar. 2000, vol. 11, No. 3, pp. 401-407.
Authors' Abstract, "Abstracts of Current Literature", Journal of Vascular and Interventional Radiology, Oct. 2003, vol. 14, No. 10, pp. 1351-1357.
Authors' Abstract, "Abstracts of Current Literature," Journal of Vascular and Interventional Radiology, Oct. 2002, 13(10):1062-1068.
Authors' Abstracts, "Abstracts of Current Literature", Journal of Vascular and Interventional Radiology, Apr. 2002, vol. 13, No. 4, pp. 433-440.
Authors' Abstracts, "Abstracts of Current Literature", Journal of Vascular and Interventional Radiology, Apr. 2004, pp. 408-415.
Avery, M. et al., "Reverse Engineering of Nitinol Vena Cava Filters", Material Science 102 Semester Project, Nov. 21, 2000.
Baker, R. J., "Treatment Considerations for Inherited Thrombophilia and Pulmonary Embolus", Archives of Surgery, Feb. 2001, 136,2:237.
Balshi, J. D. et al., "Original Articles Complications of Caval Interruption by Greenfield Filter in Quadriplegics", Journal of Vascular Surgery, Apr. 1989, vol. 9, No. 4.
Barraco, R. D. et al., "Dislodgment of Inferior Vena Cava Filters During Central Line Placement: Case Report", The Journal of Trauma, Injury, Infection and Critical Care, 2000, vol. 48, No. 1, pp. 140-142.
Barreras, J. R. et al., "Recurrent Pulmonary Embolism Despite the Use of a Greenfield Filter", Clinical Nuclear, Dec. 2001, vol. 26, No. 12, pp. 1040-1041.
Barton, A. L. et al., "Caval Filter Placement for Pulmonary Embolism in a Patient With a Deep Vein Thrombosis and Primary Intracerebral Haemorrhage", Age and Ageing, Mar. 2002, 31,2:144-146.
Bass, B.L., "What's New in General Surgery: Gastrointestinal Conditions", The Journal of American College Surgeons, Dec. 2002, vol. 195, No. 6, pp. 835-854.
Becker, D. M. et al., "Inferior Vena Cava Filters", Archives of Internal Medicine, Oct. 1992, vol. 152, pp. 1985-1994.
Bendick, P.J. et al., Serial Duplex Ultrasound Examination for Deep Vein Thrombosis in Patients With Suspected Pulmonary Embolism, Journal of Fascular Surgery, Nov. 1996, vol. 24, No. 5, pp. 732-737.
Benjamin, M. E. et al., Duplex Ultrasound Insertion of Inferior Vena Cava Filters in Multitrauma Patients:, American Journal of Surgery, Aug. 1999, vol. 178, pp. 92-97.
Bessoud, B. et al., Experience at a Single Institution With Endovascular Treatment of Mechanical Complications Caused by Implanted Central Venous Access Devices in Pediatric and Adult Patients, American Journal of Roentgenology, Feb. 2003, 180:527-532.
Bevoni, L., "Management of Adult Obesity", Clinician Reviews, May 2003, 13(5):56-62.
Biertho, L. et al., "Laparoscopic Gastric Bypass Versus Laparoscopic Adjustable Gastric Banding: A Comparative Study of 1,200 Cases", Journal of the American Colloge of Surgeons, Oct. 2003, vol. 197, No. 4, pp. 536-545.
Binkert, C. A. et al., "Inferior Vena Cava Filter Removal After 317-Day Implantation", Journal of Vascular Radiology, Mar. 2005, 16:393-398.
Bjarnason, H. et al., "In Vitro Metal Fatigue Testing of Inferior Vena Cava Filters", Investigative Radiology, 1994, vol. 29, No. 9, pp. 817-821.
Blachar A. et al., "Gastrointestinal Complications of Laparoscopic Roux-en-Y Gastric Bypass Surgery in Patients Who Are Morbidly Obese: Findings on Radiography and CT", American Journal of Roentgenology, Dec. 2002, 179:1437-1442.
Blachar, A. et al., "Gastrointestinal Complications of Laparoscopic Roux-en-Y Gastric Bypass Surgery: Clinical and Imaging Findings", Radiology, 2002, 223:625-632.
Blaszyk, H. et al., "Factor V Leiden and Morbid Obesity in Fatal Postoperative Pulmonary Embolism", Archives of Surgery, Dec. 2000, 135(12):1410-1413.
Blebea J. et al., "Deep Venous Thrombosis After Percutaneous Insertion of Vena Caval Filters", Journal of Vascular Surgery, Nov. 1999, 30:821:829.
Bochenek, K. M. et al., "Right Atrial Migration and Percutaneous Retrieval of a Gunther Tulip Inferior Vena Cava Filter", Journal of Vascular Interventional Radiology, Sep. 2003, 14:1207-1209.
Bochicchio, G. V. et al., "Acute Caval Perforation by an Inferior Vena Cava Filter in a Multitrauma Patient: Hemostatic Control With a New Surgical Hemostat", The Journal of Trauma Injury, Infection and Critical Care, 2001, 51:991-993.
Stavropoulos, S. W. et al., "In Vitro Study of Guide Wire Entrapment in Currently Available Inferior Vena Cava Filters", Journal of Vascular and Interventional Radiology, 2003, 14:905-910.
Stecker, M. S. et al., "Evaluation of a Spiral Nitinol Temporary Inferior Vena Caval Filter", Academic Radiology, 2001, 8:484-493.
Stein, P. D. et al., "Deep Venous Thrombosis in a General Hospital", Chest, 2002, 122:960-962.
Stein, P. D., "Opinions Regarding the Diagnosis and Management of Venous Thromboembolic Disease", Chest, Feb. 1998, vol. 113, No. 2, pp. 499-504.
Still, J. et al., "Experience With the Insertion of Vena Caval Filters in Acutely Burned Patients", The American Surgeon, Mar. 2000, vol. 66, No. 3, pp. 277-279.
Stoneham G. W. et al., "Temporary Inferior Vena Cava Filters: In Vitro Comparison With Permanent IVC Filters", Journal of Vascular and Interventional Radiology, Sep.-Oct. 1995, vol. 6, pp. 731-736.
Stosslein, F. et al., "A Rare Complication With an Antheor Vena Cava Filter", Cardiovascular and Interventional Radiology, 1998, 21:165-167.
Stover, M. D. et al., "Prospective Comparison of Contrast-Enhanced Computed Tomography Versus Magnetic Resonance Venography in the Detection of Occult Deep Pelvic Vein Thrombosis in Patients With Pelvic and Acetabular Fractures", Journal of Orthopaedic Trauma, 2002, 16(9):613-621.
Streib, E. W. et al., "Complications of Vascular Access Procedures in Patients With Vena Cava Filters", The Journal of Trauma: Injury Infection, and Critical Care, Sep. 2000, vol. 49, No. 3, pp. 553-558.
Streiff, Michael B., "Vena Caval Filters: A Comprehensive Review", Blood, Jun. 15, 2000, vol. 95, No. 12, pp. 3669-3677.
Sue, L. P. et al., "Iliofemoral Venous Injuries: An Indication for Prophylactic Caval Filter Placement", The Journal of Trauma: Injury, Infection, and Critical Care, 1995, vol. 39, No. 4, pp. 693-695.
Sugerman, H. J. et al., "Risks and Benefits of Gastric Bypass in Morbidity Obese Patients With Severe Venous Stasis Disease", Annals of Surgery, 2001, vol. 234, No. 1, pp. 41-46.
Sultan, S. et al., "Operative and Endovascular Management of Extracranial Vertebral Artery Aneurysm in Ehlers-Danlos Syndrome: A Clinical Dilemma", Vascular and Endovascular Surgery, 2002, 36(5):389-392.
Taheri, S. A. et al., "Case Report: A Complication of the Greenfield Filter: Fracture and Distal Migration of Two Struts—A Case Report", Journal of Vascular Surgery, Jul. 1992, vol. 16, No. 1, pp. 96-99.

(56) References Cited

OTHER PUBLICATIONS

Tai, N. R. M. et al., "Modern Management of Pulmonary Embolism", British Journal of Surgery, 1999, 86:853-868.
Tardy, B. et al, "Older People Included in a Venous Thrombo-Embolism Clinical Trial: A Patients' Viewpoint", Age and Ageing, 2003, 32:149-153.
Tay, Kiang-Hiong et ai, "Repeated Gunther Tulip Inferior Vena Cava Filter Repositioning to Prolong Implantation Time", J Vasc Interv Radioi, May 2002, 13:509-512.
Taylor, Frank C. et al., "Vena Tech Vena Cava Filter: Experience and Early Follow-up", Journal of Vascular Interventional Radiology, Nov. 1991, 2:435-440.
Teitelbaum, G. P. et al., Low-Artifact Intravascular Devices: MR Imaging Evaluation, Radiology, Sep. 1988, 168:713-719.
Terhaar, Olaf Alfons et al., "Extended Interval for Retrieval of Gunther Tulip Filters", J Vascinterv Radiol, Nov. 2004,15:1257-1262.
Thery, C. et al., "Use of a New Removable Vena Cava Filter in Order to Prevent Pulmonary Embolism in Patients Submitted to Thrombolysis", European Heart Journal, 1990, vol. 11,334-341.
Thomas, J. H. et al., "Vena Caval Occlusion After Bird's Nest Filter Placement", American Journal of Surgery, Dec. 1998, vol. 176, pp. 598-600.
Thomas, L. A. et al., "Use of Greenfield Filters in Pregnant Women at Risk for Pulmonary Embolism", Southern Medical Journal, Feb. 1997, vol. 90, Issue 2.
Tillie-Leblond, I. et al., "Risk of Pulmonary Embolism After a Negative Spiral CT Angiogram in Patients With Pulmonary Disease: 1-Year Clinical Follow-Up Study", Radiology, 2002, 223:461-467.
Tola, J. C. et al., "Bedside Placement of Inferior Vena Cava Filters in the Intensive Care Unit", The American Surgeon, Sep. 1999, vol. 65, No. 9, pp. 833-838.
Tovey, C. et al., "Diagnosis, Investigation, and Management of Deep Vein Thrombosis", British Medical Journal, May 31, 2003, vol. 326, i7400, p. 1180(5), 9 pages.
Trerotola, S. O. et al., "Mechanical Thrombolysis of Venous Thrombosis in an Animal Model With Use of Temporary Caval Filtration", Journal of Vascular and Interventional Radiology, Sep. 2001, 12:1075-1085.
Trerotola, S. O. et al., "Preclinical in Vivo Testing of the Arrow-Trerotola Percutaneous Thrombolytic Device for Venous Thrombosis", Journal of Vascular and Interventional Radiology, 2001, 12:95-103.
Trujillo-Santos,J. et al., "Bed Rest or Ambulation in the Initial Treatment of Patients With Acute Deep Vein Thrombosis or Pulmonary Embolism", Chest, 2005, 127:1631-1636.
Tuna, I. C. et al., "Massive Pulmonary Embolus", Texas Heart Institute Journal, 2002, vol. 29, No. 2, pp. 144-145.
Uflacker, R., "Interventional Therapy for Pulmonary Embolism", Journal of Vascular Interventional Radiology, Feb. 2001, 12:147-164.
Urena, R. et al., "Bird's Nest Filter Migration to the Right Atrium", American Journal of Roentgenology, Oct. 2004, 183:1037-1039.
U.S. Appl. No. 09/640,865, filed Aug. 18, 2000 Advisory Action dated Apr. 19, 2007.
U.S. Appl. No. 09/640,865, filed Aug. 18, 2000 Advisory Action dated Mar. 23, 2006.
U.S. Appl. No. 09/640,865, filed Aug. 18, 2000 Final Office Action dated Jan. 16, 2007.
U.S. Appl. No. 09/640,865, filed Aug. 18, 2000 Final Office Action dated Nov. 30, 2005.
U.S. Appl. No. 09/640,865, filed Aug. 18, 2000 Non-Final Office Action dated Apr. 7, 2005.
U.S. Appl. No. 09/640,865, filed Aug. 18, 2000 Non-Final Office Action dated Aug. 8, 2006.
U.S. Appl. No. 09/640,865, filed Aug. 18, 2000 Non-Final Office Action dated Jun. 5, 2003.
U.S. Appl. No. 10/079,155, filed Feb. 20, 2002 Final Office Action dated Jan. 20, 2006.
U.S. Appl. No. 10/079,155, filed Feb. 20, 2002 Non-Final Office Action dated Jul. 13, 2004.
U.S. Appl. No. 10/079,155, filed Feb. 20, 2002 Non-Final Office Action dated Mar. 7, 2007.
U.S. Appl. No. 10/079,155, filed Feb. 20, 2002 Non-Final Office Action dated Nov. 20, 2006.
U.S. Appl. No. 10/079,155, filed Feb. 20, 2002 Non-Final Office Action dated Sep. 11, 2006.
U.S. Appl. No. 11/150,661, filed Jun. 10, 2005 Final Office Action dated May 27, 2010.
U.S. Appl. No. 11/150,661, filed Jun. 10, 2005 Non-Final Office Action dated Jul. 22, 2011.
U.S. Appl. No. 11/150,661, filed Jun. 10, 2005 Non-Final Office Action dated Nov. 5, 2009.
U.S. Appl. No. 11/334,829, filed Jan. 19, 2006 Non-Final Office Action dated Aug. 18, 2008.
U.S. Appl. No. 11/429,975, filed May 9, 2006 Non-Final Office Action dated Oct. 7, 2010.
U.S. Appl. No. 11/429,975, filed May 9, 2006 Notice of Allowance dated Feb. 18, 2011.
Wallace, M. J. et al., "Inferior Vena Caval Stent Filter", AJR, Dec. 1986, 147:1247-1250.
Wallace, M. J., "Transatrial Stent Placement for Treatment of Inferior Vena Cava Obstruction Secondary to Extension of Intracardiac Tumor Thrombus From Hepatocellular Carcinoma", Journal of Vascular Interventional Radiology, 2003, 14:1339-1343.
Wang, W. Y. et al., "Use of a Nitinol Gooseneck Snare to Open an Incompletely Expanded Over-the-Wire Stainless Steel Greenfield Filter", American Journal of Roentgenology, Feb. 1999, 172:499-500.
Watanabe, N. et al., "Images in Cardiology: Large Thrombus Entrapped in a Patent Foramen Ovale of the Atrial Septum, Which Apparently "Disappeared" Without Embolic Events", Heart, Nov. 2002, 88(5):474.
Watanabe, S. et al., "Superior Vena Caval Placement of a Temporary Filter: A Case Report", Vascular Surgery, Jan./Feb. 2001, vol. 35, Issue 1.
Watanabe, Shun-ichi et al., "Clinical Experience With Temporary Vena Cava Filters", Vascular Surgery, vol. 35, No. 4, 2001, pp. 285-291.
Weeks, S. M. et al., "Primary Gianturco Stent Placement for Inferior Vena Cava Abnormalities Following Liver Transplantation", Journal of Vascular and Interventional Radiology, Feb. 2000, 11:177-187.
Welch, H. J. et al., "Duplex Assessment of Venous Reflux and Chronic Venous Insufficiency: The Significance of Deep Venous Reflux", Journal of Vascular Surgery, 1996, 24:755-762.
Wellons, E. D. et al., "Bedside Intravascular Ultrasound-Guided Vena Cava Filter Placement", Journal of Vascular Surgery, 2003, 38:455-458.
Wells, J. L. et al., "Diagnosing Pulmonary Embolism: A Medical Masquerader", Clinician Reviews, 2001, 11 (2):66-79.
Westling, A. et al., "Incidence of Deep Venous Thrombosis in Patients Undergoing Obesity Surgery", World Journal of Surgery, 2002, 26:470-473.
White, R. H. et al., "A Population-Based Study of the Effectiveness of Inferior Vena Cava Filter Use Among Patients With Venous Thromboembolism", Archives of Internal Medicine, Jul. 10, 2000, 160(13):2033-2041.
Whitehill, T. A., "Current Vena Cava Filter Devices and Results", Seminars in Vascular Surgery, Sep. 2000, 13(3):204-212.
Wholey, M. et al., "Technique for Retrieval of a Guidewire Lodged in a Vena Cava Filter", Vascular and Endovascular Surgery, 2002, 36(5):385-387.
Wiles, C. E., Letters to Editor, Journal of Trauma, Aug. 1999, 47(2):438.
Wilson, J. T. et al., "Prophylactic Vena Cava Filter Insertion in Patients With Traumatic Spinal Cord Injury: Preliminary Results", Neurosurgery, 1994, 35:234-239.
Winchell, R. J. et al., "Risk Factors Associated With Pulmonary Embolism Despite Routine Prophylaxis: Implications for Improved Protection", The Journal of Trauma, 1994, 37(4):600-606.

(56) References Cited

OTHER PUBLICATIONS

Wittenberg, G. et al., "Long-Term Results of Vena Cava Filters: Experiences With the LGM and the Titanium Greenfield Devices", Cardiovascular and Interventional Radiology, 1998, 21:225-229.
Wittich, G. R. et al., "Anchoring a Migrating Inferior Vena Cava Stent With Use of a T-Fastener", Journal of Vascular and Interventional Radiology, 2001, 12:994-996.
Wojcik, R. et al., "Long-Term Follow-Up of Trauma Patients With a Vena Caval Filter", The Journal of Trauma: Injury, Infection, and Critical Care, Nov. 2000, 49(5):839-843.
Wojtowycz, M. M. et al., "The Bird's Nest Inferior Vena Caval Filter: Review of a Single-Center Experience", Journal of Vascular and Interventional Radiology, 1997, 8:171-179.
Woodward, E. B. et al., "Delayed Retroperitoneal Arterial Hemorrhage After Inferior Vena Cava (IVC) Filter Insertion: Case Report and Literature Review of Caval Perforations by IVC Filters", Annals of Vascular Surgery, 2002, 16:193-196.
Xian, Z. Y. et al., "Multiple Emboli and Filter Function: An in Vitro Comparison of Three Vena Cava Filters", Journal of Vascular and Interventional Radiology, 1995, 6:887-893.
Xu, X. Y. et al., "Flow Studies in Canine Artery Bifurcations Using a Numerical Simulation Method", Journal of Biochemical Engineering, Nov. 1992, 114:504-511.
Yagi, A. et al., "Pulmonary Thromboembolism Evaluating the Indication and Effect of a Vena Caval Filter With Indium-111-Platelet Scintigraphy", Circulation Journal, Jun. 2004, 68:599-601.
Yavuz, Kivilcim et al., "Retrievable of a Malpositioned Vena Cava Filter With Embolic Protection With Use of a Second Filter", Journal of Vascular Interventional Radiology, 2005, 16:531-534.
Yonezawa, K. et al., "Effectiveness of an Inferior Vena Cava Filter as a Preventive Measure Against Pulmonary Thromboembolism After Abdominal Surgery", Surgery Today, 1999, 29:821-824.
Yucel, E. Kent, "Pulmonary MR Angiography: Is It Ready Now?", Radiology, 1999, 210:301-303.
Zamora, C. A. et al., "Prophylactic Stenting of the Inferior Vena Cava Before Transcatheter Embolization of Renal Cell Carcinomas: An Alternative to Filter Placement", Journal of Endovascular Therapy, 2004, 11:84-88.
Zanchetta, M. et al., "A New Permanent and Retrievable Vena Cava Filter: Its Removal After Five Months", Italian Heart Journal, Sep. 2001, 2(9):715-716.
Zeni, P. T. et al., "Use of Rheolytic Thrombectomy in Treatment of Acute Massive Pulmonary Embolism", Journal of Vascular and Interventional Radiology, 2003, 14:1511-1515.
Zinzindohoue, F. et al., "Laparoscopic Gastric Banding: A Minimally Invasive Surgical Treatment for Morbid Obesity—Prospective Study of 500 Consecutive Patients", Annals of Surgery, 2003, 237(1):1-9.
Zwaan et al., "Clinical Experience with Temporary Vena Cava Filters" JVIR 9:594-601 (1998).
Neri, E. et al., "Protected Iliofemoral Venous Thrombectomy in a Pregnant Woman With Pulmonary Embolism and Ischemic Venous Thrombosis", Texas Heart Institute Journal, 2002, vol. 29, No. 2, pp. 130-132.
Neuerburg et al., "New Retrievable Percutaneous Vena Cava Filter: Experimental In Vitro and In Vivo Evaluation" Cardiovasc. Intervent. Radiol. 16:224-229 (1993).
Neuerburg, J.M. et al., "Percutaneous Retrieval of the Tulip Vena Cava Filter: Feasibility, Short-and long-Term Changes—An Experimental Study in Dogs", Cardiovascular and Interventionai Radiology, 2001, 24:418-423.
Neuerburg, Jorg et al., "Developments in Inferior Vena Cava Filters: A European Viewpoint", Seminars in Interventional Radiology, vol. 11, No. 4, Dec. 1994, pp. 349-357.
Nguyen, N. T. et al., "A Comparison Study of Laparoscopic Versus Open Gastric Bypass for Morbid Obesity", Journal of the American College of Surgeons, Aug. 2000, vol. 191, No. 2, pp. 149-155.
Nguyen, N. T. et al., "Comparison of Pulmonary Function and Postoperative Pain After Laparoscopic Versus Open Gastric Bypass: A Randomized Trial", Journal of Americal College of Surgeons, 2001, 192:469-477.
Nitnol Medical Technologies, Inc., Simon Nitinol Filter Instructions for Use, 1995.
Norwood, S. H. et al., "A Potentially Expanded Role for Enoxaparin in Preventing Venous Thromboembolism in High Risk Blunt Trauma Patients", Journal of the American College of Surgeons, 2001, 192:161-167.
Nunn, C. R. et al., "Cost-Effective Method for Bedside Insertion of Vena Caval Filters in Trauma Patients," The Journal of Trauma, Nov. 1997, vol. 43, No. 5, pp. 752-758.
Nutting, Charles et al., "Use of a TrapEase Device as a Temporary Caval Filter", Journal of Vascular Interventional Radiology, Aug. 2001, 12:991-993.
O'Brien, P. E. et al., "Laparoscopic Adjustable Gastric Banding in the Treatment of Morbid Obesity", Archives of Surgery, Apr. 2003, 138(4):376-382.
O'Malley, K. F. et al., "Prevention of Pulmonary Embolism After Pelvic Fracture: Rational Use of Inferior Vena Caval Filters", (Cooper Hospital/University Medical Center), Jan. 1996, vol. 40.
O'Sullivan, G. J. et al., "Endovascular Management of Iliac Vein Compression (May-Thurner) Syndrome", Journal of Vascular and Interventional Radiology, 2000, 11:823-836.
Offner, P. J. et al., "The Role of Temporary Inferior Vena Cava Filters in Critically Ill Surgical Patients", Archives of Surgery, Jun. 2003, vol. 138, pp. 591-595.
Olearchyk, A. S., "Insertion of the Inferior Vena Cava Filter Followed by Iliofemoral Venous Thrombectomy for Ischemic Venous Thrombosis", Journal of Vascular Surgery, Apr. 1987, vol. 5, No. 4, pp. 645-647.
Olin, J. W., "Pulmonary Embolism", Reviews in Cardiovascular Medicine, 2002, 3(2):S68-S75.
Oppat, W. F. et al., "Intravascular Ultrasound-Guided Vena Cava Filter Placement", Journal of Endovascular Surgery, 1999, 6:285-287.
Ornstein, D. L. et al., "Cancer, Thrombosis, and Anticoagulants", Current Opinion in Pulmonary Medicine, 2000, 6:301-308.
Ortega, M. et al., "Efficacy of Anticoagulation Post-Inferior Vena Caval Filter Placement", American Surgeon, May 1998, vol. 64, Issue 5, pp. 419-423.
Ortiz-Saracho, J. et al., "An Unusual Cause of Pulmonary Artery Thrombosis", Chest, 1998, 114:309-310.
Owings, J. T. et al., "Timing of the Occurrence of Pulmonary Embolism in Trauma Patients", Archives of Surgery, Aug. 1997, 132(8):862-867.
Padberg, F. T. et al, "Hemodynamic and Clinical Improvement After Superficial Vein Ablation in Primary Combined Venous Insufficiency With Ulceration", Journal of Vascular Surgery, 1996, 24:711-718.
Pais, S. O. et al., "Percutaneous Insertion of the Greenfield Inferior Vena Cava Filter: Experience With Ninety-Six Patients", Journal of Vascular Surgery, Oct. 1988, vol. 8. No. 4.
Palastrant et al., "Comparative in Vitro Evaluation of the Nitinol Inferior Vena Cava Filter" Radiology 145:351-355 (Nov. 1982).
Palestrant, Aubrey M. et al., "Comparative In Vitro Evaluation of the NitinolInferior Vena Cava Filter", Radiology, Nov. 1982,145:351-355.
Participants in the Vena Caval Filter Consensus Conference, "Recommended Reporting Standards for Vena Caval Filter Placement and Patient Follow-Up", Journal of Vascular and Interventional Radiology, 2003, 14: S427-S432.
Participants in the Vena Caval Filter Consensus Conference, "Recommended Reporting Standards for Vena Caval Filter Placement and Patient Follow-Up", Journal of Vascular Surgery, 1999, 30:573-579.
Partsch, H. et al., "Frequency of Pulmonary Embolism in Patients Who Have Iliofemoral Deep Vein Thrombosis and Are Treated With Once- or Twice-Daily Low-Molecular Weight Heparin", Journal of Vascular Surgery, 1996, 24:774-782.

(56) References Cited

OTHER PUBLICATIONS

Passman, M. A. et al., "Pulmonary Embolism is Associated With the Combination of Isolated Calf Vein Thrombosis and Respiratory Symptoms", Journal of Vascular Surgery, 1997, 25:39-45.

Patterson, R. B. et al., "Case Reports: Repositioning of Partially Dislodged Greenfield Filters From the Right Atrium by Use of a Tip Deflection Wire", Journal of Vascular Surgery, Jul. 1990, vol. 12, No. 1, pp. 70-72.

Patton, J. H. Jr., et al., "Prophylactic Greenfield Filters: Acute Complications and Long-Term Follow-Up", The Journal of Trauma: Injury, Infection, and Critical Care, 1996, vol. 41, No. 2, pp. 231-237.

Pavcnik, Dusan et al., "Retrievable IVC Square Stent Filter: Experimental Study", Cardiovascular Interventional Radiology, 1999,22:239-245.

PCT/US03/05385 filed Feb. 20, 2003 International Search Report dated Jun. 17, 2003.

PCT/US07/09215 filed Apr. 16, 2007 International Preliminary Report on Patentability dated Sep. 23, 2008.

PCT/US07/09215 filed Apr. 16, 2007 International Search Report dated Sep. 23, 2008.

PCT/US1999/020883 filed Sep. 23, 1999 Search Report dated Jan. 20, 2000.

PCT/US2006/017889 filed May 9, 2006 International Preliminary Report on Patentability dated Jul. 14, 2009.

PCT/US2006/017889 filed May 9, 2006 International Search Report dated Jul. 1, 2009.

PCT/US2006/017889 filed May 9, 2006 Written Opinion dated Jul. 1, 2009.

PCT/US2006/017890 filed May 9, 2006 Preliminary Report on Patentability dated Feb. 12, 2008.

PCT/US2006/017890 filed May 9, 2006 Search Report dated Nov. 2, 2006.

PCT/US2006/017890 filed May 9, 2006 Written Opinion dated Nov. 2, 2006.

PCT/US2006/044826 filed Nov. 17, 2006 International Preliminary Report on Patentability and Written Opinion dated Apr. 10, 2008.

PCT/US2006/044826 filed Nov. 17, 2006 International Search Report dated Apr. 10, 2008.

PCT/US2006/045738 filed Nov. 11, 2006 Search Report dated Oct. 9, 2007.

PCT/US2006/045738 filed Nov. 11, 2006 Written Opinion dated Oct. 9, 2007.

PCT/US2007/009186 filed Apr. 16, 2007 International Preliminary Report on Patentability and Written Opinion dated Nov. 4, 2008 and Sep. 29, 2008.

PCT/US2007/009186 filed Apr. 16, 2007 International Search Report dated Sep. 29, 2008.

PCT/US2010/043787 filed Jul. 29, 2010 Search Report dated Dec. 3, 2010.

PCT/US2010/043787 filed Jul. 29, 2010 Written Opinion dated Dec. 3, 2010.

Bovyn, G. et al., "The Tempofilter®: A Multicenter Study of a New Temporary Caval Filter Implantable for up to Six Weeks", Annals of Vascular Surgery, 1997, 11:520-528.

Bracale, G. et al., "Spontaneous Rupture of the Iliac Vein", The Journal of Cardiovascular Surgery, 1999, 40:871-875.

Brasel, K.J. et al., "Cost-Effective Prevention of Pulmonary Embolus in High-Risk Trauma Patients", The Journal of Trauma: Injury, Infection, and Critical Care, Mar. 1997, vol. 42, No. 3, pp. 456-462.

Bravo, S. M. et al., "Percutaneous Venous Interventions", Vascular Medicine, 1998, 3:61-66.

Bridges, G.G. et al., "Expedited Discharge in Trauma Patients Requiring Anticoagulation for Deep Venous Thrombosis Prophylaxis: The LEAP Program", The Journal of Trauma: Injury, Infection and Critical Care, Feb. 2003, vol. 54, No. 2, pp. 232-235.

Brolin, R.E., "Laparoscopic Verses Open Gastric Bypass to Treat Morbid Obesity", Annals of Surgery, Apr. 2004, vol. 239, No. 4, pp. 438-440.

Brountzos, E. N. et al., "A New Optional Vena Cava Filter: Retrieval at 12 Weeks in an Animal Model", Journal of Vascular and Interventional Radiology, Jun. 2003, 14:763-772.

Brown, D. R. et al., "Gadolinium, Carbon Dioxide, and Iodinated Contrast Material for Planning Inferior Vena Cava Filter Placement: a Prospective Trial", Journal of Vascular and Interventional Radiology, Aug. 2003, 14:1017-1022.

Browne, R. J. et al., "Guidewire Entrapment During Greenfield Filter Deployment", Journal of Vascular Surgery, Jan. 1998, 27:174-176.

Bruckheimer, E. et al., "In Vitro Evaluation of a Retrievable Low-Profile Nitinol Vena Cava Filter", Journal of Vascular and Interventional Radiology, Apr. 2003, 14:469-474.

Bucker, A. et al., "Real-Time MR Guidance for Inferior Vena Cava Filter Placement in an Animal Model", Journal of Vascular and Interventional Radiology, Jun. 2001, 12:753-756.

Buerger, P.M. et al., "Risk of Pulmonary Emboli in Patients With Pelvic Fractures", The American Surgeon, Aug. 1993, vol. 59, pp. 505-508.

Burbridge, B. E. et al., "Incorporation of the Gunther Temporary Inferior Vena Cava Filter Into the Caval Wall", Journal of Vascular and Interventional Radiology, Mar.-Apr. 1996, 7:289-290.

C.R. Bard Simon Nitinol Filter: for Use in the Vena Cava: Instructions for Use (1995, 1997).

CA 2648325 filed Sep. 23, 1999 Office Action dated Apr. 26, 2011.

Cahn, M. D. et al., "Long Term Follow-up of Greenfield Inferior Vena Cava Filter Placement in Children", Journal of Vascular Surgery, Nov. 2001, 34:820-825.

Cain Jr., J.E. et al., "The Morbidity of Heparin Therapy After Development of Pulmonary Embolus in Patients Undergoing Thoracolumbar or Lumbar Spinal Fusion", SPINE, vol. 20, No. 14, 1995, pp. 1600-1603.

Campbell, J. J. et al., "Aortic Pseudoaneurysm From Aortic Penetration With a Bird's Nest Vena Cava Filter", Journal of Vascular Surgery, Sep. 2003, 38:596-599.

Capella, J.F. et al., "An Assessment of Vertical Banded Gastroplasty-Roux-en-Y Gastric Bypass for the Treatment of Morbid Obesity," The American Journal of Surgery 183 (2002) 117-123.

Carabasi III, R. A. et al., "Complications Encountered With the Use of the Greenfield Filter", The American Journal of Surgery, Aug. 1987, Vo. 154, pp. 163-168.

Carlin, A. M. et al., "Prophylactic and Therapeutic Inferior Vena Cava Filters to Prevent Pulmonary Emboli in Trauma Patients", Archives of Surgery, May 2002, vol. 137, p. 521.

Carman, Teresa L. et al., Outpatient treatment of deep venous thrombosis, Chest; Nov. 1999; 116, 5; Health & Medical Complete, pp. 1492-1493.

Carter, Y. et al., "Deep Venous Thrombosis and ABO Blood Group Are Unrelated in Trauma Patients", The Journal of Trauma: Injury, Infection, and Critical Care, 2002, 52:112-116.

Castaneda, F. et al., "Catheter-Directed Thrombolysis in Deep Venous Thrombosis With Use of Reteplase: Immediate Results and Complications From a Pilot Study", Journal of Vascular and Interventional Radiology, 2002, 13:577-580.

Ceelen, W. et al., "Surgical Treatment of Severe Obesity With a Low-Pressure Adjustable Gastric Band, Experimental Data and Clinical Results in 625 Patients", Annals of Surgery, 2003, 237(1):10-16.

Chanduszko, A., "Determination of Nitinol Transition Temperatures Using a Dynamical Mechanical Analyzer", The International Conference on Shape Memory and Superelastic Technology, 2000 Conference Proceedings, 2001, pp. 375-381.

Chaturvedi, R. R. et al., "Intraoperative Apical Ventricular Septal Defect Closure Using a Modified Rashkind Double Umbrella", Heart, Oct. 1996, vol. 76, No. 4, pp. 367-369.

Chengelis, D.L. et al., "Progression of Superficial Venous Thrombosis to Deep Vein Thrombosis", Journal of Vascular Surgery, 1996, 24:745-749.

Cherian, J. et al., "Recurrent Pulmonary Embolism Despite Inferior Vena Cava Filter Placement in Patients With the Antiphospholipid Syndrome", Journal of Clinical Rheumatology, Feb. 2005, vol. 11, No. 1, pp. 56-58.

(56) References Cited

OTHER PUBLICATIONS

Cho, K. J. et al., "Evaluation of a New Percutaneous Stainless Steel Greenfield Filter", Journal of Vascular and Interventional Radiology, Mar.-Apr. 1997, 8:181-187.
Choban, P.S. et al., "The Impact of Obesity on Surgical Outcomes: A Review," Journal of the American College of Surgeons, Dec. 1997, vol. 185, pp. 593-603.
Chung, J.W. et al., "Acute Iliofemoral Deep Vein Thrombosis: Evaluation of Underlying Anatomic Abnormalities by Spiral CT Venography", Journal of Vascular and Interventional Radiology, 2004, 15:249-256.
Clarke, C.S. et al., "Puerperal Ovarian Vein Thrombosis With Extension Into the Inferior Vena Cava", The American Surgeon, Feb. 1999, vol. 65, No. 2, pp. 147-150.
Conners III, M. S et al., "Duplex Scan-Directed Placement of Inferior Vena Cava Filters: A Five-year Institutional Experience", Journal of Vascular Surgery, Feb. 2002, vol. 35, No. 2, pp. 286-291.
Consensus Conference, "Prevention of Venous Thrombosis and Pulmonary Embolism", JAMA, Aug. 8, 1986, vol. 256, No. 6, pp. 744-749.
Cook "Bird's Nest" Vena Cava Filter, Cook Incorporated, a Cook Group Company, Nov. 1982.
Cook, "Gunther Tulip Vena Cava Mreye.TM. Filter" Sales Brochure (2001).
Cooper, S.G. et al., "Distal Retraction and Inversion of the Simon Nitinol Filter During Surgical Venous Procedures: Report of Two Cases", Journal of Vascular and Interventional Radiology, 1997, 8:433-435.
Cottam, D.R. et al., "Laparoscopic Era of Operations for Morbid Obesity", Archives of Surgery, Apr. 2003, 138 (4):367-375.
Couch, G. G. et al., "An In Vitro Comparison of the Hemodynamics of Two Inferior Vena Cava Filters", Journal of Vascular Surgery, Mar. 2000, 31:539-549.
Couch, G. G. et al., "In Vitro Assessment of the Hemodynamic Effects of a Partial Occlusion in a Vena Cava Filter", Journal of Vascular Surgery, Apr. 1997, vol. 25, No. 4, pp. 663-672.
Cragg et al., "Nonsurgical Placement of Arterial Endoprostheses: A New Technique Using Nitinol Wire" Radiology 147:261-263 (Apr. 1983).
Cragg, A. et al., "A New Percutaneous Vena Cava Filter", American Journal of Roentgenology, Sep. 1983, 141:601-604.
Criado, Enrique, Letters to the Editor, Journal of the American College of Surgeons, Mar. 1996, vol. 182, pp. 279-280.
Critical Care Medicine, vol. 32, No. 12 (Suppl.), pp. A181-A188, 2004.
Crochet, D. et al., "Evaluation of the LGM Vena-Tech Infrarenal Vena Cava Filter in an Ovine Venous Thromboembolism Model", Journal of Vascular Interventional Radiology, Jun. 2001, 12:739-745.
Crochet, D. P. et al., "Long-Term Follow-Up of Vena Tech-LGM Filter: Predictors and Frequency of Caval Occlusion", Journal of Vascular Interventional Radiology, Feb. 1999, 10:137-142.
Crochet, D. P. et al., "Vena Tech-LGM Filter: Long-Term Results of a Prospective Study", Radiology, 1993, 188:857-860.
Cvoro,V. et al., "Inferior Vena Caval Filters or Anticoagulation for Patients With Haemorrhagic Stroke Complicated by Venouse Thromboembolism?", Age and Ageing, Mar. 2002, vol. 32, No. 2, Research Library, pp. 85-86.
Cynamon et al., "Percutaneous Removal of a Titanium Greenfield Filter" AJR 159:777-778 (Oct. 1992).
Linsenmaier U. et al, "Indications, Management, and Complications of Temporary Inferior Vena Cava Filters", Cardiovascular and Interventional Radiology, 1998, 21:464-469.
Lipman, J.C., "Removal of Vena Caval Filter at 224 Days", Southern Medical Journal, May 2005, vol. 98, No. 5, pp. 556-558.
Loehr, S.P. et al., "Retrieval of Entrapped Guide Wire in an IVC Filter Facilitated With Use of a Myocardial Biopsy Forceps and Snare Device", Journal of Vascular and Interventional Radiology (Letter to Editor), Sep. 2001, vol. 12, No. 9, pp. 1116-1118.

Lopez-Beret, P. et al., "Systematic Study of Occult Pulmonary Thromboembolism in Patients With Deep Venous Thrombosis", Journal of Vascular Surgery, 2001, 33:515-521.
Lorch, H. et al., "Current Practice of Temporary Vena Cava Filter Insertion: A Multicenter Registry", Journal of Vascular and Interventional Radiology, 2001, 11:83-88.
Lorch, H. et al., "In Vitro Studies of Temporary Vena Cava Filters", Cardiovascular and Interventional Radiology, 1998, 21:146-150.
Lorch, H. et al., "Temporary Vena Cava Filters and Ultrahigh Streptokinase Thrombolysis Therapy: A Clinical Study", Cardiovascular Interventional Radiology, 2000, 23:273-278.
Lujan, J. A. et al., "Laparoscopic Versus Open Gastric Bypass in the Treatment of Morbid Obesity", Annals of Surgery, Apr. 2004, vol. 239, No. 4, pp. 433-437.
Lund, G. et al., "A New Vena Caval Filter for Percutaneous Placement and Retrieval Experimental Study", Radiology, 1984, 152:369-372.
Lund, G. et al., "Retrievable Vena Caval Filter Percutaneously Introduced", Radiology, 1985, vol. 155, pg. 831.
Luo, X. Y. et al., "Non-Newtonian Flow Patterns Associated With an Arterial Stenosis", Journal of Biomechanical Engineering, Nov. 1992, 114:512-514.
MacDonald, K. G. Jr., "Overview of the Epidemiology of Obesity and the Early History of Procedures to Remedy Morbid Obesity", Archives of Surgery, Apr. 2003, 138(4):357-360.
Machado, L.G. et al., "Medical Applications of Shape Memory Alloys", Brazilian Journal of Medical and Biological Research, 2003, 36:683-691.
Magnant, J.G. et al., "Current Use of Inferior Vena Cava Filters", Journal of Vascular Surgery, Nov. 1992, vol. 16, No. 5, pp. 701-706.
Malden et al., "Transvenous Retreival of Misplaced Stainless Steel Greenfield Filters" JVIR 3:703-708 (1992).
Manke, C. et al., "MR Imaging-Guided Stent Placement in Iliac Arterial Stenoses: A Feasibility Study", Radioilogy, 2001, 219:527-534.
Marston, W.A. et al., "Re: Comparison of the AngioJet Rheolytic Catheter to Surgical Thrombectomy for the Treatment of Thrombosed Hemodialysis Grafts", Journal of Vascular and Interventional Radiology (Letters to the Editor), Sep. 2000, vol. 11, No. 8, pp. 1095-1099.
Matteson, B. et al., "Role of Venous Duplex Scanning in Patients With Suspected Pulmonary Embolism", The Journal of Vascular Surgery, 1996, 24:768-773.
Matthews, B. D. et al., "Inferior Vena Cava Filter Placement: Preinsertion Inferior Vena Cava Imaging", The American Surgeon, Aug. 2003, vol. 69, No. 8, pp. 649-653.
Mattos, M.A. et al., "Prevalence and Distribution of Calf Vein Thrombosis in Patients With Symptomatic Deep Venous Thrombosis: A Color-Flow Duplex Study", Journal of Vascular Surgery, 1996, 24:738-744.
Maxwell, R.A. et al., "Routine Prophylactic Vena Cava Filtration is Not Indicated After Acute Spinal Cord Injury", The Journal of Trauma: Injury, Infection, and Critical Care, 2002, 52:902-906.
McCowan, T.C. et al., "Complications of the Nitinol Vena Caval Filter", Journal of Vascular and Interventional Radiology, 1992, 3:401-408.
McMurtry, A.L. et al., "Increased Use of Prophylactic Vena Cava Filters in Trauma Patients Failed to Decrease Overall Incidence of Pulmonary Embolism", Journal of the American College of Surgeons, 1999, 189:314-320.
Meissner, M.H. et al., Venous Thromoembolism in Trauma: A Local Manifestation of Systemic Hypercoagulability?, The Journal of Trauma: Injury, Infection, and Critical Care, Feb. 2003, vol. 54, No. 2, pp. 224-231.
Melinek, J. et al., "Autopsy Findings Following Gastric Bypass Surgery for Morbid Obesity", Arch Path Lab Med, 2002 126:1091-1095.
Mihara, H. et al., "Use of Temporary Vena Cava Filters After Catheter-Directed Fragmentation and Thrombolysis in Patients With Acute Pulmonary Thromboembolism", Japanese Circulartion Journal, Jun. 1998, vol. 62, pp. 462-464.

(56) References Cited

OTHER PUBLICATIONS

Miller, A. C., "British Thoracic Society Guidelines for the Management of Suspected Acute Pulmonary Embolism", Thorax, Jun. 2003, 58(6): 470-483.
Miller, Karl E., "Indications for Vena Cava Filters for Recurrent DVT", American Family Physician, Feb. 1, 2003, vol. 67, No. 3, p. 593.
Millward, S., "Re: Temporary IVC Filtration Before Patent Foramen Ovale Closure in a Patient With Paradoxic Embolism", Letter to the Editor, J Vasc Intery Radiol. Jul. 2003;14(7):937.
Millward, S.F. et a l., "Preliminary Clinical Experience with the Gunther Temporary Inferior Vena Cava Filter", Journal of Vascular and Interventional Radiology, 1994, 5:863-868.
Millward, S.F. et al., "Gunther Tulip Filter Preliminary Clinical Experience With Retrieval", Journal of Vascular and Interventional Radiology, 2000, 11:75-82.
Millward, S.F. et al., "Gunther Tulip Retrievable Vena Cava Filter: Results From the Registry of the Canadian Interventional Radiology Association", Journal of Vascular and Interventional Radiology, 2001, 12:1053-1058.
Millward, S.F. et al., "LGM (Vena Tech), Vena Caval Filter: Clinical Experience in 64 Patients", Journal of Vascular and Interventional Radiology, Nov. 1991, 2:429-433.
Millward, S.F. et al., "LGM (Vena Tech), Vena Caval Filter: Experience at a Single Institution", Journal of Vascular and Interventional Radiology, Mar.-Apr. 1994, 5:351-356.
Millward, S.F. et al., "Reporting Standards for Inferior Venal Caval Filter Placement and Patient Follow-Up: Supplement for Temporary and Retrievable/Optional Filters", Journal of Vascular and Interventional Radiology, Apr. 2005, 16:441-443.
Millward, S.F., "Gunther Tulip Retrievable Filter Why, When and How?", JACR, Jun. 2001, vol. 52, No. 3, pp. 188-192.
Millward, S.F., "Temporary and Retrievable Inferior Vena Cava Filters Current Status", Journal of Vascular and Interventional Radiology, May-Jun. 1998, vol. 9, No. 3, pp. 381-387.
Mobin-Uddin, K. et al., "Evolution of a New Device for the Prevention of Pulmonary Embolism", The American Journal of Surgery, vol. 168, Oct. 1994, pp. 330-334.
Mohan, C.R. et al., "Comparative Efficacy and Complications of Vena Caval Filters", Journal of Vascular Surgery, 1995, 21:235-236.
Montessuit, M. et al., "Screening for Patent Foramen Ovale and Prevention of Paradoxical Embolus", Ann Fasc Surg, 1997, 11:168-172.
Montgomery, K.D. et al., The Detection and Management of Proximal Deep Venous Thrombosis in Patients With Acute Acetabular Fractures: A Follow-up Report:, Journal of Orthopedic Trauma, Jul. 1997, 1(5):330-336.
Mortele, K. J. et al., "The Swedish Laparoscopic Adjustable Gastric Banding for Morbid Obesity: Radiologic Findings in 218 Patients", American Journal of Roentgenology, 2001, 177:77-84.
Munir, M.A. et al., "An in Situ Technique to Retrieve an Entrapped J-Tip Guidewire From an Inferior Vena Cava Filter", Anesth Analo, 2002, 95:308-309.
Murakami, M. M et al., "Deep Venous Thrombosis Prophylaxis in Trauma: Improved Compliance With a Novel Miniaturized Pneumatic Compression Device", Journal of Vascular Surgery, 2003, 38:923-927.
Nakagawa, N. et al., "A Retrievable Nitinol Vena Cava Filter: Experimental and Initial Clinical Results", Journal of Vascular and Interventional Radiology, 1994, 5:507-512.
Nakajima, Osamu et al., "Massive Deep Vein Thrombosis After Cesarean Section Treated With a Temporary Inferior Vena Cava Filter: A Case Report", J Cardioi 2000; 36(5): pp. 337-342.
Napolitano, L. M. et al., "Asymptomatic Deep Venous Thrombosis in the Trauma Patient: Is an Aggressive Screening Protocol Justified?", The Journal of Trauma: Injury, Infection, and Critical Care, 1997, vol. 39, No. 4, pp. 651-659.
Nazario, R. et al., "Treatment of Venous Thromboembolism", Cardiology in Review, 2002, 10(4):249-259.

Neeman, Z. et al., "Metastatic Involvement of a Retrieved Inferior Vena Cava Filter", J Vasc Interv Radiol. Dec. 2003; 14(12): 1585.
Neill, A. M. et al., "Retrievable Inferior Vena Caval Filter for Thromboembolic Disease in Pregnancy", British Journal of Obstetrics and Gynaecology, Dec. 1997, vol. 104, pp. 1416-1418.
Hammond, F.M. et al., "Venous Thromboembolism in the Patient With Acute Traumatic Brain Injury: Screening, Diagnosis, Prophylaxis, and Treatment Issues", Journal of Head Trauma Rehabilitation, Feb. 1998, vol. 13, No. 1, pp. 36-48.
Hansen, James, "Metals that Remember", Science 81, vol. 2, No. 5, pp. 44-47, Jun. 1981.
Hardhammar, P.A. et al., "Reduction in Thrombotic Events With Heparin-Coated Palmaz-Schatz Stents in Normal Porcine Coronary Arteries", Circulation, Feb. 1, 1996, vol. 93, No. 3, pp. 423-430.
Harold, K.L. et al., "Laparoscopic Approach to Open Gastric Bypass", The American Journal of Surgery, 2002, 184:61-62.
Harries, S.R., "Long-Term Follow-Up of the Antheor Inferior Vena Cava Filter", Clinical Radiology, 1998, 53:350-352.
Harris, E.J. Jr. et al., "Phlegmasia Complicating Prophylactic Percutaneous Inferior Vena Caval Interruption: A Word of Caution", Journal of Vascular Surgery, 1995, vol. 22, No. 5, pp. 606-611.
Hastings, G.S. et al., "Repositioning the 12-F Over-the-Wire Greenfield Filter", Journal of Vascular and Interventional Radiology, 2000, 11:1207-1210.
Hawkins, S.P. et al., "The Simon Nitinol Inferior Vena Cava Filter: Preliminary Experience in the UK", Clinical Radiology, 1992, 46:378-380.
Headrick, J.R. et al., "The Role of Ultrasonography and Inferior Vena Cava Filter Placement in High-Risk Trauma Patients", American Surgeon, Jan. 1997, vol. 63, Issue 1.
Helfet, D., Magnetic Resonance Venography to Evaluate Deep Venous Thrombosis in Patients With Pelvic and Acetabular Trauma, The Journal of Trauma: Injury, Infection, and Critical Care, Jul. 2001, p. 178.
Heng, J.T. et al., "Occlusion of Persistent Left Superior Vena Cava to Unroofed Coronary Sinus Using Vena Cava Filter and Coils", Hears, Jun. 1997, vol. 77, No. 6, pp. 579-580.
Henkle, G. et al., "Patterns of Referral for Inferior Vena Caval Filtration: Delays and Their Impact", American Journal of Roentgenology, Oct. 2004, 183:1021-1024.
Hicks, M.E. et al., "Prospective Anatomic Study of the Inferior Vena Cava and Renal Veins: Comparison of Selective Renal Venography With Cavography and Relevance in Filter Placement", Journal of Vascular and Interventional Radiology, 1995, 6:721-729.
Higa, K.D. et al., "Laparoscopic Roux-en-Y Gastric Bypass for Morbid Obesity", Archives of Surgery, Sep. 2000, vol. 135, No. 9, pp. 1029-1034.
Hill, S.L. et al., "Deep Venous Thrombosis in the Trauma Patient", The American Surgeon, Jun. 1994, vol. 60, pp. 405-408.
Hingorani, A. et al., "Upper Extremity Deep Venous Thrombosis and Its Impact on Morbidity and Mortality Rates in a Hospital-Based Population", Journal of Vascular Surgery, Nov. 1997, 26:853-860.
Hirsch, D. R. et al., "Prevalence of Deep Venous Thrombosis Among Patients in Medical Intensive Care", JAMA, Jul. 26, 1995, 274(4):335337.
Hirsch, S. B. et al., Case Reports: Accidental Placement of the Greenfield Filter in the Heart: Report of Two Cases et al., Journal of Vascular Surgery, Dec. 1987, vol. 6, No. 6.
Hoff, W. S. et al., "Early Experience With Retrievable Inferior Vena Cava Filters in High-Risk Trauma Patients", Journal of the American College of Surgeons, Dec. 2004, vol. 199, No. 6, pp. 869-874.
Holtzman, R.B. et al., "Comparison of Carbon Dioxide and Iodinated Contrast for Cavography Prior to Inferior Vena Cava Filter Placement", The American Journal of Surgery, 2003, 185:364-368.
Hosaka, J. et al., "Placement of a Spring Filter During Interventional Treatment of Deep Venous Thrombosis to Reduce the Risk of Pulmonary Embolism", Acta Radiologica, 1999, 40:545-551.
Hughes, G.C. et al., "The Use of a Temporary Vena Caval Interruption Device in High-Risk Trauma Patients Unable to Receive Standard Venous Thromboembolism Prophylaxis", Investigative Radiology, Feb. 1999, vol. 46, No. 2, pp. 246-249.

(56) References Cited

OTHER PUBLICATIONS

Hunter, D.W. et al., "Retrieving the Amplatz Retrievable Vena Cava Filter", Cardiovascular and Interventional Radiology, 1987, 10:32-36.

Hyers, T. M. et al., "Antithrombotic Therapy for Venous Thromboembolic Disease", Chest, Jan. 2001, 119 (1):176S-193S.

Ihnat, D. M. et al., "Treatment of Patients With Venous Thromboembolism and Malignant Disease: Should Vena Cava Filter Placement Be Routine?", Journal of Vascular Surgery, Nov. 1998, vol. 28, No. 8, pp. 800-807.

Inge, T. H. et al., "Bariatric Surgery for Severely Overweight Adolescents: Concerns and Recommendations", Pediatrics, Jul. 2004, vol. 114, No. 1, pp. 217-223.

Izutani, H. et al., "Migration of an Inferior Vena Cava Filter to the Right Ventricle and Literature Review", Can J Cardiol, Feb. 2004, vol. 20, No. 2, pp. 233-235.

Jackson Slappy, A.L. et al., "Delayed Transcaval Renal Penetration of a Greenfield Filter Presenting as Symptomatic Hydronephrosis", The Journal of Urology, Apr. 2002, vol. 167, pp. 1778-1779.

Jacobs, D. G. et al., "The Role of Vena Caval Filters in the Management of Venous Thromboembolism" The American Surgeon, Aug. 2003, vol. 69, No. 8, pp. 635-642.

Jacobs, D. G. et al., Letters to the Editor, The Journal of Trauma, Dec. 1997, vol. 43, No. 6, pp. 988-989.

Jaeger, H.J. et al., "A Physiologic in Vitro Model of the Inferior Vena Cava With a Computer-Controlled Flow System for Testing of Inferior Vena Cava Filters", Investigative Radiology, Sep. 1997, vol. 32, No. 9, pp. 511-522.

Jain, V. et al., "Preoperative Vena Caval Interruption for Venous Thrombosis Associated With Ovarian Malignancy", Acta Obstet Gynecol Scand 2002: 81: 270-271.

James Kevin V. et al., "Tricuspid Insufficiency After Intracardiac Migration of a Greenfield Filter: Case Report and Review of the Literature", Journal of Vascular Surgery, Sep. 1996, vol. 24, No. 3, pp. 494-498.

Jarrett B.P. et al., Inferior Vena Cava Filters in Malignant Disease, Journal of Vascular Surgery, 2002, 36:704-707.

Joels, C. S. et al., "Complications of Inferior Vena Cava Filters", The American Surgeon, Aug. 2003, vol. 69, No. 8, pp. 654-659.

Johnson, M.S., "Current Strategies for the Diagnosis of Pulmonary Embolus", Journal of Vascular and Interventional Radiology, 2002, 13:13-23.

Johnson, S.P. et al., "Single Institution Prospective Evaluation of the Over-The-Wire Greenfield Vena Caval Filter", Journal of Vascular and Interventional Radiology, 1998, 9:766-773.

Jones, A.L. et al., "Case Report: Use of an IVC Filter in the Management of IVC Thrombosis Occurring as a Complication of Acute Pancreatitis", Clinical Radiology, 1998, 53:462-464.

Joshi, A. et al., "Filter-Related, Thrombotic Occlusion of the Inferior Vena Cava Treated With a Gianturco Stent", Journal of Vascular and Interventional Radiology, 2003, 14:381-385.

JP 2008-543433 filed May 30, 2008 Office Action dated Jan. 11, 2012.

Kaplan, S. et al., "Surgical Management of Renal Cell Carcinoma With Inferior Vena Cava Tumor Thrombus", The American Journal of Surgery, 2002, 183:292-299.

Karmy-Jones, R. et al., "Surgical Management of Cardiac Arrest Caused by Massive Pulmonary Embolism in Trauma Patients", The Journal of Trauma: Injury, Infection, and Critical Care, 2000, vol. 48, No. 3, pp. 519-520.

Kasirajan, K. et al., "Percutaneous AngioJet Thrombectomy in the Management of Extensive Deep Venous Thrombosis", Journal of Vascular and Interventional Radiology, 2001, 12:179-185.

Katsamouris, A.A. et al., "Inferior Vena Cava Filters: In Vitro Comparison of Clot Trapping and Flow Dynamics", Radiology, 1988, 166:361-366.

Kaufman, J.A. et al., "Guide-Wire Entrapment by Inferior Vena Caval Filters: In Vitro Evaluation", Radiology, 1996, 198:71-76.

Kaufman, J.A. et al., "Operator Errors During Percutaneous Placement of Vena Cava Filters", American Journal of Roentgenology, Nov. 1995, 165:1281-1287.

Kaufman, John A., "Re: Metastatic Involvement of a Retrieved Inferior Vena Cava Filter", Journal of Vascular and Interventional Radiology, Jul. 2004, vol. 15, No. 7, pp. 775-776.

Kaw, L.L., Jr. et al., "Use of Vena Cava Filters", Techniques in Orthopaedics, 2004, 19(4):327-336.

Kazmers, A. et al., "Duplex Examination of the Inferior Vena Cava", The American Surgeon, Oct. 2000, vol. 66, pp. 986-989.

Kazmers, A. et al., "Intraoperative Insertion of Greenfield Filters: Lessons Learned in a Personal Series of 152 Cases", The American Surgeon, Oct. 2002, vol. 68, pp. 877-882.

Dabbagh, A. et al., "Late Complication of a Greenfield Filter Associating Caudal Migration and Perforation of the Abdominal Aorta by a Ruptured Strut", Journal of Vascular Surgery, Aug. 1995, vol. 22, No. 2, pp. 182-187.

Dake, M.D. et al., "Thrombolytic Therapy in Venous Occlusive Disease", Journal of Vascular and Interventional Radiology, 1995, 6:73S-77S.

Dalman, R. et al., "Cerebrovascular Accident After Greenfield Filter Placement for Paradoxical Embolism", Journal of Vascular Surgery, Mar. 1989, vol. 9, No. 3, pp. 452-454.

Danetz, J. S. et al., "Selective Venography Versus Nonselective Venography Before Vena Cava Filter Placement: Evidence for More, Not Less", Journal of Vascular Surgery, Nov. 2003, Vo. 38, No. 5, pp. 928-934.

Danikas, Dimitrios et al., "Use of a Fogarty Catheter to Open an Incompletely Expanded Vena Tech-LGM Vena Cava Filter", Angiology, Apr. 2001, vol. 52, No. 4, pp. 283-286.

Darcy, M.D. et al., "Short-Term Prophylaxis of Pulmonary Embolism by Using a Retrievable Vena Cava Filter", American Journal of Roentgenology, 1986, 147:836-838.

Dardik, Alan et al., "Vena Cava Filter Ensnarement and Delayed Migration: An Unusual Series of Cases", Journal of Vascular Surgery, Nov. 1997, vol. 26, No. 5.

David, W. et al., "Pulmonary Embolus After Vena Cava Filter Placement", The American Surgeon, Apr. 1999, vol. 65, pp. 341-346.

Davidson, B.L., "DVT Treatment in 2000: State of the Art", Orthopedics, Jun. 2000, 23(6):pp. S651-s654.

Davison, Brian D. et al., "TrapEase Inferior Vena Cava Filter Placed Via the Basilic Arm Vein: A New Antecubital Access", J Vasc Interv Radiol, Jan. 2002, 13:107-109.

de Godoy, José Maria Pereira et al., "In-Vitro Evaluation of a New Inferior Vena Cava Filter—The Stent-Filter", Vascular and Endovascular Surgery, Nov. 3, 2004, vol. 38, pp. 225-228.

de Gregorio, M.A. "Inferior Vena Cava Filter Update", Arch Bronconeumol, 2004, vol. 40, No. 5, pp. 193-195.

De Gregorio, M.A. et al., "Animal Experience in the Gunther Tulip Retrievable Inferior Vena Cava Filter", Cardiovascular and Interventional Radiology, Nov. 2001, 24:413-417.

De Gregorio, M.A. et al., "Mechanical and Enzymatic Thrombolysis for Massive Pulmonary Embolism", Journal of Vascular and Interventional Radiology, 2002, 13:163-169.

de Gregorio, Miguel Angel et al., "The Gunther Tulip Retrievable Filter: Prolonged Temporary Filtration by Repositioning Within the Inferior Vena Cava", J Vasc Interv Radiol, Oct. 2003, 14:1259-1265.

De Gregorio, Miguel Angel et al., "Retrievability of Uncoated Versus Paclitaxel-Coated Gunther-Tulip IVC Filters in an Animal Model", J Vasc Interv Radiol, Jul. 2004,15:719-726.

Debing, E. et al., "Popliteal Venous Aneurysm With Pulmonary Embolism", Journal of Cardiovascular Surgery, Oct. 1998, vol. 39, No. 5, pp. 569-572.

Decousus, H. et al., "A Clinical Trial of Vena Caval Filters in the Prevention of Pulmonary Embolism in Patients With Proximal Deep-Vein Thrombosis", The New England Journal of Medicine, Feb. 12, 1998, vol. 338, No. 7, pp. 409-415.

DeMaria, E.J. et al., "Results of 281 Consecutive Total Laparoscopic Roux-en-Y Gastric Bypasses to Treat Morbid Obesity", Annals of Surgery, 2002, vol. 235, No. 5 pp. 640-647.

(56) References Cited

OTHER PUBLICATIONS

Dennis, J.W. et al., "Efficacy of Deep Venous Thrombosis Prophylaxis in Trauma Patients and Identification of High-Risk Groups", The Journal of Trauma, 1993, vol. 35, No. 1, pp. 132-137.

Denny, D.F. Jr., "Errant Percutaneous Greenfield Filter Placement Into the Retroperitoneum" Journal of Vascular Surgery Jun. 1991, vol. 13, No. 6.

Dewald, C.L. et al., Vena Cavography With CO2 Versus With Iodinated Contrast Material for Inferior Vena Cava Filter Placement: A Prospective Evaluation, Radiology, 2000, 216:752-757.

Dibie, A. et al., "In Vivo Evaluation of a Retrievable Vena Cava Filter—The Dibie-Musset Filter: Experimental Results", Cardiovascular and Interventional Radiology, 1998, 21:151-157.

Dick, A. et al., "Declotting of Embolized Temporary Vena Cava Filter by Ultrasound and the Angiojet: Comparative Experimental in Vitro Studies", Investigative Radiology, Feb. 1998, vol. 33(2), pp. 91-97.

Doherty, C., "Special Problems of Massive Obesity", Primary Care Physician's Resource Center, file://d:\Special%20Problems%20of%20Massive%20Obesity.htm, retrieved Jul. 26, 2005.

Dotter et al., "Transluminal Expandable Nitinol Coil Stent Grafting: Preliminary Report" Radiology 147:259-260 (Apr. 1983).

Duperier, T. et al., "Acute Complications Associated With Greenfield Filter Insertion i High-Risk Trauma Patients", The Journal of Trauma: Injury, Infection, and Critical Care, Mar. 2003, vol. 54, No. 3, pp. 545-549.

Ebaugh, James L. et al., "Bedside Vena Cava Filter Placement Guided With Intravascular Ultrasound", Journal of Vascular Surgery, Jul. 2001,34:21-26.

Edlow, J.A., "Emergency Department Management of Pulmonary Embolism", Emergency Medicine Clinics of North America, Nov. 2001, vol. 19, No. 4, pp. 995-1011.

Egermayer, P., "Follow-Up for Death or Recurrence Is Not a Reliable Way of Assessing the Accuracy of Diagnostic Tests for Thromboembolic Disease", Chest 1997, 111:1410-1413.

Ekim, N. et al., "Pulmonary Thromboembolism With Massive Vaginal Bleeding Due to Thrombolytic Therapy", Respirology, 2003, 8:246-248.

Engmann, E. et al., "Clinical Experience With the Antecubital Simon Nitinol IVC Filter", Journal of Vascular and Interventional Radiology, 1998, 9:774-778.

EP 99951426 European Search Report dated Mar. 18, 2003.

Epstein et al., "Experience with the Amplatz Retrievable Vena Cava Filter" Radiology 175:105-110 (1989).

Fava, M. et al., "Massive Pulmonary Embolism: Percutaneous Mechanical Thrombectomy During Cardiopulmonary Resuscitation", Journal of Vascular and Intervention Radiology, 2005, 16:119-123.

Fava, M. et al., "Massive Pulmonary Embolism: Treatment With the Hydrolyser Thrombectomy Catheter", Journal of Vascular and Intervention Radiology, 2000, 11:1159-1164.

Feezor, R.J. et al., "Duodenal Perforation With an Inferior Vena Cava Filter: an Unusual Cause of Abdominal Pain", Journal of Vascular Surgery, 2002, pp. 1-3.

Fernandez, A.Z. Jr. et al., "Multivariate Analysis of Risk Factors for Death Following Gastric Bypass for Treatment of Morbid Obesity", Annals of Surgery, May 2004, vol. 239, No. 5, pp. 698-703.

Ferral, H., "Regarding 'Lessons Learned From a 6-Year Clinical Experience With Superior Vena Cava Greenfield Filters'", Journal of Vascular Surgery, Apr. 2001, vol. 33, No. 4.

Ferraro, F. et al., "Thromboembolism in Pregnancy: A New Temporary Caval Filter", Miverva Anestesiologica, 2001, vol. 67, No. 5, pp. 381-385.

Ferris, E.J. et al., "Percutaneous Inferior Vena Caval Filters: Follow-Up of Seven Designs in 320 Patients", Radiology 1993, 188:851-856.

Fink, S. et al., "Pulmonary Embolism and Malpractice Claims", Southern Medical Journal, Dec. 1998, vol. 91, No. 12, pp. 1149-1152.

Fobbe, Franz et al., "Gunther Vena Caval Filter: Results of Long-Term Follow-Up", AJR, Nov. 1988,151:1031-1034.

Foley, M. et al., "Pulmonary Embolism After Hip or Knee Replacement: Postoperative Changes on Pulmonary Scintigrams in Asymptomatic Patients", Radiology, 1989, 172:481-485.

Fraser, J.D. et al., "Deep Venous Thrombosis: Recent Advances and Optimal Investigation With US", Radiology, 1999, 211:9-24.

Frezza, E.E. et al., "Entrapment of a Swan Ganz Catheter in an IVC Filter Requiring Caval Exploration", Journal of Cardiovascular Surgery, 1999, 40:905-908.

Friedell, M.L. et al., "Case Report: Migration of a Greenfield Filter to the Pulmonary Artery: Case Report", Journal of Vascular Surgery, Jun. 1986, vol. 3, No. 6, pp. 929-931.

Friedland, M. et al., "Vena Cava Duplex Imaging Before Caval Interruption", Journal of Vascular Surgery, Oct. 1995, vol. 24, No. 4, pp. 608-613.

Gabelmann, A. et al., "Percutaneous Retrieval of Lost of Misplaced Intravascular Objects", American Journal of Radiology, Jun. 2001, 176:1509-1513.

Galus, Maria et al., "Indications for inferior vena cava filters," Internal Medicine, Aug. 11, 1997; 157, 15; Health and Medical Complete, pp. 1770-1771.

U.S. Appl. No. 11/966,203, filed Dec. 28, 2007 Final Office Action dated Dec. 4, 2009.

U.S. Appl. No. 11/966,203, filed Dec. 28, 2007 Non-Final Office Action dated Aug. 17, 2009.

U.S. Appl. No. 11/997,832, filed Aug. 20, 2008 Non-Final Office Action dated Aug. 16, 2010.

U.S. Appl. No. 11/997,832, filed Aug. 20, 2008 Non-Final Office Action dated Feb. 23, 2011.

U.S. Appl. No. 12/093,814, filed Jun. 8, 2009 Non-Final Office Action dated Jul. 10, 2012.

U.S. Appl. No. 12/095,700, filed Jun. 17, 2010 Final Office Action dated Sep. 28, 2012.

U.S. Appl. No. 12/095,700, filed Jun. 17, 2010 Non-Final Office Action dated Jun. 11, 2012.

U.S. Appl. No. 12/095,700, filed Jun. 17, 2010 Non-Final Office Action dated Oct. 9, 2013.

U.S. Appl. No. 12/095,991, filed Jul. 31, 2008 Advisory Action dated Sep. 20, 2012.

U.S. Appl. No. 12/095,991, filed Jul. 31, 2008 Final Office Action dated May 4, 2012.

U.S. Appl. No. 12/095,991, filed Jul. 31, 2008 Non-Final Office Action dated Nov. 14, 2011.

U.S. Appl. No. 12/095,991, filed Jul. 31, 2008 Notice of Abandonment dated Nov. 23, 2012.

U.S. Appl. No. 12/096,783, filed Aug. 20, 2009 Non-Final Office Action dated Apr. 25, 2013.

U.S. Appl. No. 12/299,300, filed Feb. 24, 2009 Non-Final Office Action dated Apr. 30, 2012.

U.S. Appl. No. 12/299,300, filed Feb. 24, 2009 Notice of Allowance dated Aug. 17, 2012.

U.S. Appl. No. 12/299,304, filed Jun. 16, 2009 Non-Final Office Action dated Aug. 21, 2013.

U.S. Appl. No. 12/299,304, filed Jun. 16, 2009 Non-Final Office Action dated Jun. 21, 2012.

U.S. Appl. No. 12/303,545, filed Jun. 29, 2009 Advisory Action dated Jul. 24, 2013.

U.S. Appl. No. 12/303,545, filed Jun. 29, 2009 Non-Final Office Action dated Jun. 8, 2012.

U.S. Appl. No. 12/336,454, filed Dec. 12, 2008 Non-Final Office Action dated Jan. 24, 2011.

U.S. Appl. No. 12/727,116, filed Mar. 18, 2010 Non-Final Office Action dated Jul. 18, 2012.

U.S. Appl. No. 12/846,680, filed Jul. 29, 2010 Advisory Action dated Feb. 8, 2013.

U.S. Appl. No. 12/846,680, filed Jul. 29, 2010 Final Office Action dated Nov. 30, 2012.

U.S. Appl. No. 12/846,680, filed Jul. 29, 2010 Non-Final Office Action dated May 7, 2012.

U.S. Appl. No. 12/846,680, filed Jul. 29, 2010 Notice of Allowance dated Aug. 28, 2013.

(56) References Cited

OTHER PUBLICATIONS

U.S. Appl. No. 13/009,727, filed Jan. 19, 2011 Notice of Allowance dated Apr. 27, 2012.
U.S. Appl. No. 13/170,054, filed Jun. 27, 2011 Final Office Action dated Apr. 3, 2013.
U.S. Appl. No. 13/170,054, filed Jun. 27, 2011 Non-Final Office Action dated Jul. 2, 2012.
U.S. Appl. No. 13/170,054, filed Jun. 27, 2011 Notice of Allowance dated Jul. 15, 2013.
U.S. Appl. No. 13/300,469, filed Nov. 18, 2011 Non-Final Office Action dated Sep. 20, 2012.
U.S. Appl. No. 13/300,469, filed Nov. 18, 2011 Notice of Allowance dated Jan. 10, 2013.
U.S. Appl. No. 13/414,605, filed Mar. 7, 2012 Non-Final Office Action dated Aug. 12, 2013.
U.S. Appl. No. 13/688,031, filed Nov. 28, 2012 Final Office Action dated Jul. 9, 2013.
U.S. Appl. No. 13/688,031, filed Nov. 28, 2012 Non-Final Office Action dated Mar. 14, 2013.
Valji, K., "Evolving Strategies for Thrombolytic Therapy of Peripheral Vascular Occlusion", Journal of Vascular and Interventional Radiology, 2000, 11:411-420.
Van Ha, Thuong G. et al., "Removal of Gunther Tulip Vena Cava Filter Through Femoral Vein Approach", Journal of Vascular and Interventional Radiology, 2005, 16:391-394.
Van Natta, Timothy L. et al., "Elective Bedside Surgery in Critically Injured Patients is Safe and Cost-Effective", American Surgery, May 1998, 227(5):618-626.
Vedantham, S. et al., "Endovascular Recanalization of the Thrombosed Filter-Bearing Inferior Vena Cava", Journal of Vascular and Interventional Radiology, 2003, 14:893-903.
Vedantham, S. et al., "Lower Extremity Venous Thrombolysis With Adjunctive Mechanical Thrombectomy", Journal of Vascular and Interventional Radiology, 2002, 13:1001-1008.
Vedantham, S. et al., "Pharmacomechanical Thrombolysis and Early Stent Placement for Iliofemoral Deep Vein Thrombosis", Journal of Vascular and Interventional Radiology, 2004, 15:565-574.
Velmahos, G. C. et al., "Inability of an Aggressive Policy of Thromboprophylaxis to Prevent Deep Venous Thrombosis (DVT) in Critically Injured Patients: Are Current Methods of DVT Prophylaxis Insufficient?", Journal of the American College of Surgeons, 1998, 187:529-533.
Velmahos, G. C. et al., "Prevention of Venous Thromboembolism After Injury: An Evidence-Based Report—Part 1: Analysis of Risk Factors and Evaluation of the Role of Vena Caval Filters", The Journal of Trauma: Injury, Infection, and Critical Care, Jul. 2000, 49:132-139.
Velmahos, G. C. et al., "Prevention of Venous Thromboembolism After Injury: An Evidence-Based Report—Part II: Analysis of Risk Factors and Evaluation of the Role of Vena Caval Filters", The Journal of Trauma: Injury, Infection, and Critical Care, Jul. 2000, 49:140-144.
Velmahos, G. C. et al., "Spiral Computed Tomography for the Diagnosis of Pulmonary Embolism in Critically Ill Surgical Patients", Archives of Surgery, May 2001, 136(5):505-511.
Venbrux, Anthony C., "Protection Against Pulmonary Embolism: Permanent and Temporary Caval Filters" Presentation, Department of Radiology-CVDL, The Johns Hopkins Medical Institutions, Baltimore MD, 7 pages, 2007.
Vesely, T. M. et al., "Preliminary Investigation of the Irie Inferior Vena Caval Filter", Journal of Vascular and Interventional Radiology, 1996, 7:529-535.
Vorwerk, D. et al., "Use of a Temporary Caval Filter to Assist Percutaneous Iliocaval Thrombectomy: Experimental Results", Journal of Vascular and Interventional Radiology, Sep.-Oct. 1995, 6 (5):737-740.

Vos, Louwerens D. et al., "The Gunther Temporary Inferior Vena Cava Filter for Short-Term Protection Against Pulmonary Embolism", Cardiovascular and Interventionai Radiology, 1997, 20:91-97.
Vrachliotis, T. G. et al., "Percutaneous Management of Extensive Clot Trapped in a Temporary Vena Cava Filter", Journal of Endovascular Therapy, 2003, 10:1001-1005.
Wakefield, T. W., Treatment Options for Venous Thrombosis, Journal of Vascular Surgery, Mar. 2000, 31 (3):613-620.
Gamblin, T.C. et al., "A Prospective Evaluation of a Bedside Technique for Placement of Inferior Vena Cava Filters: Accuracy and Limitations of Intravascular Ultrasound", The American Surgeon, May 2003, vol. 69, pp. 382-386.
Garcia, N.D., "Is Bilateral Ultrasound Scanning of the Legs Necessary for Patients With Unilateral Symptoms of Deep Vein Thrombosis", Journal of Vascular Surgery, 2001, 34:792-797.
Gayer, G. et al., "Congenital Anomalies of the Inferior Vena Cava Revealed on CT in Patients With Deep Vein Thrombosis", American Journal of Roentgenology, Mar. 2003, vol. 180, pp. 729-732.
Geerts, W.H., "A Prospective Study of Venous Thromboembolism After Major Trauma", Dec. 15, 1994, vol. 331, No. 24, pp. 1601-1606.
Gelbfish, G. A. et al., "Intracardiac and Intrapulmonary Greenfield Filters: A Long-Term Follow-Up", Journal of Vascular Surgery, Nov. 1991, Vo. 14, No. 5, pp. 614-617.
Gelfand, E.V. et al., "Venous Thromboembolism Guidebook, Fourth Edition", Critical Pathways in Cardiology, Dec. 2003, vol. 2, No. 4, pp. 247-265.
Georgopoulos, S.E. et al., "Paradoxical Embolism", Journal of Cardiovascular Surgery, 2001, 42:675-677.
Ginsberg, M.S. et al., "Clinical Usefulness of Imaging Performed After CT Angiography That Was Negative for Pulmonary Embolus in a High-Risk Oncologic Population", American Journal of Roentgenology, Nov. 2002, 179:1205-1208.
Girard, P. et al., Medical Literature and Vena Cava Filters*, Chest, 2002, 122:963-967.
Girard, T. D. et al., "Prophylactic Vena Cava Filters for Trauma Patients: A Systematic Review of the Literature", Thrombosis Research, 2003, 112:261-267.
Goldberg, M.E., "Entrapment of an Exchange Wire by an Inferior Vena Caval Filter: A Technique for Removal", Anesth Analg., Apr. 2003, 96:4, 1235-1236.
Goldhaber, S.Z. et al., "Acute Pulmonary Embolism: Part II Risk Stratification, Treatment, and Prevention", Circulation, 2003, 108:2834-2838.
Goldhaber, S.Z., "A Free-Floating Approach to Filters", Archives of Internal Medicine, Feb. 10, 1997, vol. 157, No. 3, pp. 264-265.
Goldhaber, S.Z., "Venous Thromboembolism in the Intensive Care Unit: The Last Frontier for Pro . . . ", Chest, Jan. 1998, 113(1):5-7.
Goldman, H.B. et al., "Ureteral Injury Secondary to an Inferior Vena Caval Filter", The Journal of Urology, Nov. 1996, vol. 156, No. 5, p. 1763.
Golueke, P.J. et al., "Interruption of the Vena Cava by Means of the Greenfield Filter: Expanding the Indications", Surgery, Jan. 1988, vol. 103, No. 1, pp. 111-117.
Gonze, M.D. et al., "Orally Administered Heparin for Preventing Deep Venous Thrombosis", American Journal of Surgery, Aug. 1998, vol. 176, pp. 176-178.
Goodman, L.R. et al., "Subsequent Pulmonary Embolism: Risk After a Negative Helical CT Pulmonary Angiogram—Prospective Comparison With Scintigraphy", Radiology, 2000, 215:535-542.
Gosin, J. S., "Efficacy of Prophylactic Vena Cava Filters in High-Risk Trauma Patients", Annals of Vascular Surgery, 1997, 11:100-105.
Gottlieb, R.N., "Randomized Prospective Study Comparing Routine Versus Selective Use of Sonography of the Complete Calf in Patients With Suspected Deep Venous Thrombosis", American Journal of Roentgenology, Jan. 2003, 180:241-245.
Grandas, O.H. et al., "Deep Venous Thrombosis in the Pediatric Trauma Population: An Unusual Event: Report of Three Cases", The American Surgeon, Mar. 2000, vol. 66, pp. 273-276.
Grassi, C.L. et al., "Quality Improvement Guidelines for Percutaneous Permanent Inferior Vena Cava Filter Placement for the Preven-

(56) References Cited

OTHER PUBLICATIONS tion of Pulmonary Embolism", Journal of Vascular and Interventional Radiology, Sep. 2003, 14:S271-S275.
Grassi, C.L. et al., "Vena Caval Occlusion After Simon Nitinol Filter Placement: Identification With MR Imaging in Patients With Malignancy", Journal of Vascular and Interventional Radiology, 1992, 3(3):535-539.
Greene, F.L. et al., Letters to the Editor, The Journal of Trauma: Injury, Infection, and Critical Care, May 2005, vol. 5 8, No. 5, pp. 1091-1092.
Greenfield, L. J. et al., "Clinical Experience With the Kim-Ray Greenfield—Vena Caval Filter", Ann Surg, Jun. 1977, vol. 185, No. 6, pp. 692-698.
Greenfield, L. J. et al., "Experimental Embolic Capture by Asymmetric Greenfield Filters", Journal of Vascular Surgery, Sep. 1992, vol. 16, No. 3, pp. 436-444.
Greenfield, L.J. et al., "Filter Complications and Their Management", Seminars in Vascular Surgery, vol. 13, No. 3, Sep. 2000, pp. 213-216.
Greenfield, L.J. et al., "Free-Floating Thrombus and Pulmonary Embolism/Reply", Archives of Internal Medicine, Dec. 8-Dec. 22, 1997, pp. 2661-2662.
Greenfield, L.J. et al., "Limb Asymmetry in Titanium Greenfield Filters: Clinically Significant?", Journal of Vascular Surgery, 1997, 26:770-775.
Greenfield, L.J. et al., "Prophylactic Vena Caval Filters in Trauma: The Rest of the Story", Journal of Vascular Surgery, 2000, 32:490-497.
Greenfield, L.J. et al., "Recommended Reporting Standards for Vena Caval Filter Placement and Patient Follow-Up", Journal of Vascular and Interventional Radiology, 1999, 10:1013-1019.
Greenfield, L.J. et al., "Results of a Multicenter Study of the Modified Hook-Titanium Greenfield Filter" Journal of Vascular Surgery 14:253-257 (Sep. 1991).
Greenfield, L.J. et al., "The Percutaneous Greenfield Filter: Outcomes and Practice Patterns", Journal of Vascular Surgery, 2000, 32:888-893.
Greenfield, L.J. et al., "Twenty-Year Clinical Experience With the Greenfield Filter", Cardiovascular Surgery, Apr. 1995, vol. 3, No. 2, pp. 199-205.
Greenfield, L.J., "Cost vs Value in Vena Caval Filters", Chest, Jul. 1998, vol. 114, No. 1, pp. 9-10.
Greenfield, L.J., "Current Indications for and Results of Greenfield Filter Placement", Journal Vascular Surgery, May 1984, vol. 1, No. 3, pp. 502-504.
Greenfield, L.J., "Does Cervical Spinal Cord Injury Induce Higher Incidence of Complications After Prophylactic Greenfield Filter Usage?", Journal of Vascular and Interventional Radiology, Jul.-Aug. 1997, pp. 719-720.
Greenfield, L.J., "Recurrent Thromboembolism in Patients With Vena Cava Filters", Journal of Vascular Surgery, 2001, 33:510-514.
Greenfield, L.J., "Staging of Fixation and Retrievability of Greenfield Filters", Journal of Vascular Surgery, Nov. 1994, vol. 20, No. 5, pp. 744-750.
Greenfield, Lazar J. et al., "A New Intracaval Filter Permitting Continued Flow and Resolution of Emboli", Surgery, Apr. 1973, vol. 73, No. 4, pp. 599-606.
Greenfield, Lazar J. et al., "Suprarenal Filter Placement", Journal of Vascular Surgery, Sep. 1998, 28:432-438.
Greenfield, Lazar J. et al., "Vena Caval Filter Use in Patients With Sepsis", Archives of Surgery, Nov. 2003, vol. 138, No. 11, Health & Medical Complete, pp. 1245-1248.
Greenfield, Lazar J. et al ., "Extended Evaluation of the Titanium Greenfield Vena Caval Filter", Journal of Vascular Surgery, Nov. 1994, vol. 20, No. 3, pp. 458-465.
Gaither, Rolf W. et al., "Vena Caval Filter to Prevent Pulmonary Embolism: Experimental Study", Radiology, AUQust 1985,156:315-320.
Haage, Patrick et al., "Prototype Percutaneous Thrombolytic Device: Preclinical Testing in Subacute Inferior Vena Caval Thrombosis in a Pig Model", Radiology, Jul. 2001,220:135-141.
Hagspiel, K.D. et al., "Inferior Vena Cava Filters: An Update", Applied Radiology, Nov. 1998, pp. 20-34.
Hagspiel, K.L. et al., "Difficult Retrieval of a Recovery IVC Filter", Journal of Vascular and Interventional Radiology (Letters to the Editor), Jun. 2004, vol. 15, No. 6, pp. 645-650.
Hainaux, B. et al., "Intragastric Band Erosion After Laparoscopic Adjustable Gastric Banding for Morbid Obesity: Imaging Characteristics of an Underreported Complication", American Journal of Roentgenology, Jan. 2005, 184:109-112.
Hak, D.J., "Prevention of Venous Thromboembolism in Trauma and Long Bone Fractures", Current Opinion in Pulmonary Medicine, 2001, 7:338-343.
Hammer, Frank D. et al., "In Vitro Evaluation of Vena Cava Filters", Journal of Vascular and Interventionai Radiology, Nov.-Dec. 1994, 5:869-876.
Kazmers, A. et al., "Pulmonary Embolism in Veterans Affairs Medical Centers: Is Vena Cava Interruption Underutilized?", The American Surgeon, Dec. 1999, vol. 65, No. 12, pp. 1171-1175.
Kearon, C. et al., "Management of Anticoagulation Before and After Elective Surgery", The New England Journal of Medicine, May 22, 1997, vol. 336, No. 21, pp. 1506-1511.
Kellum, J. M., "Gastric Banding" Annals of Surgery, Jan. 2003, vol. 237, No. 1, pp. 17-18.
Kelly, J. et al., "Anticoagulation or Inferior Vena Cava Filter Placement for Patients With Primary Intracerebral Hemorrhage Developing Venous Thromboembolism?", Stroke, 2003, 34:2999-3005.
Kercher, K. et al., "Overview of Current Inferior Vena Cava Filters", The American Surgeon, Aug. 2003, vol. 69, pp. 643-648.
Kerlan, R.K., Jr. et al., "Residual Thrombus Within a Retrievable IVC Filter", Journal of Vascular and Interventional Radiology, 2005, 16:555-557.
Kerr, A. et al., "Bidirectional Vena Cava Filter Placement", Journal of Vascular Surgery, Oct. 1995, vol. 22, No. 4.
Khansarinia, S. et al., Prophylactic Greenfield Filter Placement in Selected High-Risk Trauma Patients, Journal of Vascular Surgery, 1995, 22:231-236.
Kim et al., "Insertion of the Simon Nitinol Caval Filter: Value of the Antecubital Vein Approach" AJR 157:521-522 (Sep. 1991).
Kim et al., "Perforation of the Inferior Vena Cava with Aortic and Vetebral Penetration by a Suprarenal Greenfield Filter" Radiology 172:721-723 (1989).
Kim et al., "The Simon Nitinol Filter: Evaluation by MR and Ultrasound" Angiology 43:541-548 (Jul. 1992).
Kim et al., "Vena Cava Filter Placement Via the External Jugular Vein" AJR 155:898-899 (Oct. 1990).
Kim, D. et al., "Insertion of the Simon Nitinol Caval Filter: Value of the Antecubital Vein Approach", American Journal of Roentgenology, Sep. 1991, 157:521-522.
Kim, J. et al., "Preliminary Report on the Safety of Heparin for Deep Venous Thrombosis Prophylaxis After Severe Head Injury", The Journal of Trauma: Injury, Infection, and Critical Care, Jul. 2002, vol. 53, No. 1, pp. 38-43.
Kim, V. et al., "Epidemiology of Venous Thromboembolic Disease", Emergency Medicine Clinics of North America, Nov. 2001, vol. 19, No. 4, pp. 839-859.
Kimmerly, W. S. et al., "Graduate Surgical Trainee Attitudes Toward Postoperative Thromboprophylaxis", Southern Medical Journal, Aug. 1999, vol. 92, No. 9, pp. 790-794.
King, J.N. et al., "Vena Cava Filters", The Western Journal of Medicine, Mar. 1992, vol. 156, No. 3, pp. 295-296.
Kinney, T. B. et al., "Regarding "Limb Asymmetry in Titanium Greenfield Filters: Clinically Significant?"", Journal of Vascular Surgery, Jun. 1998, vol. 27, No. 6.
Kinney, T.B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.

(56) References Cited

OTHER PUBLICATIONS

Kinney, T.B. et al., "Fatal Paradoxic Embolism Occurring During IVC Filter Insertion in a Patient With Chronic Pulmonary Thromboembolic Disease", Journal of Vascular and Interventional Radiology, 2001, 12:770-772.
Kinney, T.B., "Translumbar High Inferior Vena Cava Access Placement in Patients With Thrombosed Inferior Vena Cava Filters", Journal of Vascular and Interventional Radiology, 2003, 14:1563-1567.
Kinney, T.B., "Update on Inferior Vena Cava Filters", Journal of Vascular and Interventional Radiology, 2003, 14:425-440.
Kistner, R. L., Definitive Diagnosis and Definitive Treatment in Chronic Venous Disease: A Concept Whose Time Has Come:, Journal of Vascular Surgery, Nov. 1996, vol. 24, No. 5, pp. 703-710.
Knudson, M. M. et al., "Prevention of Venous Thromboembolism in Trauma Patients", The Journal of Trauma, Sep. 1994, vol. 37, No. 3, pp. 480-487.
Knudson, M. M. et al., "Thromboembolism After Trauma—An Analysis of 1602 Episodes From the American College of Surgeons National Trauma Data Bank" Annals of Surgery, Sep. 2004, vol. 240, No. 3, pp. 490-498.
Knudson, M. M. et al., Thromboembolism Following Multiple Trauma, The Journal of Trauma, Jan. 1992, vol. 32, No. 1, pp. 2-11.
Knudson, M. M. et al., "Venous Thromboembolism After Trauma", Current Opinion in Critical Care, 2004, 10:539-548.
Koga, F. et al., "Deep Vein Thrombosis During Chemotherapy in a Patient With Advanced Testicular Cancer: Successful Percutaneous Thrombectomy Under Temporary Placement of Retrievable Inferior Vena Cava Filter", International Journal of Uroloty, 2001, 8:90-93.
Konya, A. et al., "New Embolization Coil Containing a Nitinol Wire Core: Preliminary in Vitro and in Vivo Experiences", Journal of Vascular and Interventional Radiology, 2001, 12:869-877.
Kozak, T.K.W. et al., "Massive Pulmonary Thromboembolism After Manipulation of an Unstable Pelvic Fracture: A Case Report and Review of the Literature", The Journal of Trauma: Injury, Infection, and Critical Care, 1995, vol. 38, pp. 366-367.
Kraimps, J. et al., "Optical Central Trapping (OPCETRA) Vena Caval Filter: Results of Experimental Studies", Journal of Vascular and Interventional Radiolory, 1992, 3:697-701.
Kreutzer J.et al., "Healing Response to the Clamshell Device for Closure of Intracardiac Defects in Humans", Catheterization and Cardiovascular Interventions, 2001, vol. 54.
Kronemyer, B., "Temporary Filter Traps Pulmonary Emboli," Orthopedics Today, p. 34, 2005.
Kudsk, K. A. et al., "Silent Deep Vein Thrombosis in Immobilized Multiple Trauma Patients", The American Journal of Surgery, Dec. 1989, vol. 158, pp. 515-519.
Kupferschmid, J.P. et al., "Case Report: Small-Bowel Obstruction From an Extruded Greenfield Filter Strut: An Unusual Late Complication", Journal of Vascular Surgery, Jul. 1992, vol. 16, No. 1, pp. 113-115.
Kurgan, A. et al., "Case Reports: Penetration of the Wall of an Abdominal Aortic Aneurysm by a Greenfield Filter Prong: A Late Complication", Journal of Vascular Surgery, Aug. 1993, vol. 18, No. 2, pp. 303-306.
Kuszyk, B. et al., "Subcutaneously Tethered Temporary Filter: Pathologic Effects in Swine", Journal of Vascular and Interventional Radiology, Nov.-Dec. 1995, Vo. 6, No. 6, pp. 895-902.
Kyrle, P. A. et al., Deep Vein Thrombosis, The Lancet, Mar. 26-Apr. 1, 2005, 365(9465):1163-1174.
Langan III, E. M. et al., "Prophylactic Inferior Vena Cava Filters in Trauma Patients at High Risk: Follow-Up Examination and Risk/Benefit Assessment", Journal of Vascular Surgery, 1999, 30:484-490.
Leach, T. A. et al., "Surgical Prophylaxis for Pulmonary Embolism", The American Surgeon, Apr. 1994, vol. 60, No. 4, pp. 292-295.
Leask, R.L. et al., "Hemodynamic Effects of Clot Entrapment in the TrapEase Inferior Vena Cava Filter", Journal of Vascular and Interventional Radiology, 2004, 15:485-490.

Leask, R.L. et al., "In Vitro Hemodynamic Evaluation of a Simon Nitinol Vena Cava Filter: Possible Explanation of IVC Occlusion", Journal of Vascular and Interventional Radiology, 2001, 12:613-618.
Lemmon, G.W. et al., "Incomplete Caval Protection Following Suprarenal Caval Filter Placement", Angiology the Journal of Vascular Diseases, Feb. 2000, vol. 51, No. 2, pp. 155-159.
Leoni, C. J. et al., "Classifying Complications of Interventional Procedures: A Survey of Practicing Radiologists", Journal of Vascular and Interventional Radiology, 2001, 12:55-59.
Letai, A., "Cancer, Coagulation, and Anticoagulation", The Oncologist, 1999, 4:443-449.
Lewis-Carey, M. B. et al., "Temporary IVC Filtration Before Patent Foramen Ovale Closure in a Patient With Paradoxic Embolism", Journal of Vascular and Interventional Radiology, 2002, 13:1275-1278.
Lidagoster, M. I. et al., Superior Vena Cava Occlusion After Filter Insertion, Journal of Vascular Surgery, Jul. 1994, vol. 20, No. 1.
Lin, J. et al., "Factors Associated With Recurrent Venous Thromboembolism in Patients With Malignant Disease", Journal of Vascular Surgery, 2003, 37:976-983.
Lin, M. et al., "Successful Retrieval of Infected Gunther Tulip IVC Filter", Journal of Vascular and Interventional Radiology, 2000, 11:1341-1343.
Lin, P. H. et al., "The Regained Referral Ground and Clinical Practice of Vena Cava Filter Placement in Vascular Surgery", The American Surgeon, Oct. 2002, vol. 68, No. 10, pp. 865-870.
Peck, K. E. et al., "Postlaparoscopic Traumatic Inferior Vena Caval Thrombosis", Heart & Lung, Jul./Aug. 1998, vol. 27, No. 4, pp. 279-281.
Pelage, J. et al., "Re: Leiomyoma Recurrence After Uterine Artery Embolization", Journal of Vascular and Interventional Radiology, Jul. 2004, vol. 15, No. 7, pp. 773-776.
Peskin, Gerald R. (ed.), Papers of the Western Surgical Association, "Directed Parathyroidectomy—Feasibility and Performance in 100 Consecutive Patients With Primary Hyperparathyroidism", Archives of Surgery, Jun. 2003, vol. 138, p. 581.
Peterson, D. A. et al., "Computed Tomographic Venography is Specific But Not Sensitive for Diagnosis of Acute Lower-Extremity Deep Venous Thrombosis in Patients With Suspected Pulmonary Embolus", Journal of Vascular Surgery, 2001, 34:798-804.
Podnos, Y. D. et al., "Complications After Laparoscopic Gastric Bypass", Archives of Surgery, Sep. 2003, 138:957-961.
Poletti, P.A. et al., "Long-Term Results of the Simon Nitinol Inferior Vena Cava Filter", Eur. Radiol., 1998, vol. 8, pp. 289-294.
Ponchon, M. et al., "Temporary Vena Caval Filtration Preliminary Clinical Experience With Removable Vena Caval Filters", Acta Clinica Belgica, 1999, vol. 54, pp. 223-228.
Porcellini, Massimo et al., "Intracardiac Migration of Nitinol TrapEase® Vena Cava Filter and Paradoxical Embolism", European Journal of Cardio-Thoracic Surgery, vol. 22, 2002, pp. 460-461.
Porter, J. M. et al., "Reporting Standards in Venous Disease: An Update", Journal of Vascular Surgery, 1995, 21:635-645.
Poster: Clinical Science: Pulmonary Disease or Dysfunctional/Mechanical Ventilation/Weaning (Adult), Critical Care Medicine, vol. 32, No. 12 (Suppl.), pp. A111-A120, 2004.
Prince et al., "Local Intravascular Effects of the Nitinol Wire Blood Clot Filter" Investigative Radiology 23:294-390 (Apr. 1988).
Prince, M. R. et al., "The Diameter of the Inferior Vena Cava and Its Implications for the Use of Vena Caval Filters", Radiology, 1983, 149:687-689.
Proctor, M. C. et al., "Assessment of Apparent Vena Caval Penetration by the Greenfield Filter", Journal of Endovascualr Surgery, 1998, 5:251-258.
Proctor, M. C., "Indications for Filter Placement", Seminars in Vascular Surgery, Sep. 2000, vol. 13, No. 3, pp. 194-198.
Putnam et al., "Placement of Bilateral Simon Nitinol Filters for an Inferior Vena Cava Duplication through a Single Groin Access" JVIR 10:431-433 (1999). cited by other.
Putterman, Daniel et al., "Aortic Pseudoaneurysm After Penetration by a Simon Nitinol Inferior Vena Cava Filter", J Vasc Interv Radiol, 2005, 16:535-538.

(56) References Cited

OTHER PUBLICATIONS

Qanadli, S. D. et al., "Pulmonary Embolism Detection: Prospective Evaluation of Dual-Section Helical CT Versus Selective Pulmonary Arteriography in 157 Patients", Radiology, 2000, 217:447-455.

Qian et al., "In Vitro and in Vivo Experimental Evaluation of a New Vena Caval Filter" JVIR 5:513-518 (1994).

Quality Improvement Guidelines for Percutaneous Inferior Vena Cava Filter Placement for the Prevention of Pulmonary Embolism (European Standards adopted and Modified by CIRSE in Cooperation With SCVIR Standards of Practice Committee), http:www.cirse.org/vena_cava_filter_crise.htm, retrieved May 17, 2002, 11 pages.

Questions and Answers: Vena Caval filters and anticoagulants, JAMA; Oct. 20, 1993; 270, 15; pp. 1867-1868.

Quirke, T. E. et al., "Inferior Vena Caval Filter Use in U.S. Trauma Centers A Practitioner Survey", The Journal of Trauma: Injury, Infection, and Critical Care, 1997, vol. 43, No. 2, pp. 333-337.

Rabkin, D. J. et al., "Nitinol Properties Affecting Uses in Interventional Radiology", Journal of Vascular and Interventional Radiology, 2000, 11:343-350.

Radke, P. W. et al., "Thrombosis in Behcet's Disease: Report of a Case Followed by a Systematic Review Using the Methodology of Evidence-Based Medicine", Journal of Thrombosis and Thrombolysis, Apr. 2001, 11 (2):137-141.

Rajan, Dheeraj K. et al., "Retrieval of the Bard Recovery Filter from the Superior Vena Cava," JVIR, Letters to the Editor, vol. 15, No. 10, Oct. 2004, pp. 1169-1171.

Raju, N. L. et al., "Case 37: Juxtacaval Fat Collection—Mimic of Lipoma in the Subdiaphragmatic Inferior Vena Cava", Radiology, 2001, 220:471-474.

Rascona, D. A. et al., "Pulmonary Embolism—Treatment vs Nontreatment", Chest, Jun. 1999, vol. 115, No. 6, p. 1755.

Ray Jr., C. E. et al., "Complications of Inferior Vena Cava Filters", Abdominal Imaging, 1996, 21:368-374.

Razavi, M. K. et al., "Chronically Occluded Inferior Venae Cavae: Endovascular Treatment", Radiology, 2000, 214:133-138.

RD Heparin Arthroplasty Group, "RD Heparin Compared With Warfarin for Prevention of Venous Thromboembolic Disease Following Total Hip or Knee Arthroplasty", The Journal of Bone and Joint Surgery, Incorporation, Aug. 1994, vol. 76-A, No. 8, pp. 1174-1185.

Reddy, K. et al., "Insertion of an Inferior Venocaval Filter in a Pregnant Woman at Risk for Pulmonary Embolism—A Challenging Management", Departments of Obstetrics and Gynaecology and Radiology, Wexham Park Hospital, Slough, UK, 2003, p. 198.

Reed, Ricahrd A., "The Use of Inferior Vena Cava Filters in Pediatric Patients for Pulmonary Embolus Prophylaxis", Cardiovascular and Interventional Radiology, 1996,19:401-405.

Reekers, J. A. et al., "Evaluation of the Retrievability of the OptEase IVC Filter in an Animal Model", Journal of Vascular and Interventional Radiology, 2004, 15:261-267.

Reekers, Jim A., "Re Current Practice of Temporary Vena Cava Filter Insertion: A Multicenter Registry", Journal of Vascular Interventional Radiology, Nov.-Dec. 2000, pp. 1363-1364.

Ricco, Jean Baptiste et al., "Percutaneous Transvenous Caval Interruption with the LGM Filter", Ann Vasc Surg, 1988,3:242-247.

Ricotta, J. J., "Regarding Recurrent Thromboembolism in Patients With Vena Caval Filters", Journal of Vascular Surgery, 2001, vol. 33, p. 657.

Riedel, M., "Acute Pulmonary Embolism 2: Treatment", Heart, Mar. 2001, 85(3):351-360.

Robinson, Jeffrey D. et al., "In Vitro Evaluation of Caval Filters", Cardiovascular and Interventionalradiology, 1988, 11 :346-351.

Robrer, M. J. et al., "Extended Indications for Placement of an Inferior Vena Cava Filter", Journal of Vascular Surgery, Jul. 1990, vol. 12, No. 1.

Rodrigues, H. L. et al., "Update of the Management of Venous Thromboembolism [16]", Rev Port Cardiol, 2002, 21(2):183-199.

Rodriguez, J. L. et al., "Early Placement of Prophylactic Vena Caval Filters in Injured Patients at High Risk for Pulmonary Embolism", The Journal of Trauma, Injury, Infection, and Critical Care, 1996, vol. 40, No. 5, pp. 797-804.

Roehm Jr., John O. F. et al., "The Bird's Nest Inferior Vena Cava Filter: Progress Report", Radiology, Sep. 1988,168:745-749.

Roehm Jr., John O. F., "The Bird's Nest Filter: A New Percutaneous Transcatheter Inferior Vena Cava Filter", Journal of Vascular Surgery, Oct. 1984, vol. 1, No. 3.

Rogers, F. B. et al., "Five-Year Follow-Up of Prophylactic Vena Cava Filters in High-Risk Trauma Patients", Archives of Surgery, Apr. 1998, 133:406-411.

Rogers, F. B. et al., "Immediate Pulmonary Embolism After Trauma: Case Report", Journal of Trauma: Injury, Infection, and Critical Care, vol. 48, No. 1, pp. 146-148, Jan. 2000.

Rogers, F. B. et al., "Practice Management Guidelines for the Prevention of Venous Thromboembolism in Trauma Patients: The EAST Practice Management Guidelines Work Group", The Journal of Trauma: Injury, Infection, and Critical Care, Jul. 2002, 53:142-164.

Rogers, F. B. et al., "Prophylactic Vena Cava Filter Insertion in Selected High-Risk Orthopaedic Trauma Patients", Journal of Orthopaedic Trauma, 1997, 11(4):267-272.

Rogers, F. B. et al., "Prophylactic Vena Cava Filter Insertion in Severely Injured Trauma Patients: Indications and Preliminary Results", The Journal of Trauma, Oct. 1993, 35(4):637-642.

Rogers, F. B. et al., "Routine Prophylactic Vena Cava Filter Insertion in Severely Injured Trauma Patients Decreases the Incidence of Pulmonary Embolism", Journal of the American College of Surgeons, Jun. 1995 180 (6):641-647.

Rogers, F. B., "Venous Thromboembolism in Trauma Patients: A Review", Surgery, Jul. 2001, vol. 130, No. 1, pp. 1-12.

Rohrer, M. J. et al., "Extended Indications for Placement of an Inferior Vena Cava Filter", Journal of Vascular Surgery, Jul. 1989, vol. 10. No. 1, pp. 44-50.

Rose, S. C. et al., "Placement of Inferior Vena Caval Filters in the Intensive Care Unit", Journal of Vascular and Interventional Radiology, 1997, 8:61-64.

Rose, S. C. et al., "Regarding "Bedside Vena Cava Filter Placement Guided With Intravascular Ultrasound"", Journal of Vascular Surgery, Apr. 2002, vol. 35, No. 4.

Rossi, G. et al., "Open to Critique: An Unusual Complication of Vena Cava Filter Placement", Journal of Vascular Surgery, Nov. 1996, vol. 24, No. 5.

Rousseau, Hervé et al., "The 6-F Nitinol TrapEase Inferior Vena Cava Filter: Results of a Prospective Multicenter Trial", J Vasc Interv Radioi, 2001,12:299-304.

Rubin, B. G. et al., "Care of Patients With Deep Venous Thrombosis in an Academic Medical Center: Limitations and Lessons", Journal of Vascular Surgery, 1994, 20:698-704.

Ruiz, A. J. et al., "Heparin, Deep Venous Thrombosis, and Trauma Patients", The American Journal of Surgery, Aug. 1991, 162:159-162.

Ryskamp, R. P. et al., "Utilization of Venous Thromboembolism Prophylaxis in a Medical-Surgical ICU", Chest, Jan. 1998, 113(1):162-164.

S. Raghavan et al., "Migration of Inferior Vena Cava Filter Into Renal Hilum", Nephron, Jun. 2002; 91, 2; Health & Medical Complete; pp. 333-335.

Salamipour et al., "Percutaneous Transfemoral Retrieval of a Partially Deployed Simon-Nitinol Filter Misplaced into the Ascending Lumbar Vein" JVIR 7:917-919 (1996).

Salamipour, H. et al., "Percutaneous Transfemoral Retrieval of a Partially Deployed Simon-Nitinol Filter Misplaced Into the Ascending Lumbar Vein", Journal of Vascular and Interventional Radiology, 1996, 7:917-919.

Sapala, J. A. et al., "Fatal Pulmonary Embolism After Bariatric Operations for Morbid Obesity: A 24-Year Retrospective Analysis", Obesity Surgery, 2003, 13:819-825.

Sarasin, F. P. et al., "Management and Prevention of Thromboemboli in Patients With Cancer-Related Hypercoagulable", Journal of General Internal Medicine, Sep. 1993, 8:476-485.

(56) References Cited

OTHER PUBLICATIONS

Savader, Scott J., Venous Interventional Radiology with Clinical Perspectives, Chapter 28: Inferior Vena Cava Filters, pp. 367-399, Apr. 2000.
Savin, M. A. et al., "Greenfield Filter Fixation in Large Vena Cavae", Journal of Vascular and Interventional Radiology, 1998, 9:75-80.
Savin, Michael A. et al., "Placement of Vena Cava Filters: Factors Affecting Technical Success and Immediate Complications", AJR, Sep. 2002, Vo. 179, pp. 597-602.
Schanzer, H. et al., "Guidewire Entrapment During Deployment of the Over-the-Guidewire Stainless Steel Greenfield Filter: A Device Design-Related Complication", Journal of Vascular Surgery, 2000, 31:607-610.
Schleich, J.-M. et al., "Long-Term Follow-up of Percutaneous Vena Cava Filters: A Prospective Study in 100 Consecutive Patients", Eur J Vasc Endovasc Surg, 2001, vol. 21, pp. 450-457.
Schultz, D. J. et al., "Incidence of Asymptomatic Pulmonary Embolism in Moderately to Severely Injured Trauma Patients", Journal of Trauma: Injury, Infection, and Critical Care, 2004, 56:727-733.
Sequeira et al., "A Safe Technique for Introduction of the Kimray-Greenfield Filter" Radiology 133:799-800 (Dec. 1979).
Shackford, S. R. et al., "Venous Thromboembolism in Patients With Major Trauma", The American Journal of Surgery, Apr. 1990, vol. 1 59, pp. 365-369.
Shaer, J. et al., "An Unusual Cause of Low Back Pain?: A Case Report", Spine, Jun. 15, 1998, 23(12):1349-1350.
Shahmanesh, Maryam et al., "Inferior Vena Cava Filters for HIV Infected Patients With Pulmonary Embolism and Contraindications to Anticoagulation", Sex Transm Inf, 2000, 76:395-397.
Sharafuddin, M. J. et al., "Endovascular Management of Venous Thrombotic and Occlusive Diseases of the Lower Extremities", Journal of Vascular and Interventional Radiology, Apr. 2003, 14:405-423.
Sharpe, R. P. et al., "Incidence and Natural History of Below-Knee Deep Venous Thrombosis in High-Risk Trauma Patients", The Journal of Trauma: Injury, Infection, and Critical Care, Dec. 2002, 53:1048-1052.
Sheikh, M. A. et al., "Images in Vascular Medicine", Vascular Medicine 2001, 6:63-64.
Sheikh, M. A. et al., "Isolated Internal Jugular Vein Thrombosis: Risk Factors and Natural History", Vascular Medicine, 2002, 7:177-179.
Shellock, F. G. et al., "MR Procedures: Biologic Effects, Safety, and Patient Care", Radiology, 2004, 232:635-652.
Siddique, R. M. et al., "Thirty-Day Case-Fatality Rates for Pulmonary Embolism in the Elderly", Archives of Internal Medicine, Nov. 11, 1996, 156:2343-2347.
Siegel and Robertson, "Percutaneous Tranfemoral Retrieval of a Free-Floating Titanium Greenfield Filter with an Amplatz Goose Neck Snare" JVIR 4:565-568 (1993).
Simon et al., "Transvenous Devices for the Management of Pulmonary Embolism", CardioVascular and Interventional Radiology, 3:308-313, 1980, pp. 112-120.

Simon Nitinol Filter Brochure, Nitinol Medical Technologies, Inc., 1995, p. 290.
Simon Nitinol Filter SNF/SL Filter Sets, C. R. Bard, Inc. PK5014851 Rev. 01 Sep. 2002 (2002).
Simon, M. et al., "Comparative Evaluation of Clinically Available Inferior Vena Cava Filters With an In Vitro Physiologic Simulation of the Vena Cava", Radiology, 1993, 189:769-774.
Simon, M. et al., "Paddle-Wheel CT Display of Pulmonary Arteries and Other Lung Structures: A New Imaging Approach", American Journal of Roentgenology, Jul. 2001, pp. 195-198.
Simon, M., "Vena Cava Filters: Prevalent Misconceptions", Journal of Vascular and Interventional Radiology, 1999, 10:1021-1024.
Simon, Morris et al., "Simon Nitinol Inferior Vena Cava Filter: Initial Clinical Experience", Radiology, vol. 172, No. 1, DO 99-103, Jul. 1989.
Simon,M. et al., "A Vena Cava Filter Using Thermal Shape Memory Alloy", Radiology, Oct. 1977, 125:89-94.
Sing, R. F. et al., "Bedside Carbon Dioxide (CO2) Preinsertion Cavagram for Inferior Vena Cava Filter Placement: Case Report", Journal of Trauma, Dec. 1999, 47(6):1140-1142.
Sing, R. F. et al., "Bedside Carbon Dioxide Cavagrams for Inferior Vena Cava Filters: Preliminary Results", Journal of Vascular Surgery, 2000, 32:144-147.
Sing, R. F. et al., "Bedside Insertion of Inferior Vena Cava Filters in the Intensive Care Unit", Journal of American College of Surgeons, May 2001, 192(5):570-575.
Sing, R. F. et al., "Bedside Insertion of Inferior Vena Cava Filters in the Intensive Care Unit", Journal of Trauma, Dec. 1999, 47(6):1104-1109.
Sing, R. F. et al., "Bedside Insertion of the Inferior Vena Cava Filter in the Intensive Care Unit", The American Surgeon, Aug. 2003, 69:660-662.
Sing, R. F. et al., "Guidewire Incidents With Inferior Vena Cava Filters", JAOA, Apr. 2001, 101(4):231-233.
Sing, R. F. et al., "Preliminary Results of Bedside Inferior Vena Cava Filter Placement", Chest, Jul. 1998, 114(1):315.
Sing, R. F. et al., "Regarding Bedside Vena Cava Filter Placement Guided With Intravascular Ultrasound", Journal of Vascular Surgery, May 2002, vol. 25, No. 5.
Sing, Ronald F., "Safety and Accuracy of Bedside Carbon Dioxide Cavography for Insertion of Inferior Vena Cava Filters in the Intensive Care Unit", American Coiiege of Surgeons, Feb. 2, 2001, vol. 192, pp. 168-171.
Smith, T. P. et al., "Acute Pulmonary Thromboembolism—Comparison of the Diagnostic Capabilities of Convention Film-Screen and Digital Angiography", Chest, 2002, 122:968-972.
Smith, T. P., "Pulmonary embolism: What's Wrong With This Diagnosis?", American Journal of Roentgenology, Jun. 2000, 174:1489-1498.
Spain, D. A. et al., "Venous Thromboembolism in the High-Risk Trauma Patient: Do Risks Justify Aggressive Screening and Prophylaxis?", The Journal of Trauma: Injury, Infection, and Critical Care, 1997, vol. 42, No. 3, pp. 463-469.
Spence, Liam D. et al., "Acute Upper Extremity Deep Venous Thrombosis, Safety and Effectiveness of Superior Vena Caval Filters", Radiology, Jan. 1999, vol. 210, DO 53-58.

* cited by examiner

REMOVABLE EMBOLUS BLOOD CLOT FILTER

PRIORITY DATA AND INCORPORATION BY REFERENCE

This application is a continuation of U.S. patent application Ser. No. 13/170,054, filed Jun. 27, 2011, now U.S. Pat. No. 8,574,261, which is a continuation of U.S. patent application Ser. No. 11/429,975, filed May 9, 2006, now U.S. Pat. No. 7,967,838, which claims the benefit of priority to U.S. Provisional Patent Application No. 60/680,601, filed May 12, 2005, each of which is incorporated by reference in its entirety into this application.

FIELD OF THE INVENTION

This invention relates to a filter device that can be placed in a blood vessel to reduce the risk of embolisms and, if needed, removed from the blood vessel without causing traumatic damage to the blood vessel.

BACKGROUND OF THE INVENTION

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein, such as the vena cava. These vena cava filters are designed to remain in place permanently. Such filters include structure to anchor the filter in place within the vena cava, such as elongate diverging anchor members with hooked ends that penetrate the vessel wall and positively prevent migration in either direction longitudinally of the vessel. The hooks on filters of this type are rigid and will not bend, and within two to six weeks after a filter of this type has been implanted, the endothelium layer grows over the diverging anchor members and positively locks the hooks in place. Now any attempt to remove the filter results in a risk of injury to or rupture of the vena cava.

A number of conditions and medical procedures subject the patient to a short term risk of pulmonary embolism which can be alleviated by a filter implant. In such cases, patients are often averse to receiving a permanent implant, for the risk of pulmonary embolism may disappear after a period of several weeks or months. However, most existing filters are not easily or safely removable after they have remained in place for more than several weeks, and consequently longer-term temporary filters that do not result in the likelihood of injury to the vessel wall upon removal are not available.

In an attempt to provide a removable filter, two filter baskets have been formed along a central shaft that are conical in configuration, with each basket being formed by spaced struts radiating outwardly from a central hub for the basket. The central hubs are held apart by a compression unit, and the locator members of the two baskets overlap so that the baskets face one another. Filters of this type require the use of two removal devices inserted at each end of the filter to draw the baskets apart and fracture the compression unit. The end sections of the locator members are formed to lie in substantially parallel relationship to the vessel wall and the tips are inclined inwardly to preclude vessel wall penetration. If a device of this type is withdrawn before the endothelium layer grows over the locator members, vessel wall damage is minimized. However, after growth of the endothelium layer the combined inward and longitudinal movement of the filter sections as they are drawn apart can tear this layer.

SUMMARY OF THE INVENTION

The various embodiments provide for a removable blood filter that allows for filtering of an embolus in a blood vessel by utilizing a plurality of locators and a plurality of anchors. In one aspect, a filter to be placed in a flow of blood through a vessel includes a hub, at least one anchor, and at least one locator. The hub can be disposed along a longitudinal axis. The at least one anchor projects from the hub and includes a hook that penetrates a wall of the blood vessel when the filter is placed in the blood vessel. The hook can be spaced along the longitudinal axis from the hub and spaced a first radial distance from longitudinal axis. The at least one locator has a tip or portion of the locator that engages the wall of the vessel. The tip can be spaced along the longitudinal axis from the hub and spaced a second radial distance from the longitudinal axis. The second radial distance can be less than the first radial distance. The at least one locator has at least four portions and each of the portions can be disposed on respective distinct axes.

In yet another aspect, the various embodiments also provide for a filter to be placed in a flow of blood through a vessel. The filter includes a hub, at least one anchor, and at least one locator. The hub can be disposed along a longitudinal axis. The at least one anchor projects from the hub and includes a hook that penetrates a wall of the blood vessel when the filter is placed in the blood vessel. The hook can be spaced along the longitudinal axis from the hub and spaced a first radial distance from the longitudinal axis. The at least one locator projects from the hub and has a tip or portion of the locator that engages the wall of the vessel. The tip can be spaced along the longitudinal axis from the hub and spaced a second radial distance from the longitudinal axis where the second radial distance can be less than the first radial distance. The locator can be disposed proximate the hub and has at least four portions, and each of the at least four portions can be disposed on respective distinct axes. The at least four portions can include a curved portion being disposed on a radius of curvature that extends along the longitudinal axis.

In yet a further aspect of the various embodiments, a filter is provided to be placed in a flow of blood through a vessel. The filter includes a hub, at least one anchor and at least one locator. The hub can be disposed along a longitudinal axis. The at least one anchor projects from the hub and includes a hook that penetrates a wall of the blood vessel when the filter is placed in the blood vessel, spaced along the longitudinal axis from the hub, and spaced a first radial distance from longitudinal axis. The at least one locator projects from the hub and has a tip or portion of the locator that engages the wall of the vessel. The tip can be spaced along the longitudinal axis from the hub, and spaced a second radial distance from the longitudinal axis, where the second radial distance can be less than the first radial distance. The locator has a first portion distal to the hub and a second portion proximal to the hub. Each of the first and second portions can be generally linear and disposed on distinct axes oblique with respect to the longitudinal axis, where the length of the first portion can be greater than a length of the second portion.

In yet an additional aspect of the various embodiments, a filter is provided to be placed in a flow of blood through a vessel. The filter includes a hub, at least one anchor and at least one locator. The hub can be disposed along a longitudinal axis. The at least one anchor projects from the hub and includes a hook that penetrates a wall of the blood vessel, spaced along the longitudinal axis from the hub, and spaced a first radial distance from the longitudinal axis. The at least one locator projects from the hub and has a tip or portion of the locator that engages the wall of the vessel. The tip can be spaced along the longitudinal axis from the hub, and spaced a second radial distance from the longitudinal axis, where the second radial distance can be less than the first radial distance. The locator has first and second portions oblique to the longitudinal axis. The first portion can be distal to the hub, and a second portion can be proximal to the hub, where a length of the first portion being greater than a length of the second portion.

In yet another aspect of the various embodiments, a filter is provided to be placed in a blood vessel that includes a blood vessel wall. The filter includes a hub, and a first and a second set of members. The hub can be disposed along a longitudinal axis. Each of the first set of members extends from the hub. Each of the first set of members includes a hook spaced along the longitudinal axis from the hub, each hook being spaced radially from the longitudinal axis a first distance. Each of the second set of members extends from the hub and includes a tip being spaced along the longitudinal axis from the hub. Each tip can be spaced radially from the longitudinal axis a second distance less than the first distance.

In yet a further aspect of the various embodiments, a filter to be placed in a blood vessel is provided. The filter includes a hub, a plurality of anchors and a plurality of locators. The hub can be disposed along a longitudinal axis. The plurality of anchors branches from the hub. Each anchor includes a hook that: (i) penetrates a wall of the blood vessel, (ii) can be spaced along the longitudinal axis from the hub, and (iii) can be radially spaced from the longitudinal axis a first distance. The plurality of locators branches from the hub. Each locator includes a base portion proximate the hub, a first portion that extends from the base portion and along a first axis, a second portion that extends from the first portion and along a second axis, which can be distinct from the first axis, and a tip portion that extends from the second portion and along a tip axis, which can be distinct from the first and second axes. The tip portion (i) engages the wall of the blood vessel, (ii) can be spaced along the longitudinal axis from the hub, and (iii) can be radially spaced from the longitudinal axis a second distance, which can be less than the first radial distance.

In yet a further aspect of the various embodiments, a filter to be placed in a blood vessel is provided. The filter includes a hub, a plurality of anchors and a plurality of locators. The hub can be disposed along a longitudinal axis. The plurality of anchors branches from the hub. Each anchor includes a hook that: (i) penetrates a wall of the blood vessel, (ii) can be spaced along the longitudinal axis from the hub, and (iii) can be radially spaced from the longitudinal axis a first distance. The plurality of locators branches from the hub. Each locator includes a base portion proximate the hub, a tip portion that (i) can engage the wall of the blood vessel, (ii) can be spaced along the longitudinal axis from the hub, and (iii) can be radially spaced from the longitudinal axis a second distance, which can be less than the first radial distance, and an intermediate portion coupling the base and tip portion. The intermediate portion can include a first linear segment extending from the base portion a first length along a first axis, which can be oblique with respect to the longitudinal axis and a second linear segment extending between the tip portion and first portions a second length, which can be greater than the first length, and along a second axis, which can be oblique respect to the longitudinal axis and can be distinct from the first axis.

In yet another aspect of the various embodiments, a filter is provided. The filter is to be placed in a flow of blood contained by a wall of a blood vessel. The filter includes a hub that extends along a longitudinal axis and at least one first member having first and second generally linear segments. The filter also includes at least one second member having third and fourth generally linear segments. The first segment defines a portion of a first cone when the first segment is rotated about the longitudinal axis. The second segment defines a cylinder when the second segment is rotated about the longitudinal axis. The third and fourth segments define respective portions of a third and fourth cones when each of the segments is rotated about the longitudinal axis. At least one of the third and fourth segments has a hook portion that penetrates the wall of a blood vessel.

In yet a further aspect of the various embodiments, a blood filter is provided to be placed in a flow of blood contained by a wall of a blood vessel. The filter includes a hub, at least one anchor and a plurality of locators. The hub can be disposed along a longitudinal axis extending generally parallel to the flow of blood. The at least one anchor includes a hook that penetrates the wall of the vessel. The at least one anchor defines a generator of a first conical shape about a longitudinal axis. The first conical shape includes: (i) an apex disposed proximate the hub, each anchor (ii) can be spaced along the longitudinal axis from the hub, and (iii) can be radially spaced from the longitudinal axis at a first distance. The plurality of locators branches from the hub and defines a first frustum having a geometric centroid along the longitudinal axis.

In yet another aspect, a filter is provided. The filter can be placed in a flow of blood contained by a wall of a blood vessel. The filter includes a hub, a plurality of anchors, and a plurality of locators. The hub can be disposed along a longitudinal axis. The plurality of anchors branches from the hub. Each anchor can include a hook that (i) penetrates a wall of the blood vessel, (ii) can be spaced along the longitudinal axis from the hub, and (iii) can be radially spaced from the longitudinal axis a first distance. The plurality of locators branches from the hub. Each locator includes a base portion extending arcuately from the hub. The base portion has a radius of curvature about a transverse axis located at a second distance generally radially from the longitudinal axis. Each of the locators has a tip contiguous to the wall of the vessel. A portion of the tip closest to the hub can be spaced at a third distance along the longitudinal axis from the hub and spaced a fourth radial distance from the longitudinal axis, the fourth radial distance being less than the third distance.

The various embodiments described above may further include a radio-opaque material on or as part of the filter hub. Also, the various embodiments described above may further include a bio-active agent incorporated with or as part of the filter.

The various embodiments further provide a method of centering a blood filtering device within a blood vessel having a plurality of locators extending from a hub to define a first volume and a plurality of anchors extending from the hub to define a second volume. The method can be achieved by enclosing more than 15 percent of the second volume in the first volume, and engaging a hook provided on each locator onto a wall of the blood vessel.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

DETAILED DESCRIPTION OF THE PREFERRED EMBODIMENTS

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

Figure 1:
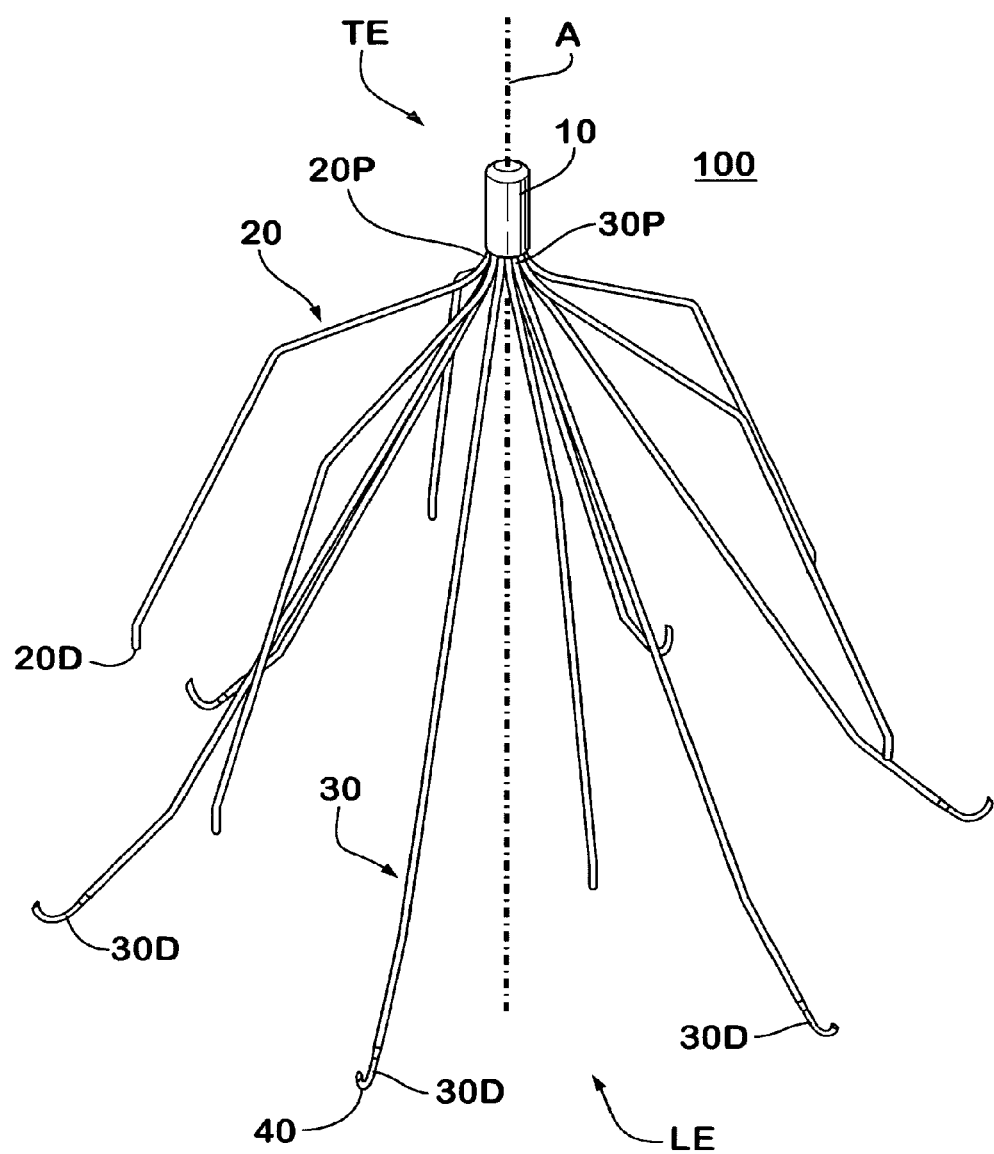
FIG. 1 is a top down perspective view of a preferred embodiment of the blood filter.
Figure 2:
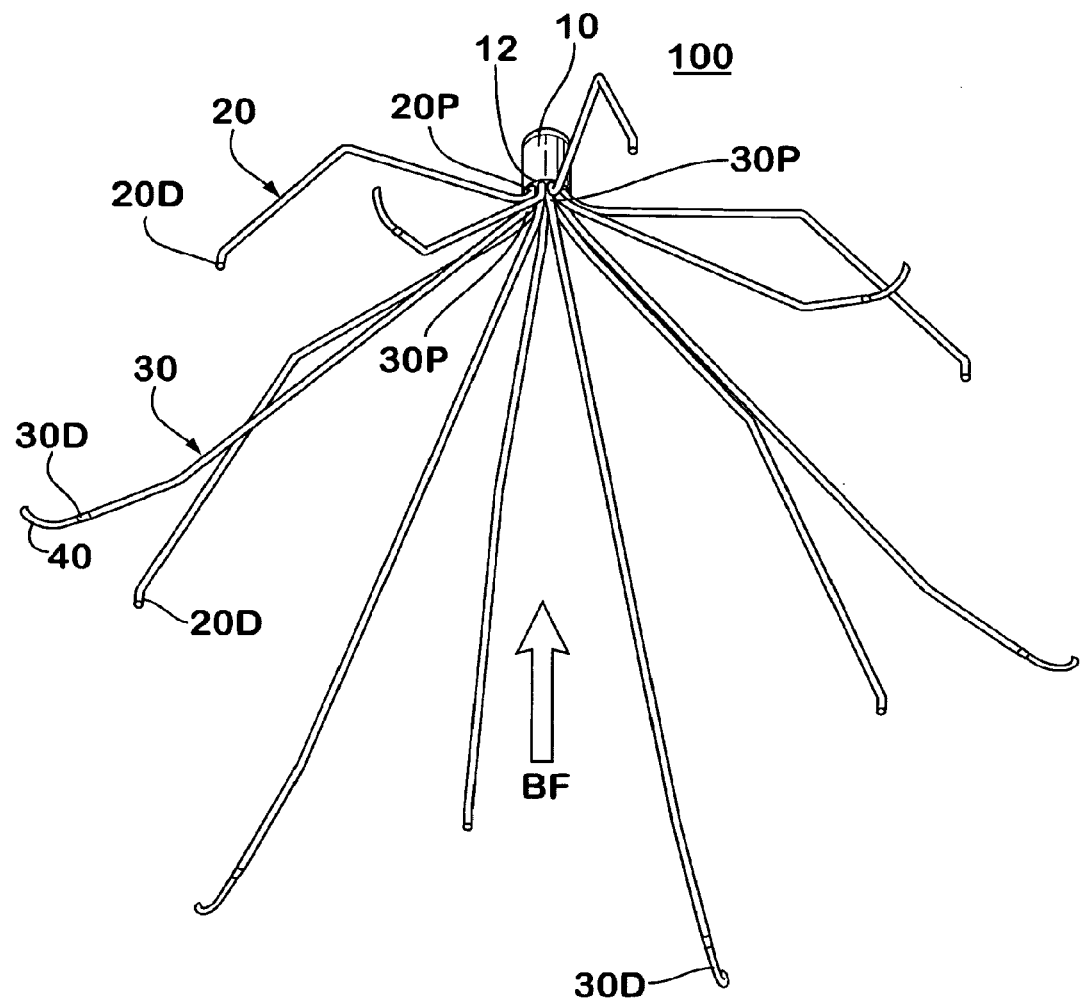
FIG. 2 is a bottom up perspective view of the embodiment of FIG. 1.

FIGS. 1-14 illustrate the preferred embodiments. Referring to FIG. 1, a filter 100 is illustrated in a perspective view. The filter 100 includes a hub 10, locator member 20, and anchor member 30 that has a hook 40. The filter 100 can be made from a plurality of elongate wires, which are preferably metal, such as, for example, Elgiloy, and more preferably are a super elastic shape memory alloy, such as Nitinol. The wires are held together at the filter trailing end by a hub 10 by a suitable connection technique, such as, for example, welding, laser welding, or plasma welding or being bonded together. Preferably, the wires are plasma welded. As used herein, "wire" refers to any elongated member of narrow cross section, including rods, bars, tubes, wire and narrow sections cut from thin plate, and is not intended to limit the scope of the invention to elongated members of circular cross section, cut from wire stock or manufacture according to a particular method of metal forming.

Figure 6:
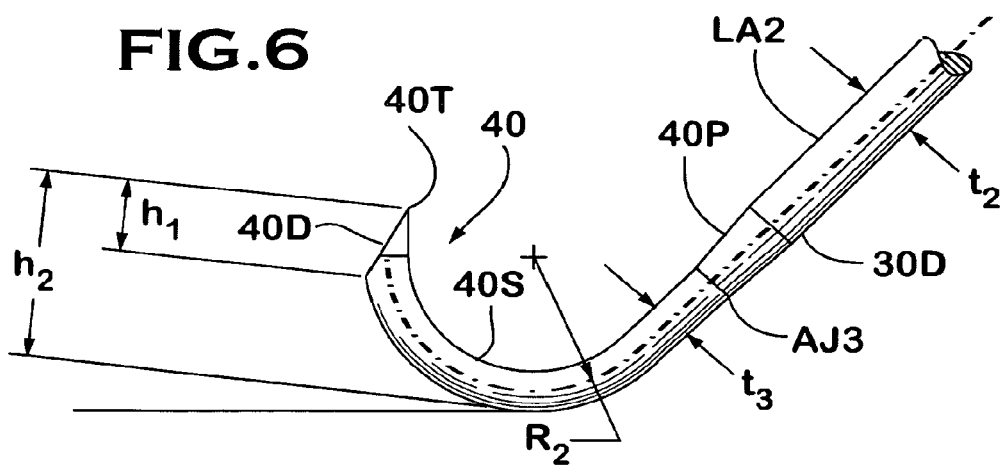
FIG. 6 is a close up side view of a hook of the anchor member for the filter of FIG. 1.

The locator member 20 has a proximal locator end 20P and a distal locator end 20D. Similarly, the anchor member 30 has a proximal anchor end 30P and a distal anchor end 30D. The distal anchor end 30D can be provided, as shown in FIG. 6, with hook 40.

Figure 4A:
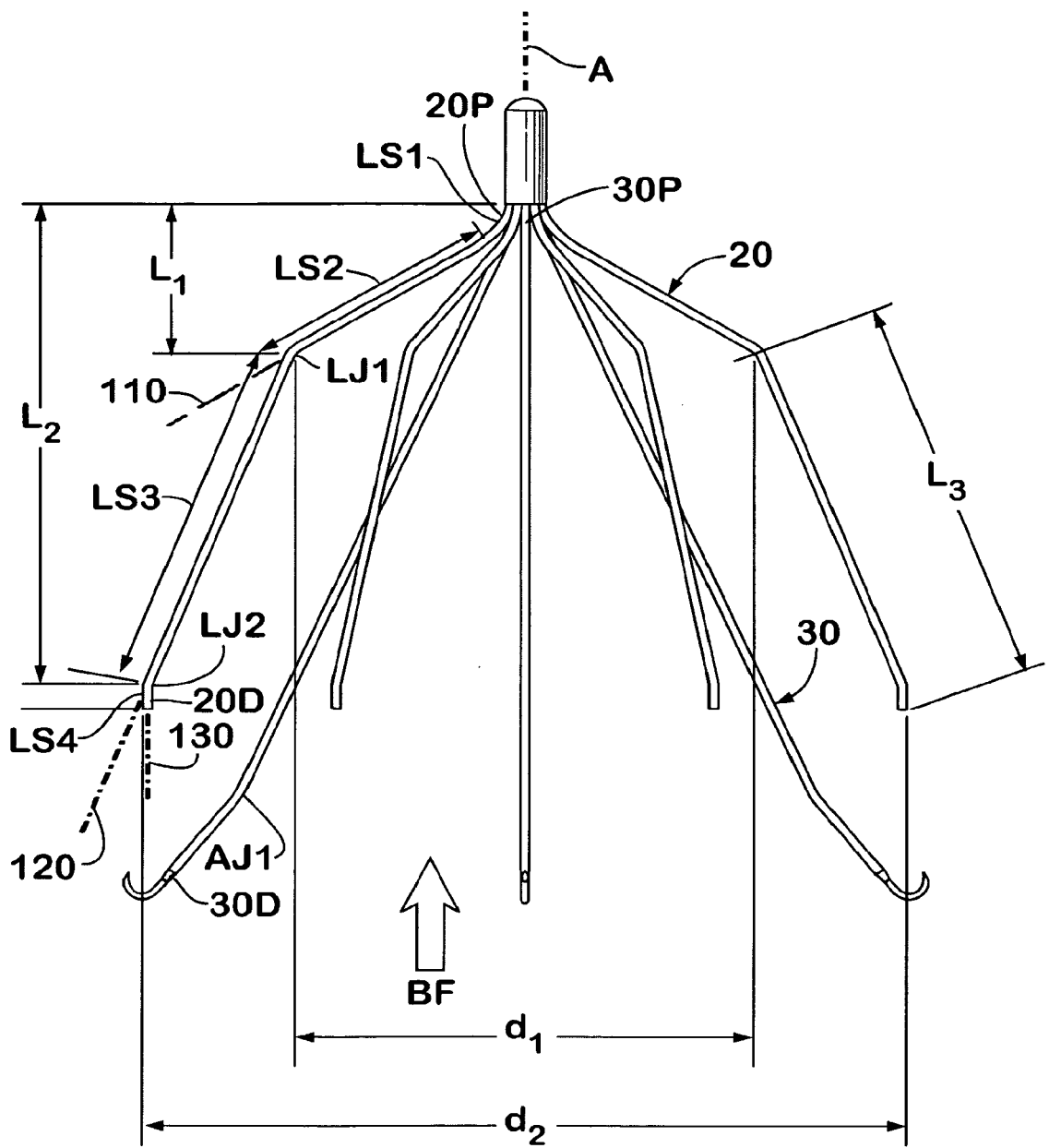
FIG. 4A is a side view of the filter viewed along view 4A-4A in FIG. 3.
Figure 4B:
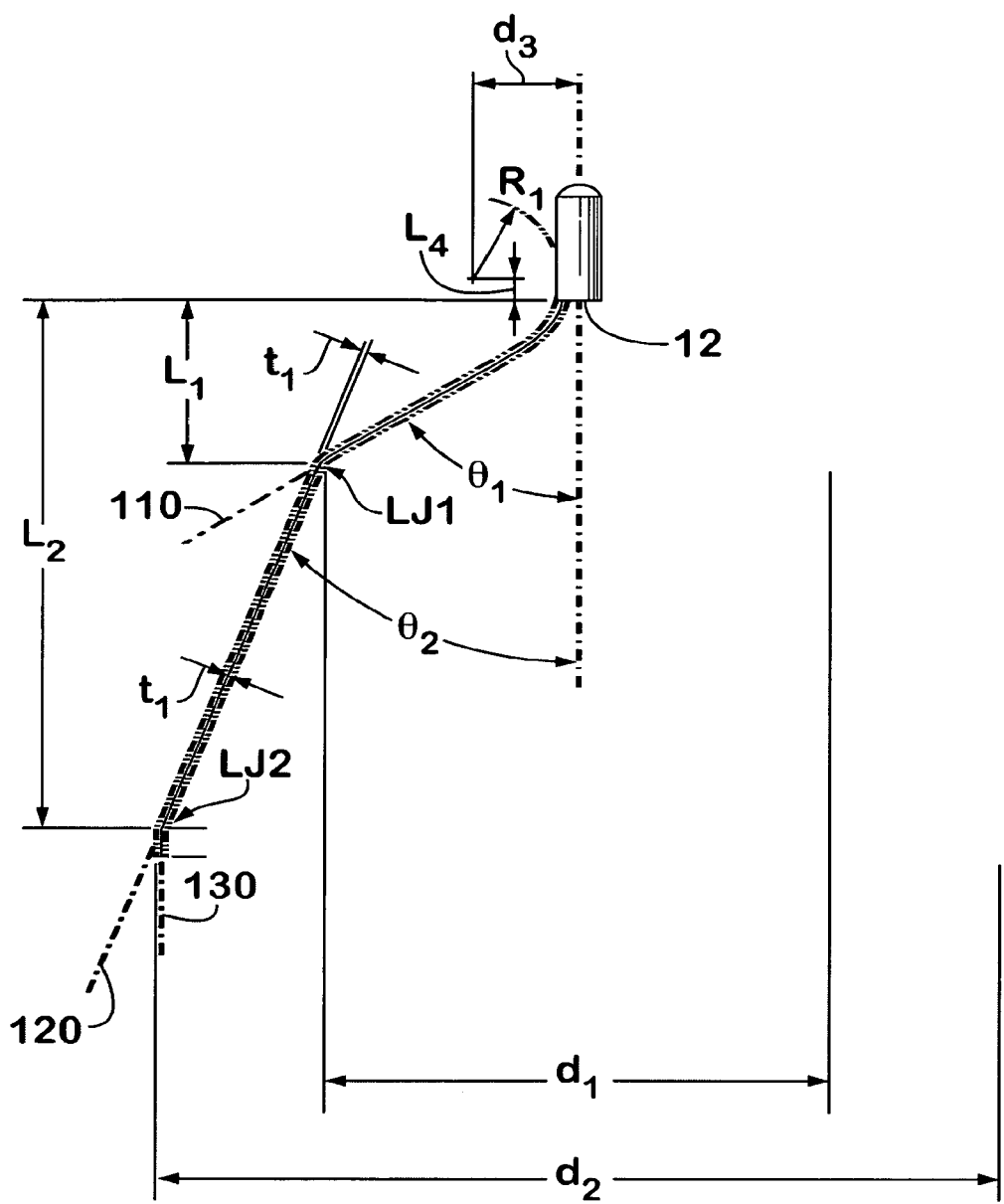
FIG. 4B is a side view of one arm or locator member of the filter of FIG. 1.

Referring to FIGS. 4A and 4B, the locator member 30 may be provided with a plurality of locator segments, preferably between 3 and 6 segments and more preferably four locator segments LS1, LS2, LS3, LS4. First locator segment LS1 may be a curved portion extending away from the hub in a first direction along the longitudinal axis A. In an embodiment, the second locator segment LS2 extends generally linearly along a second axis 110; third locator segment LS3 extends generally linearly along a third axis 120; and the fourth locator segment LS4 extends generally linearly along a fourth axis 130. In a preferred embodiment, the various axes A, 110, 120, 130, and 140 are distinct from one another in that each may intersect with one another but none of them are substantially collinear with each other.

The locator segment LS2 may be distinct from locator segment LS3 by virtue of a joint or bend LJ1. The locator segment LS3 may be distinct from locator segment LS4 via a join or bend LJ2. The joint or bend LJ1 or LJ2 can be viewed as a location formed by the intersection of the segments defining a radiused portion connecting any two segments.

The locators 20 may range from 3 to 12 locators. The filter embodiment illustrated in FIG. 4A includes six locators that are generally equiangularly spaced about axis A. In the embodiment illustrated in FIG. 4B, locator segment LS1 extends through an arc with a radius of curvature R1 whose center may be located along an axis orthogonal to axis A over a radially transverse distance $d_3$ and over a longitudinal distance $L_4$ as measured from a terminal surface 12 of the hub 10 along an axis generally parallel to the longitudinal axis A. The locator segment LS2 extends along axis 110 to form a first angle $\theta_1$ with respect to the longitudinal axis A whereas the locator segment LS3 extends along axis 120 to form second angle $\theta_2$. As shown in FIG. 4B, the first locator joint or bend LJ1 may be located at a longitudinal length L1 generally parallel to axis A from the terminal surface 12. The first locator joint or bend LJ1 may be also located at a distance of about one-half distance "$d_1$" from axis A on a generally orthogonal axis with respect to axis A as shown in FIG. 4A, where the distance $d_1$ is the distance between inside facing surfaces of respective diametrically disposed locators 20. The second locator joint LJ2 may be located over a longitudinal length $L_2$ generally parallel to axis A. The second locator join LJ2 may be located over a distance of about one-half diameter "$d_2$" from axis A. The distance $d_2$ is the distance between the outermost surface of the fourth segment LS4 of respective diametrically disposed locators 20. The thickness of locator member 20 is $t_1$. Where the locator member 20 is a wire of circular cross-section, the thickness $t_1$ of the locator 20 may be the diameter of the wire.

A range of values may be used for the aforementioned dimensional parameters in order to provide locator members that will locate the filter within the vein or vessel in which the filter is to be applied in a manner that positions segment LS4 approximately parallel to the walls of the vein or vessel and provides sufficient lateral force against the vein or vessel wall to center the filter but not so much force as to cause injury to the wall. For example, a filter intended to be placed in a narrow vein or vessel, such as a human infant or canine vena cava, may have smaller dimensions $L_1$, $L_2$, $L_3$, $L_4$, LS1, LS2, LS3, LS4, $d_1$ and $d_2$ so that the positioning members can deploy sufficiently to accomplish the positioning and filtering functions, than a filter intended to be placed in a large vein or vessel, such as an adult human vena cava or other vessel. In an example embodiment suitable for an adult human vena cava filter, when the filter is at the temperature of the subject and unconstrained, the radius of curvature $R_1$ is from about 0.02 inches to about 0.1 inches with the center of the radius $R_1$ being located over a distance $d_3$ from the axis A of about 0.1 inches and length $L_4$ of about 0.2 inches; the length $L_1$ is about 0.3 inches; length $L_2$ is about 0.9 inches; distance $d_1$ (as measured to the inside facing surfaces of diametrically disposed locators 20) is about 0.8 inches; distance $d_2$ is about 1.5 inches, the first angle $\theta_1$ is about 58 degrees, the second angle $\theta_2$ is about 20 degrees or about 22 degrees; and the thickness $t_1$ of the locator is about 0.013 inches. It should be noted that the values given herein are approximate, representing a dimension within a range of suitable dimensions for the particular embodiment illustrated in the figures, and that any suitable values can be used as long as the values allow the filter to function as intended in a blood vessel of a subject.

Figure 5A:
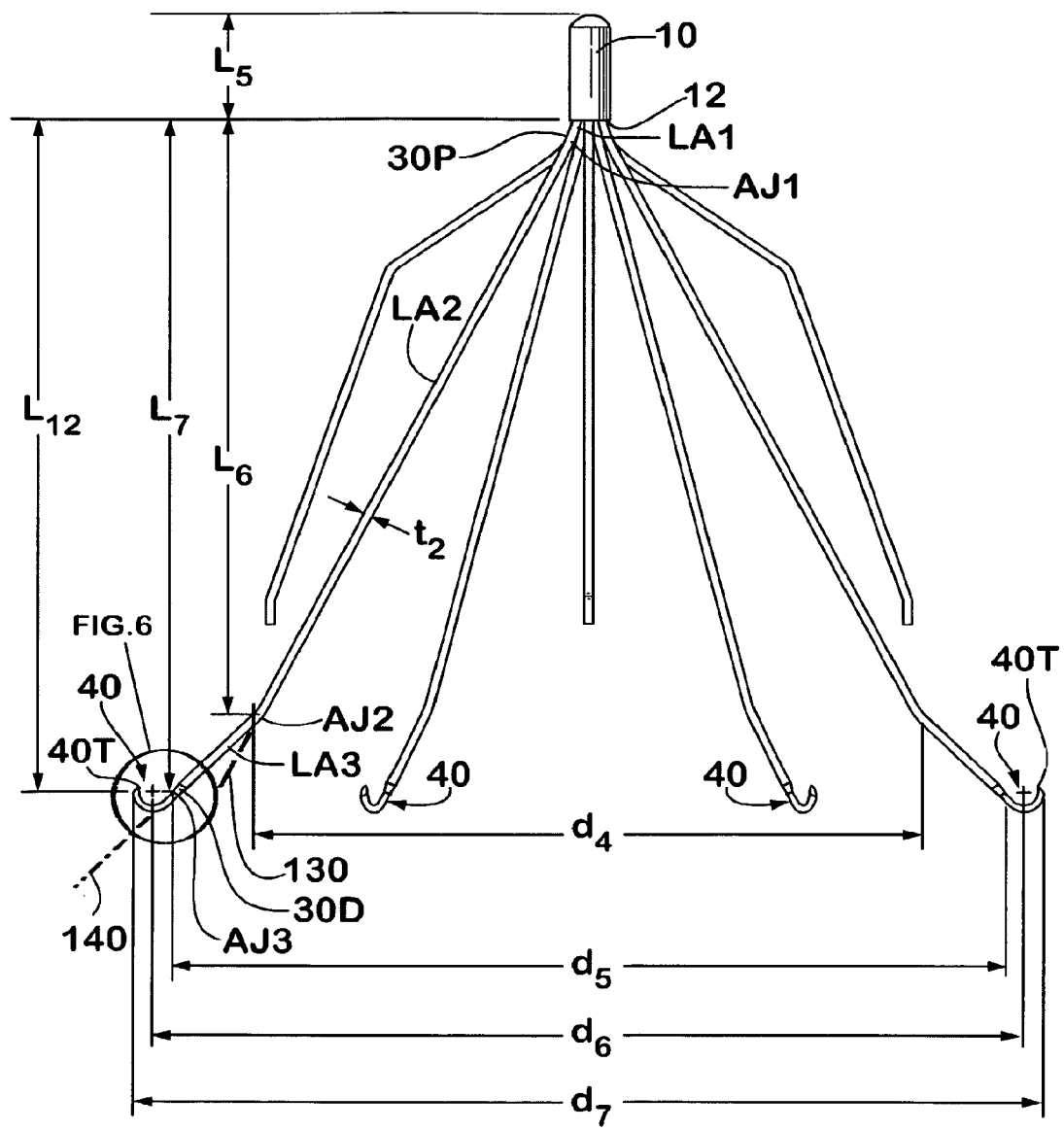
FIG. 5A is a side view of the filter viewed along view 5A-5A in FIG. 3.
Figure 5B:
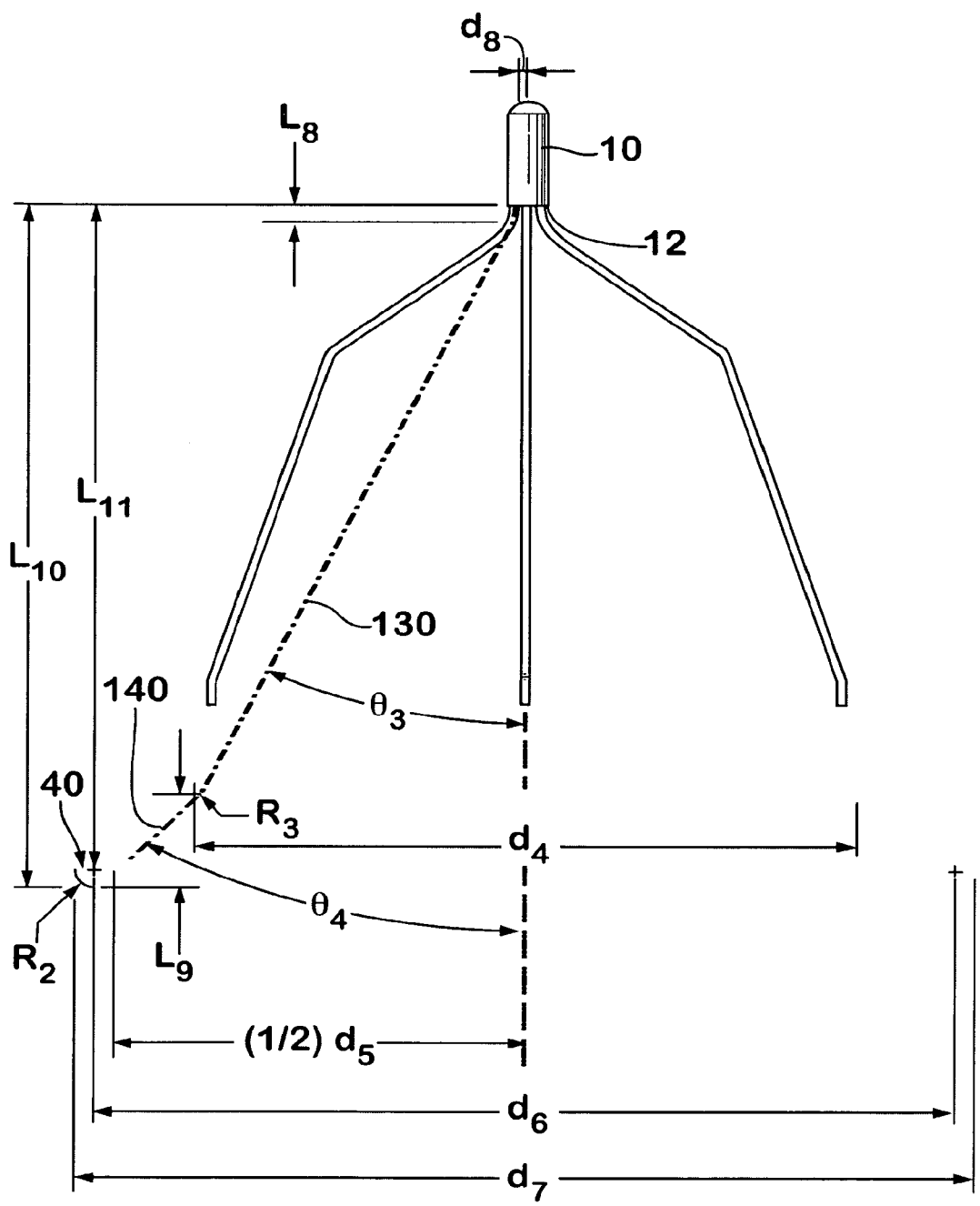
FIG. 5B is a side view of one locator member of the filter of FIG. 1.
Figure 5C:
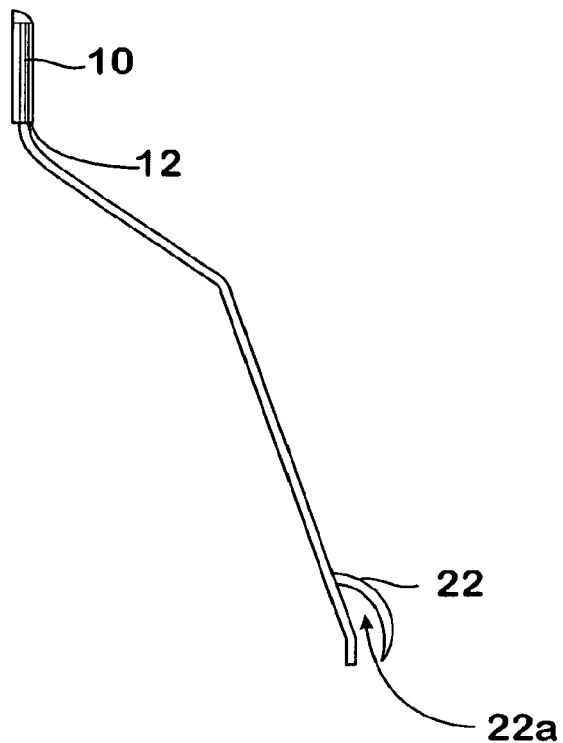
FIG. 5C is a side view of an alternative locator arrangement having a retention member disposed on the locator.

Referring to FIGS. 5A and 5B, the hub 10 can be provided with an internal cylindrical opening with a diameter of about two times the distance $d_8$. Each of the plurality of anchor members 30 can be provided with a first anchor segment LA1, a portion of which is disposed within the hub 10, connected to a second anchor segment LA2 by a first anchor joint or bend AJ1, which can be connected to a third anchor segment LA3 via a second anchor joint or bend AJ2. The third anchor segment LA3 can be connected to the hook 40 via third anchor joint or bend AJ3. The first anchor segment LA1 extends obliquely with respect to axis A. The second anchor segment LA2 extends along axis 130 oblique with respect to the axis A over an angle $\theta_3$ with respect to the longitudinal axis A. The third anchor segment LA3 extends along axis 140 oblique with respect to the longitudinal axis A over an angle $\theta_4$. The second anchor joint or bend AJ2 can be located at a sixth longitudinal distance $L_6$ as measured on an axis generally parallel to the axis A from the terminal surface 12 of the hub 10 and at about one half the fourth distance $d_4$ as measured between generally diametrical end points of two anchors 30 on an axis generally orthogonal to the axis A. The third anchor joint AJ3 can be located at a seventh longitudinal distance $L_7$ as measured along an axis generally parallel to axis A and at a transverse distance of about one-half distance $d_7$ as measured on an axis orthogonal to the axis A between the inner surfaces of two generally diametric anchors 30. The thickness of anchor member 30 is nominally $t_2$. Where the anchor member 30 is a wire of circular cross-section, the thickness $t_2$ of the anchor 30 may be the diameter of the wire. As shown in FIG. 5B, the hook 40 may be contiguous to a plane located at a longitudinal distance of $L_{10}$ as measured to the terminal surface 12 of hub 10. The hook 40 can be characterized by a radius of curvature $R_2$, in its expanded configuration at a suitable temperature, e.g., room temperature or the internal temperature of a subject. The center of the hook curvature $R_2$ can be located at a distance $L_{11}$ as measured along an axis generally parallel to the axis A from the terminal surface 12 of hub 10 and at one-half distance $d_6$ as measured between two generally diametrical hooks 40. The tips 40T of respective diametric hooks 40 may be located at longitudinal distance $L_{12}$ (which may be approximately the same as longitudinal distance $L_7$ to the third anchor joint AJ3) and at one half of distance $d_7$ between diametric hooks 40.

A range of values may be used for the aforementioned dimensional parameters in order to provide anchor members that will locate and anchor the filter within the vein or vessel in which the filter is to be applied in a manner that positions hooks 40 in contact with the walls of the vein or vessel and provides sufficient lateral force against the vein or vessel wall to ensure the hooks engage the wall but not so much force as to cause injury to the wall. For example, a filter intended to be placed in a narrow vein or vessel, such as a child or dog vena cava, may have smaller dimensions so that the anchor members can deploy sufficiently to accomplish the positioning, anchoring and filtering functions, than a filter intended to be placed in a large vein or vessels, such as an adult vena cava or other vessel. In an example embodiment suitable for an adult human vena cava filter, when the filter is at the temperature of the subject and unconstrained, the longitudinal distance $L_8$ is about 0.02 inches; $L_9$ is about 0.2 inches; $L_{10}$ is about 1.3 inches; $L_{11}$ is about 1.2 inches; $d_6$ is about 1.5 inches; $d_7$ is about 1.6 inches; $d_8$ is about 0.01 inches; $d_9$ is between 1.5 and 1.6 inches; $L_{12}$ is about 1.2 inches; the radius of curvature $R_2$ is about 0.03 inches; and the thickness $t_2$ of the anchor member is about 0.013 inches. Most preferably, a very small radius of curvature $R_3$ can characterize anchor joint or bend AJ2 where $R_3$ can be about 0.01 inches.

Figure 5D:
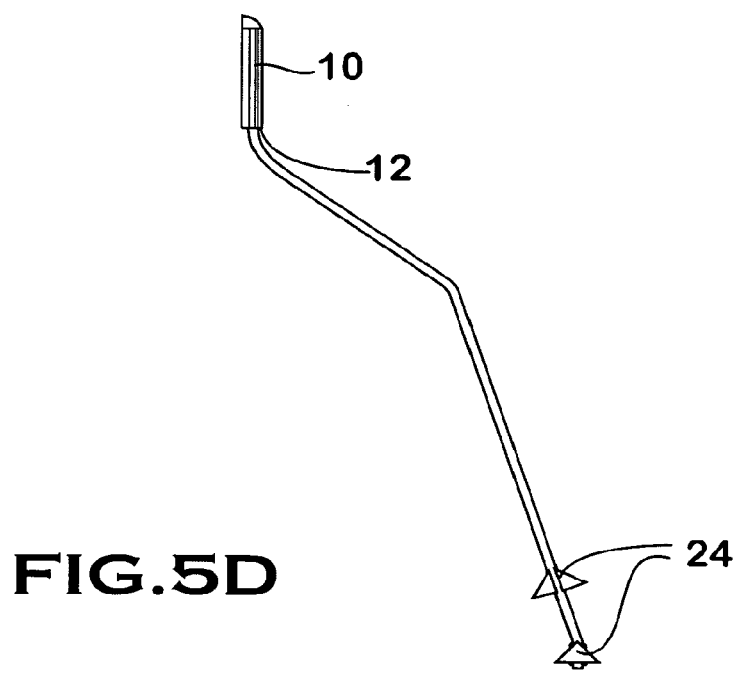
FIG. 5D is a side view of another locator arrangement having a support member to reduce or prevent penetration of a blood vessel wall by the locator.

In situations where additional retention of the filter may be desired, an anchor member can be coupled to the locator. One arrangement is shown exemplarily in FIG. 5C, where a hook 22 can be coupled to the locator proximate the tip portion. In this arrangement, both the tip portion and hook 22 are configured so that the locator does not penetrate through the blood vessel wall by formation of a stop region 22a defined by both the locator tip and the hook 22. Another arrangement can be by coupling or forming a hook in the same configuration as hook 40 for the anchor members. In yet another arrangement, shown here in FIG. 5D, where it may not be desirable to utilize a hook, one or more stop members 24 can be provided on the locator at any suitable locations. As shown in FIG. 5D, the stop member 24 is in the form of a truncated cone coupled to the locator. However, the stop member 24 can be of any configuration as long as the member 24 reduces or prevents penetration of the locator through the blood vessel wall. And in yet a further arrangement, the hook 22 (or hook 40) can be utilized in combination with the stop member 24 such as for example, a hook 22 coupled to a first locator, a hook 40 coupled to a second locator, a stop member 24 on a third locator, a combination of hook 22 and stop member 24 on a fourth locator, a combination of hook 40 and stop member 24 on a fifth locator.

Referring to FIG. 6, the hook 40 can be provided with a proximal hook portion 40P and a distal hook portion 40D on which a sharpened tip 40T is provided. The hook 40 can be formed to have a thickness $t_3$. Where the hook 40 is formed from a wire having a generally circular cross-section, the thickness $t_3$ may be generally equal to the outside diameter of the wire. In an embodiment, the hook thickness $t_3$ is approximately 0.5 to approximately 0.8 that of the anchor thickness $t_2$. The wire can be configured to follow a radius of curvature $R_2$ whose center is located at longitudinal distance $L_{11}$ and radial distance $d_9$ when the filter is at the temperature of a subject, as discussed above. The tip 40T can be provided with a generally planar surface 40D whose length can be approximately equal to length $h_1$. The tip 40T may be located over a distance $h_2$ from a plane tangential to the curved portion 40S.

Figure 7:
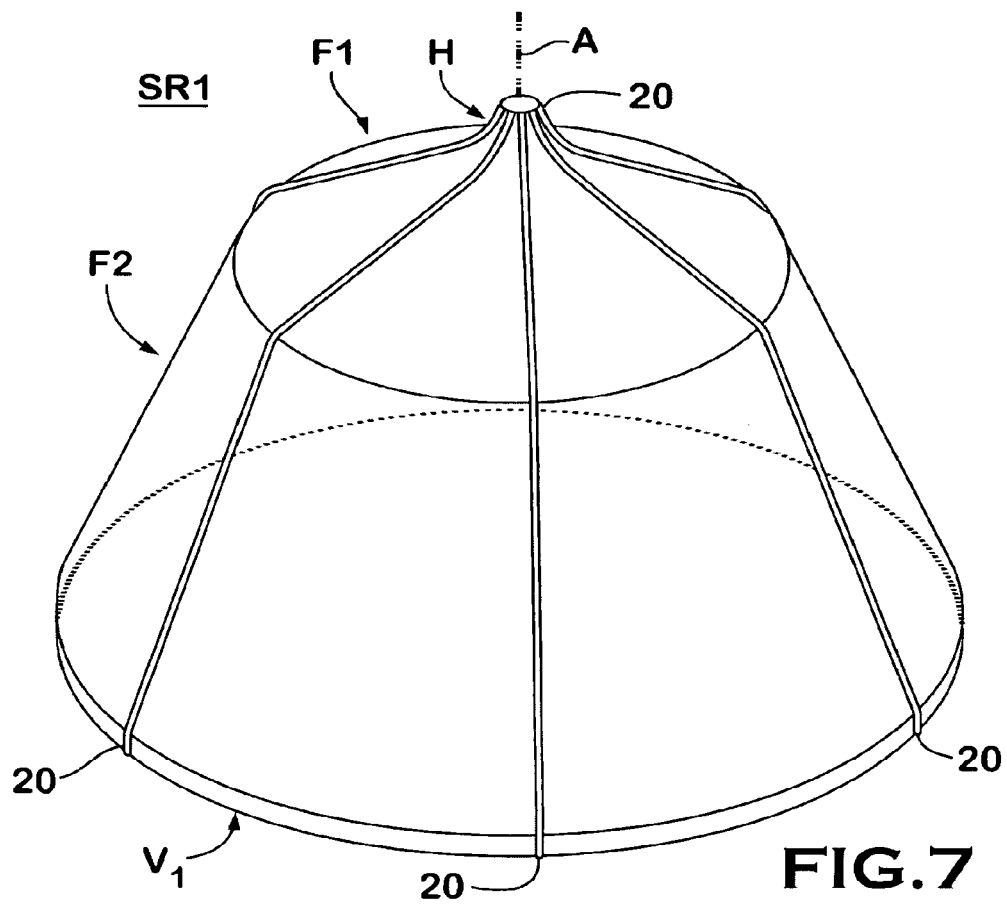
FIG. 7 is a shaded perspective view of a volume generated by the locator member outside of a hub as it rotates or sweeps around longitudinal axis A.
Figure 8:
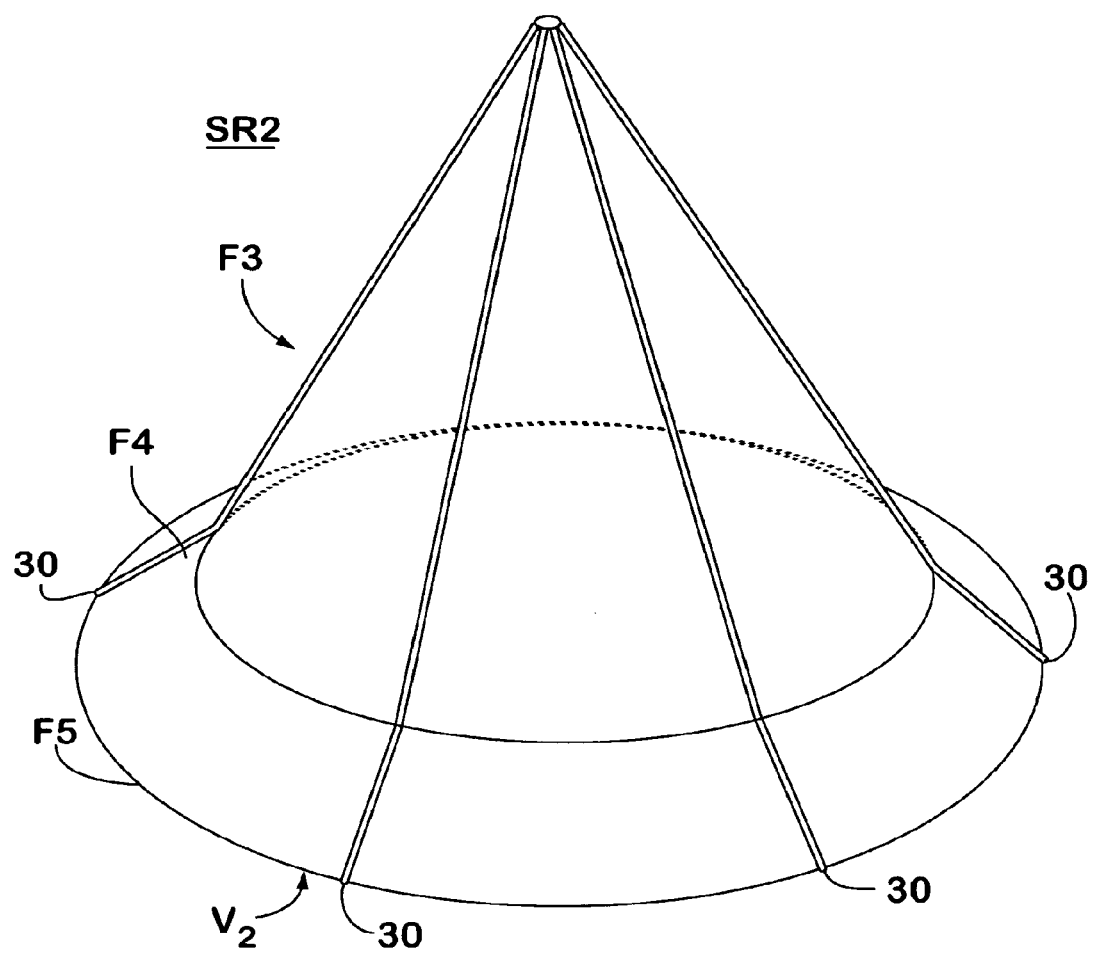
FIG. 8 is a shaded perspective view of a volume generated by the anchor member outside the hub as the anchor member is rotated or sweeps around the longitudinal axis A.

Referring to FIG. 7, the locators 20 are illustrated has being bounded by a first compound surface of revolution SR1 about axis A by rotating one of the locators 20 about axis A for 360 degrees. The first compound surface of revolution SR1 includes a portion of a truncated hyperboloid H, first frustum F1, second frustum F2, and cylindrical surface C1. With reference to FIG. 8, the anchors 30 are illustrated as being bounded by a second compound surface of revolution SR2 about axis A by rotating one of the anchors 30 about axis A for 360 degrees. The second compound surface of revolution SR2 defined by the anchors 30 includes a third, fourth and fifth frustums F3, F4, and F5, respectively.

Figure 9:
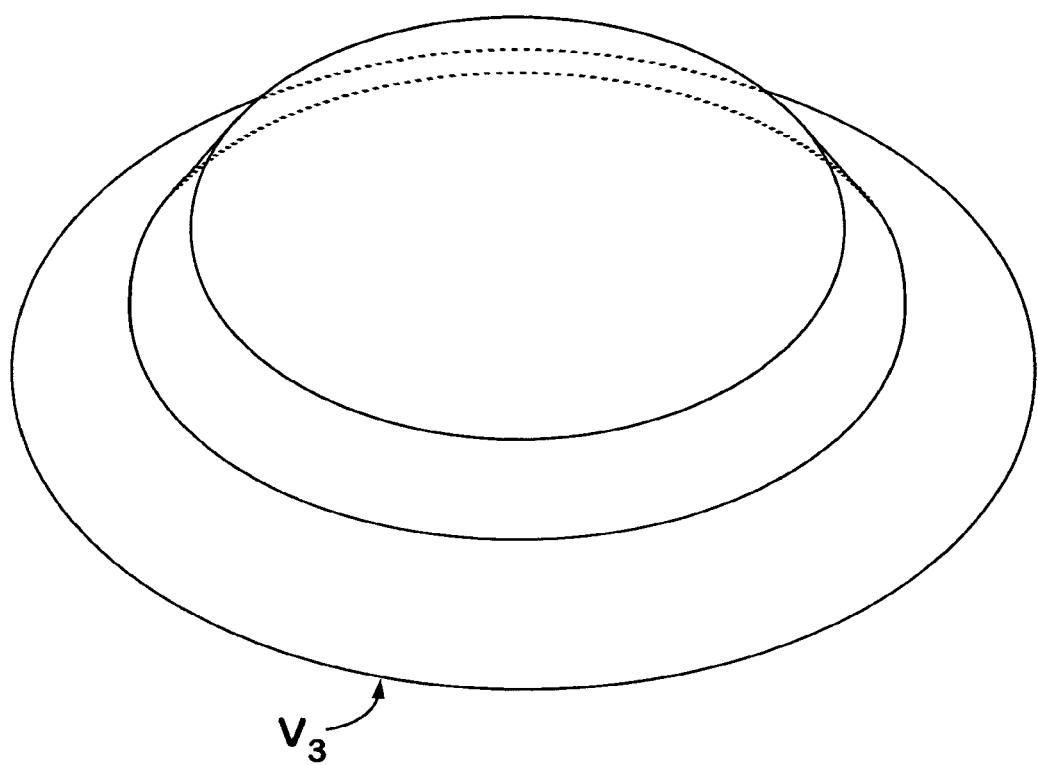
FIG. 9 illustrate the volume of the anchor member visible outside the volume of the locator member.

Several design parameters are believed to allow the preferred embodiments to achieve various advantages over the known filters. The various advantages include, for example, resisting migration of the filter 100 once installed, greater filter volume, and better concentricity with respect to the inner wall of the blood vessel. A number of design parameters may be adjusted to effect performance and fit characteristics of the filter, including, for example, the ratio of the volume $V_1$ defined by the first surface of revolution SR1 to the volume $V_2$ defined by the second surface of revolution SR2, which may be at least 0.92, preferably about 1.0, and most preferably about 0.99. Also, approximately 15% or more of the volume $V_2$ may be surrounded by the volume $V_1$, preferably at least 25% of the volume $V_2$ may be surrounded by the volume $V_1$, and most preferably, about 35% of the volume $V_2$ may be surrounded by volume $V_1$ so that the portion of volume $V_2$ that is not surrounded by volume $V_1$ (i.e., the volume of $V_1$ outside the first volume $V_1$), shown as volume $V_3$ in FIG. 9, is about 0.4 cubic inches. Also, it has been discovered that, in the preferred embodiments, as the cross-sectional area of the hook is increased, the filter 100 tends to resist dislodgement when installed in a simulated blood vessel. Similarly, when the radius of curvature $R_2$ is decreased, while keeping other parameters generally constant, the resistance to dislodgement in a simulated blood vessel is increased.

The material for the filter may be any suitable biocompatible material such as, for example, polymer, memory polymer, memory metal, thermal memory material, metal, metal alloy, or ceramics. Preferably, the material may be Elgiloy, and most preferably Nitinol which is a thermal shape memory alloy.

The use of a shape memory material, such as Nitinol, for the locator and anchor members facilitates collapsing the filter radially inward from its normally expanded (i.e., unconstrained) configuration toward its longitudinal axis into a collapsed configuration for insertion into a body vessel. The properties of Nitinol allow the filter members to withstand enormous deformations (e.g. 8 times as much as stainless steel) without having any effect of the filter ability to recover to the pre-determined shape. This is due to the crystal phase transitions between rigid austenite and softer martensite. This phenomenon enables the implant to be loaded into a very small diameter sheath for delivery, which significantly reduces the trauma and complications to the insertion site.

Transition between the martensitic and austenitic forms of the material can be achieved by increasing or decreasing the material deformation above and below the transition stress level while the material remains above the transition temperature range, specifically $A_f$. This is particularly important in the case of the hooks, as they may be deformed significantly (hence, becoming martensitic) while the filter is challenged by clots. The super-elastic properties will allow the hooks to re-assume their intended shape as soon as the load is released (e.g. the clot breaks down).

The hooks may be retrieved from the Inferior Vena Cava ("IVC") wall during the filter removal when longitudinal force is applied to the hub 10 in the direction of the BF (i.e., towards the hub 10 of the filter). Under this concentrated stress, the hooks will straighten and transition to the martensitic state, thereby becoming super-elastic. Thus the hooks 40 are designed to bend toward a substantially straight configuration when a specific hook migration force is applied and spring back to their original shape once the hook migration force is removed.

Alternatively, a reduction in temperature below the $A_f$ temperature can be applied to the shape memory material to cause a change in the crystalline phase of the material so as to render the material malleable during loading or retrieval of the filter. Various techniques can be used to cause a change in crystalline phase such as, for example, cold saline, low temperature fluid or thermal conductor.

By virtue of the characteristics of thermal shape memory material, the locator and anchor members can be cooled below the martensitic-to-austenitic transition temperature, and then straightened and held in a collapsed, straight form that can pass through a length of fine plastic tubing with an internal diameter of approximately 2 millimeters (mm), e.g., a #8 French catheter. In its high temperature form (as in a mammalian body), the filter 10 recovers to a preformed filtering shape as illustrated by FIG. 1. Alternatively, the locator and/or anchor members may be made of wires of spring metal which can be straightened and compressed within a catheter or tube and will diverge into the filter shape of FIG. 1 when the tube is removed.

The deployed shapes and configurations of the filter members can be set (imprinted with a memory shape) by annealing the members at high temperature (e.g. approximately 500° C.) while holding them in the desired shape. Thereafter, whenever the filter is in the austenitic form (i.e., at a temperature above the martensitic-to-austenitic transition temperature or $A_f$ temperature), the members return to the memory shape. Example methods for setting the high-temperature shape of filters are disclosed in U.S. Pat. No. 4,425,908, the contents of which are hereby incorporated by reference in their entirety.

In the high-temperature form of the shape memory material, the filter has generally coaxial first and second filter baskets or sieves, each filter basket being generally symmetrical about the longitudinal axis of the filter with both filter baskets being concave relative to the filter leading end.

Figure 3:
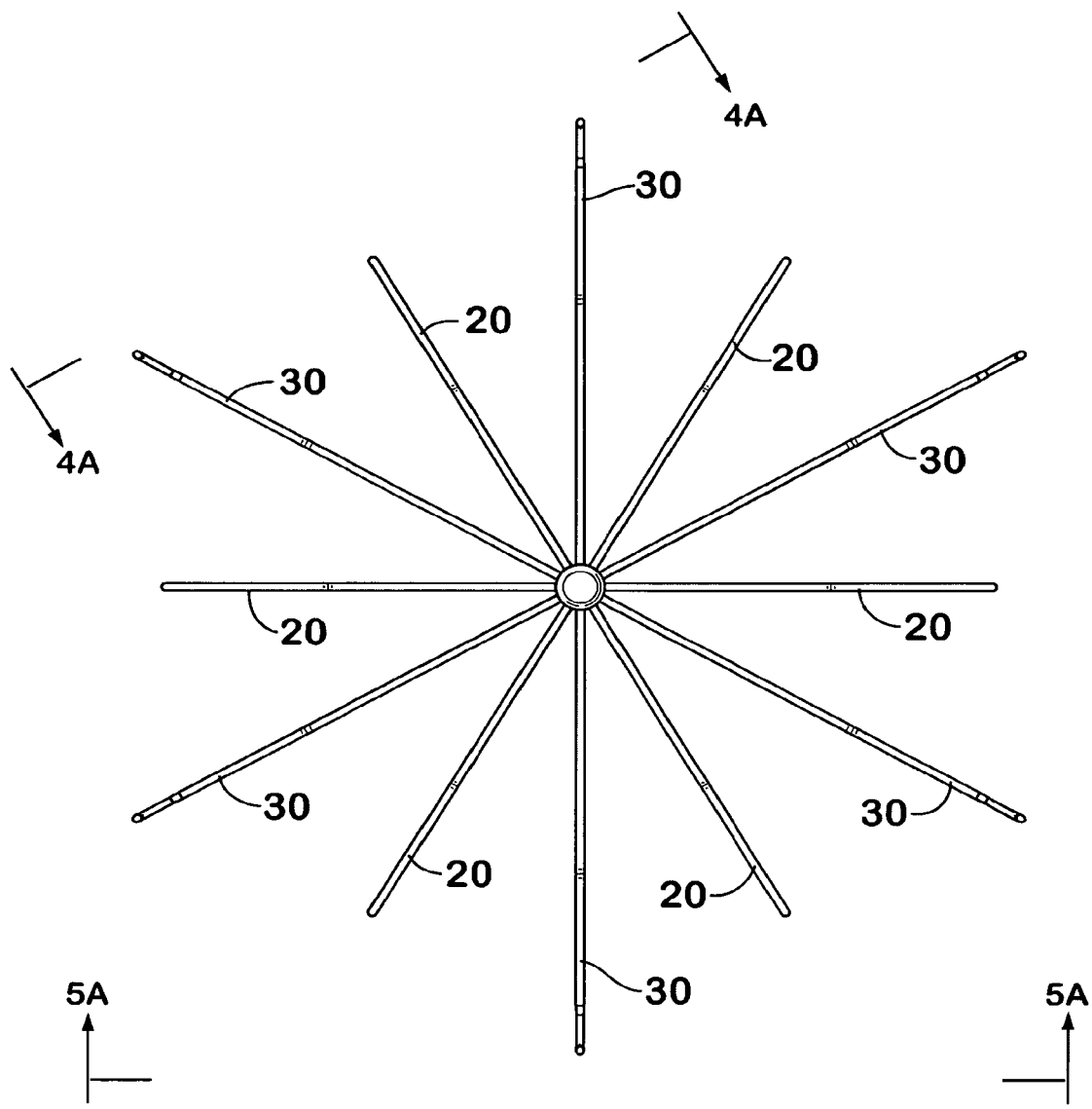
FIG. 3 is a plan view of the filter of FIG. 1 on longitudinal axis A.

The sieve $V_2$ formed by anchor members 30 is the primary filter and can be up to twelve circumferentially spaced anchor members 30. Six anchor members 30 are shown in the embodiment illustrated in the figures. The anchor members may be of equal length, but may be of different length so that the hooks 40 at the ends of the wires will fit within a catheter without becoming interconnected. The anchor members 30, in their expanded configuration illustrated in FIG. 1 (i.e., unconstrained in the high temperature form), are at a slight angle to the vessel wall, preferably within a range of from ten to forty-five degrees, while the hooks 40 penetrate the vessel wall to anchor the filter against movement. The anchor members 30 are radially offset relative to the locator members 20 and may be positioned radially halfway between the locator members 20 and also may be circumferentially spaced by sixty degrees of arc as shown in FIG. 3. The locator members 20 form sieve $V_1$. Thus, the combined filter sieves $V_2$ and $V_1$ can provide a wire positioned radially about the hub 10, such as at every thirty degrees of arc at the maximum divergence of the filter sections. With reference to the direction of blood flow BF shown by the arrow in FIGS. 2 and 4A, in the illustrated embodiment, the filter section $V_2$ forms a frustum toward the hub 10 of the filter 100 while the filter section $V_1$ forms a generally frustum-like concave sieve with its geometric center proximate the terminal end 12 of the hub 10. In the preferred embodiments, the volume $V_1$ of the surface SR1 may be between about 0.3 and about 1.1 cubic inches, preferably about 0.7 cubic inches and the volume $V_2$ of the surface SR2 may be between about 0.3 and about 1.1 cubic inches, preferably about 0.7 cubic inches.

The structure of the hooks 40 is believed to be important in resisting migration of the filter once installed while allowing for removal from the blood vessel after installation. As in the case of hooks formed on the anchor members of known permanent vena cava filters, these hooks 40 penetrate the vessel wall when the filter 100 is expanded to anchor the filter in place and prevent filter migration longitudinally within the vessel in either direction. However, when the hooks 40 are implanted and subsequently covered by the endothelium layer, they and the filter can be withdrawn without risk of significant injury or rupture to the vena cava. Minor injury to the vessel wall due to hook withdrawal such as damage to the endothelial layer or local vena cava wall puncture is acceptable.

To permit safe removal of the filter, the juncture section 40S may be considerably reduced in cross section relative to the thickness $t_2$ or cross section of the anchor member 30 and the remainder of the hook 40. The juncture section 40S can be sized such that it is of sufficient stiffness when the anchor members 30 are expanded to permit the hook 40 to penetrate the vena cava wall. However, when the hook is to be withdrawn from the vessel wall, withdrawal force in the direction of blood flow BF will cause flexure in the juncture section 40S so that the hook tip 40T moves toward a position parallel with the axis A (i.e., the hook straightens). With the hooks so straightened, the filter can be withdrawn without tearing the vessel wall while leaving only small punctures. In an embodiment, the anchor member 30 has a cross-sectional area of about 0.00013 squared inches, and the hook 40, particularly the curved junction section 40S has a cross-sectional area of about 0.000086 squared inches.

With reference to FIG. 6, it will be noted that the entire hook 40 can be formed with a cross section $t_3$ throughout its length that is less than that of the locator 20 members (which have thickness $t_1$) or anchor members 30 (which have thickness $t_2$). As a result, an axial withdrawal force will tend to straighten the hook 40 over its entire length. This elasticity in the hook structure is believed to prevent the hook from tearing the vessel wall during withdrawal.

As previously indicated, while it is possible that the filter could be made from ductile metal alloys such as stainless steel, titanium, or Elgiloy, it is preferable to make it from Nitinol. Nitinol is a low modulus material that allows the locator and anchor members of the device 100 to be designed to have low contact forces and pressures while still achieving sufficient anchoring strength to resist migration of the device. The force required to cause opening of the hooks 40 can be modulated to the total force required to resist filter migration. This is accomplished by changing the cross sectional area or geometry of the hooks, or by material selection, as discussed above.

In addition to temperature sensitivity, when in the high temperature austenitic state, Nitinol is also subject to stress sensitivity that can cause the material to undergo a phase transformation from the austenitic to the martensitic state while the temperature of the material remains above the transition temperature. By reducing the cross sectional area of a portion or all of the hooks 40 relative to that of the anchor members 30 or locator members 20, stress will be concentrated in the areas of reduced cross section when longitudinal force is applied to the hub 10 in the direction of the BF (i.e., towards the hub 10 of the filter) such as to remove the filter. Under this concentrated stress, the reduced cross section portions of the hooks may transition to the martensitic state, thereby becoming elastic so that they straighten. Thus the hooks 40, whether formed of Nitinol, Elgiloy, spring metal or plastic, are designed to bend toward a substantially straight configuration when a specific hook migration force is applied and spring back to their original shape once the hook migration force is removed.

The force or stress that is required to deform the hooks 40 can be correlated to the force applied to each hook of the device when it is fully occluded and the blood pressure in the vessel is allowed to reach 50 millimeters of mercury (mm Hg) in a test stand. The test stand (not shown) can be configured to have a length of tubing (with various internal diameters) to allow a filter to be suitably attached thereto. The tubing is connected to another tubing having a terminal end exposed to ambient atmosphere and marked with gradations to indicate the amount of pressure differential across the filter, which is related to the force being applied to each anchor of the filter 100. This force is approximately at least 70 grams on each anchor of a six-anchor device for at least 50 millimeters Hg pressure differential in a 28 mm vessel. The desired total migration resistance force for the filter is believed to be approximately 420 grams for the embodiment of a vena cava filter for an adult human subject, and more anchor members 30 with hooks 40 can be added to lower maximum migration force for each hook. The load on the filter would be correspondingly smaller in vessels of smaller diameter. Preferably the hooks 40 perform as an anchoring mechanism at a predetermined filter migration resistance force within a range of about 10 mm Hg up to about 150-200 mm Hg. Having maintained its geometry at a predetermined filter migration resistance force within this range, the hook 40 preferably begins to deform in response to a higher force applied in the direction of the hub, i.e., the filter trailing end TE with respect to blood flow, and release at a force substantially less than that which would cause damage to the vessel tissue. It is the ability of the hook to straighten somewhat that allows for safe removal of the preferred embodiment filters from the vessel wall.

After the filter 100 has remained in place within a blood vessel for a period of time in excess of two weeks, the endothelium layer will grow over the hooks 40. However, since these hooks 40, when subjected to a withdrawal force in the direction of the hub (i.e., toward the trailing end TE) become substantially straight sections of wire oriented at a small angle to the vessel wall, the filter can be removed leaving only six pin point lesions in the surface of the endothelium. To accomplish this, a catheter such as, for example, the unit described and shown in U.S. Pat. No. 6,156,055, which is incorporated by reference herein, or similar retrieval unit is inserted over the hub 10 and into engagement with the locator members 20. While the hub 10 is held stationary, the catheter may be moved downwardly, forcing the locator members 20 to fold towards the axis A, and subsequently engaging the anchor members 30 and forcing them downwardly thereby withdrawing the hooks 40 from the endothelium layer. Then the hub 10 may be drawn into the catheter to collapse the entire filter 100 within the catheter. When the filter is formed from shape memory material, cooling fluid (e.g., chilled saline) may be passed through the catheter during these steps to aid in collapsing the filter.

The primary objective of the hooks 40 is to ensure that the filter does not migrate during normal respiratory function or in the event of a massive pulmonary embolism. Normal inferior vena cava (IVC) pressures are believed to be between about 2 mm Hg and about 8 mm Hg. An occluded IVC can potentially pressurize to 35 mmHg below the occlusion. To ensure filter stability, a 50 mm Hg pressure drop across the filter may therefore be chosen as the design criteria for the filter migration resistance force for the removable filter 100. When a removal pressure is applied to the filter that is greater than at least 50 millimeters Hg, the hooks 40 will deform and release from the vessel wall. The pressure required to deform the hooks can be converted to force by the following calculations.

Since 51.76 mm Hg=1.0 pounds per square inch (psi), 50 mm Hg=0.9668 psi

For a 28 mm vena cava:

$$A = \frac{\pi}{4}(28)^2 \text{ mm}^2 = 615.4 \text{ mm}^2 = 0.9539 \text{ inches}^2$$

Migration force is calculated by:

$$P = \frac{F}{A}$$
$$F = P \times A$$
$$0.9668 \text{ psi} \times 0.9539 \text{ inches}^2 = 0.9223 \text{ pounds} = 418.7 \text{ grams}$$

It should be noted that as the vena cava diameter increases so does the force required to resist at least 50 millimeters Hg of pressure.

Depending on the number of filter hooks, the strength of each can be calculated. For a device that has six hooks:

$$\text{Hook Strength} = \frac{\text{Filter Migration Resistance Force}}{\text{Number of Hooks}}$$
$$= \frac{418.7}{6}$$
$$= 69.7 \text{ grams}$$

In other words, each hook must be capable of resisting approximately at least 70 grams of force for the filter 100 to resist at least 50 millimeters Hg pressure gradient in a 28 mm vessel.

To prevent excessive vessel trauma each individual hook needs to be relatively weak. By balancing the number hooks and the individual hook strength, minimal vessel injury can be achieved while still maintaining the at least 50 millimeters Hg pressure gradient criteria, or some other predetermined pressure gradient criteria within a range of from 10 mmHg to 150 mm Hg.

Referring to FIG. 4A, the anchor members 30 may be angled outwardly from the anchor joint or bend AJ1 adjacent to but spaced from the outer end of each anchor member 30. When the anchor members 30 are released from compression in a catheter or other tube into a body vessel, this bend in each anchor member insures that the hooks 40 are, in effect, spring loaded in the tube and that they will not cross as they are deployed from the tube. Since the anchor members 30 angled outwardly from the shoulders 30, the hooks 40 are rapidly deployed outwardly as the insertion tube is withdrawn.

In another embodiment, bio-active agents can be incorporated with the blood filter, such as by way of a coating on parts of the filter, or dissolvable structures on, within or attached to the filter. Bio-active agent may be included as part of the filter in order to treat or prevent other conditions (such as infection or inflammation) associated with the filter, or to treat other conditions unrelated to the filter itself. More specifically, bio-active agents may include, but are not limited to: pharmaceutical agents, such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), and trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (e.g., breveldin); anti-inflammatory agents, such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents, such as vascular endothelial growth factor (VEGF), fibroblast growth factor (FGF); angiotensin receptor blockers; nitric oxide donors; anti-sense oligionucleotides and combinations thereof; cell cycle inhibitors, such as mTOR inhibitors, and growth factor receptor signal transduction kinase inhibitors; retenoids; cyclin/CDK inhibitors; HMG co-enzyme reductase inhibitors (statins); and protease inhibitors.

A filter delivery unit (not shown) such as, for example, the unit described in U.S. Pat. No. 6,258,026, which is incorporated by reference herein, is adapted to deliver the filter 100 through a catheter or delivery tube to a generally centered position within a blood vessel, as described in further detail in the above mentioned patent. Preferably, the delivery system may be the delivery system shown and described in U.S. Provisional Patent Application No. 60/706,596, entitled "Embolus Blood Clot Filter and Delivery System," filed on Aug. 9, 2005, or the delivery system shown and described in a patent application that claims priority to the antecedent provisional patent application, PCT Patent Application No. PCT/US2006/017890 entitled "Embolus Blood Clot Filter and Delivery System" filed on May 9, 2006; and both applications are hereby incorporated by reference in their entirety into this application.

In an embodiment, a radio-opaque material can be incorporated in a portion of the filter, preferably the hub 10 of the filter. As used herein, a radio-opaque material is any material that is identifiable to machine or human readable radiographic equipment while the material is inside a mammal body, such as, by way of example but not by way of limitation, gold, tungsten, platinum, barium sulfate, or tantalum. The use of a radio-opaque material in the filter permits the clinician to locate the filter within a blood vessel of the subject using radiographic equipment. Radio-opaque material may be in the form of an additional structure added to the hub, such as a cap, sleeve, shim, wire or braze included around or in the hub assembly. Alternatively, the hub itself may be formed of a radio-opaque alloy.

Figure 10:
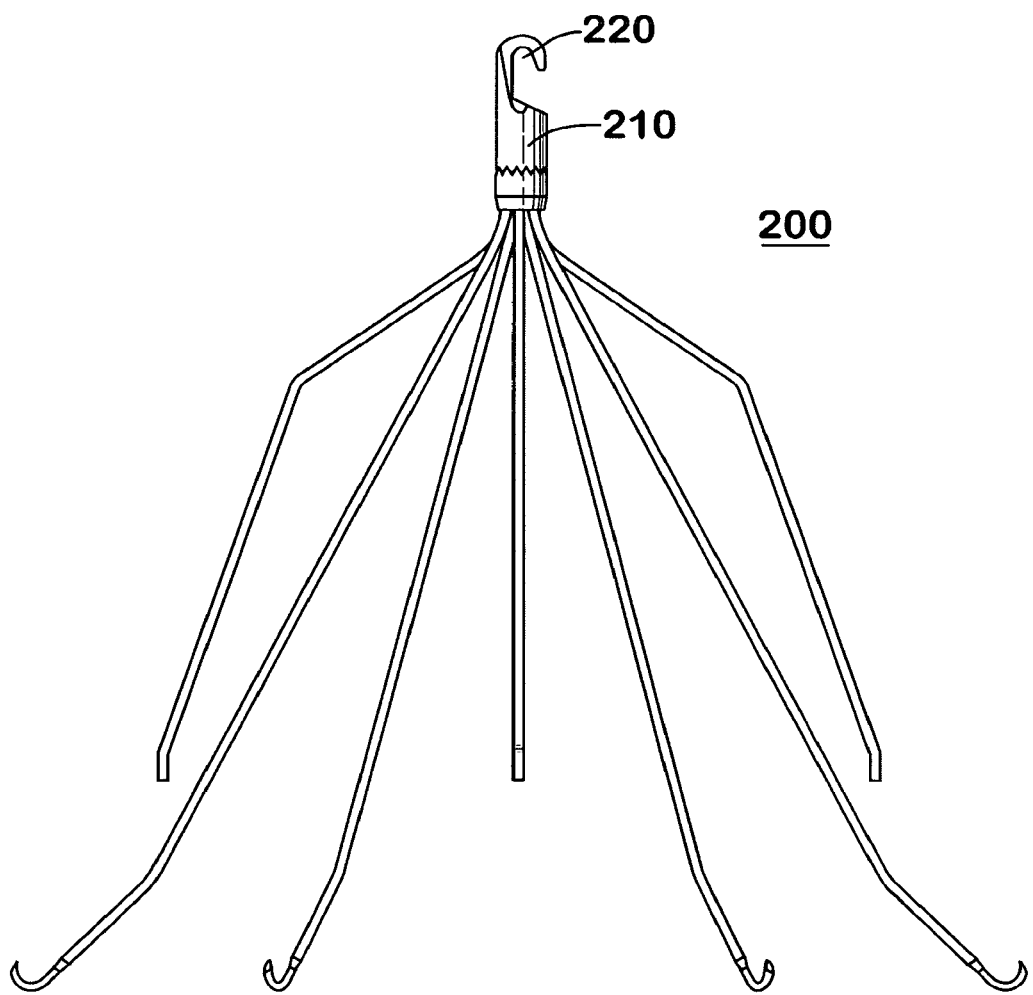
FIGS. 10-14 illustrate yet another preferred embodiment having a retrieving hook portion.
Figure 11:
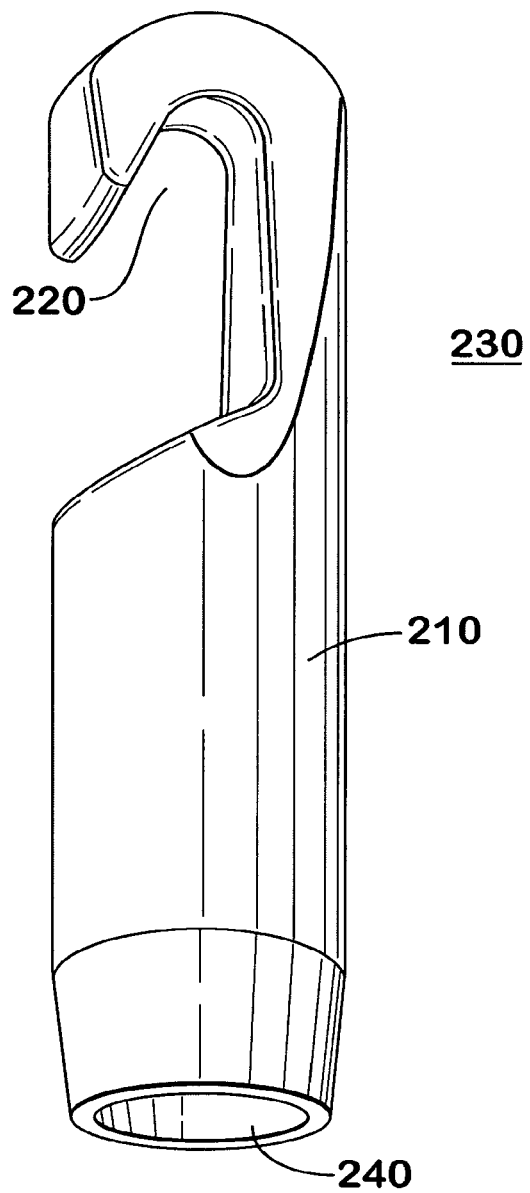
Figure 12:
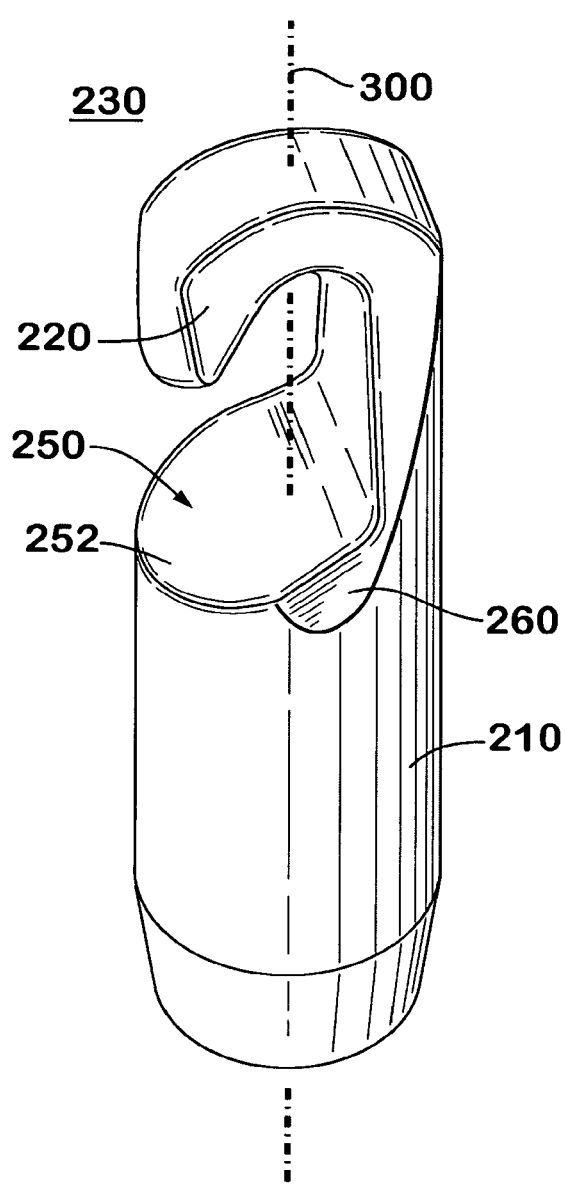
Figure 13:
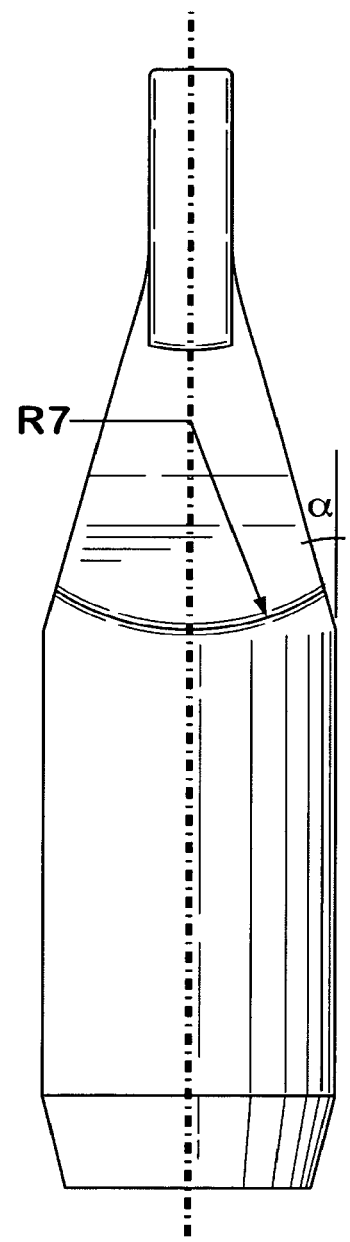
Figure 14:
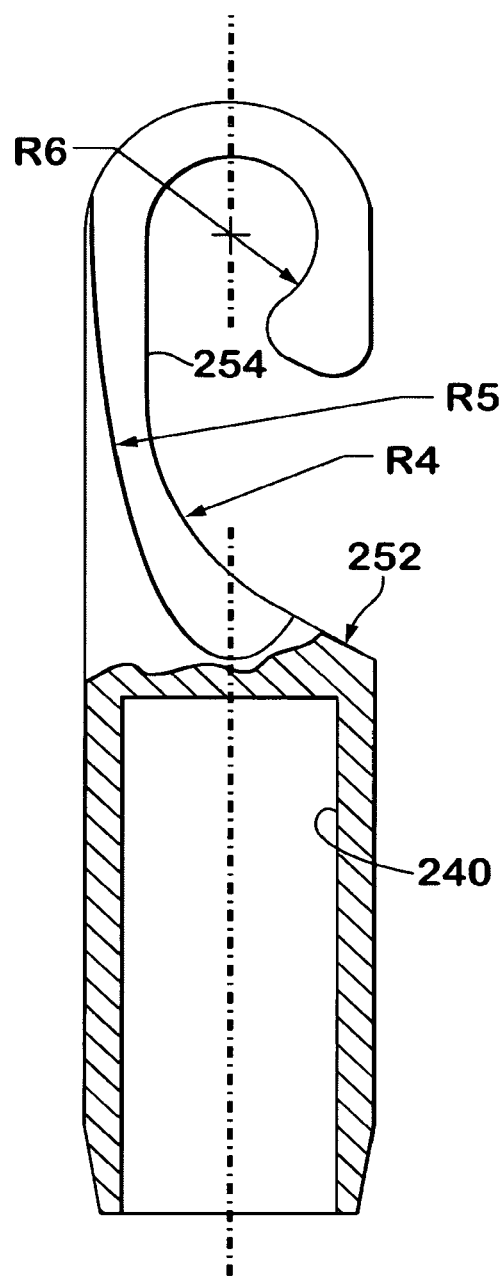

Instead of a hub 10, as in the above described embodiments, a retrieving hook can be provided as part of filter device 200, as in the embodiment shown in FIG. 10. The filter device 200 includes a hub 210 with a retrieving hook 220. The hook 220 is configured for use by a snaring device to retrieve the filter 200 from a subject. Referring to FIGS. 11 and 12, the retrieving hook 220 can be formed as a monolithic member 230 with the hub 210 or as a separate member joined to the hub 210 by a suitable technique, such as, for example, EDM, laser welding, plasma welding, welding brazing, welding, soldering, or bonding. In a preferred embodiment, the member 230 can be a machined billet member with a blind bore 240 formed through a portion of the hub 210. The hook portion 220 includes ramped surfaces 250 and 260 that are believed to be advantageous in allowing the filter 200 to be retrieved without binding at the catheter opening due to an offset entry position of the filter 200. In other words, there may be circumstances during removal procedures where the axis 300 of the member 230 is not generally parallel or aligned with a longitudinal axis of the catheter retrieving device. In such cases, the greater the retention force, it is believed that the greater the likelihood of the hook being snagged on the catheter inlet opening thereby complicating the filter retrieval process. By virtue of the ramps 250 and 260, it is believed that binding or snagging is substantially reduced. In particular, as shown in FIGS. 13 and 14, the ramp 250 includes a radius of curvature R4 coupled to flat portions 252 and 254. The flat portion 254 can be coupled to a hook portion 256 which has a radiused surface R6. As shown in FIG. 13, the flat portion 252 is coupled to another radiused portion R7. It should be noted that the drawings provided herein are to scale relative to every part illustrated in each drawing.

A range of values may be used for the aforementioned dimensional parameters in order to provide a retrieval hook 230 that is capable of retaining portions of the locator and anchor members 20 and 30 within blind hole 240. For example, a smaller filter may have smaller dimensions so that the retrieval hook 230 does not present undue blockage in the vein, than a filter intended to be placed in a large vein or vessels, such as an adult vena cava or other vessel. Further, the retrieval hook 230 may be made from or include a radio-opaque material to allow a clinician to locate the hook within a subject using radiographic equipment, such as to aid in engaging the hook with a retrieval mechanism.

While the present invention has been disclosed with reference to certain preferred embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

What is claimed is:

1. A blood vessel filter, comprising:
a hub disposed along a longitudinal axis;
a plurality of locator members projecting from the hub, a proximal end of each of the locator members attached to the hub, the locator members bounded by a first compound surface of revolution about the longitudinal axis, the first compound surface of revolution including a first frustum distal of the hub having a first volume, and a second frustum distal of the first frustum having a second volume greater than the first volume;
and
a plurality of anchor members projecting from the hub, a proximal end of each of the anchor members attached to the hub, the anchor members bounded by a second compound surface of revolution about the longitudinal axis, the second compound surface of revolution including a third frustum and a fourth frustum distal of the third frustum,
wherein
one of the plurality of locator members has a proximal segment, a first segment, a second segment that extends along a second angle of about 20 degrees with respect to the longitudinal axis;
and
a tip segment that extends along a third angle of less than about 1 degree with respect to the longitudinal axis.

2. The blood vessel filter according to claim 1, wherein the first surface of revolution further includes a cylinder distal of the second frustum.

3. The blood vessel filter according to claim 2, wherein the ratio of a volume defined by the first surface of revolution to a volume defined by the second surface of revolution is in the range from 0.92 to about 1.0.

4. The blood vessel filter according to claim 3, wherein about 15% or more of the volume defined by the second surface of revolution is surrounded by the volume defined by the first surface of revolution.

5. The blood vessel filter according to claim 4, wherein about 25% or more of the volume defined by the second surface of revolution is surrounded by the volume defined by the first surface of revolution.

6. The blood vessel filter according to claim 5, wherein about 35% or more of the volume defined by the second surface of revolution is surrounded by the volume defined by the first surface of revolution.

7. The blood vessel filter according to claim 6, wherein: each of the anchor members includes a hook spaced a first radial distance from the longitudinal axis; and each of the locator members includes a tip segment spaced a second radial distance from the longitudinal axis, wherein the second radial distance is less than the first radial distance.

8. The blood vessel filter according to claim 7, wherein each of the locator members has at least four segments including the tip segment, each disposed on respective distinct axes, the four segments comprising: a proximal segment proximate the hub; a first segment extending from the proximal segment along a first angle with respect to the longitudinal axis; a second segment extending from the first segment along a second angle with respect to the longitudinal axis less than the first angle; and the tip segment extending from the second segment along a third angle with respect to the longitudinal axis less than the second angle.

9. The blood vessel filter according to claim 8, wherein the first and second segments are linear.

10. A blood vessel filter, comprising:
a hub disposed along a longitudinal axis; a plurality of anchor members projecting from the hub, each anchor member including a hook configured to penetrate a blood vessel wall, the hook spaced a first radial distance from the longitudinal axis;
and
a plurality of locator members projecting from the hub, each locator member including a tip segment spaced a second radial distance from the longitudinal axis less than the first radial distance, each locator member including a first linear segment defining a first angle with respect to the longitudinal axis and a second linear segment extending from the first linear segment, the second linear segment defining a second angle with respect to the longitudinal axis different from the first angle, and a linear tip segment extending from the second linear segment,
wherein
one of the plurality of locator members has a proximal segment, the first linear segment, the second linear segment that extends along the second angle of about 20 degrees with respect to the longitudinal axis; and
the linear tip segment that extends along a third angle of less than about 1 degree with respect to the longitudinal axis.

11. The blood vessel filter according to claim 10, wherein the second angle is less than the first angle.

12. The blood vessel filter according to claim 11, wherein each locator member further comprises a linear tip segment extending from the second linear segment, the linear tip segment parallel to the longitudinal axis.

13. The blood vessel filter according to claim 12, wherein the at least one anchor member comprises a first anchor segment extending away from the longitudinal axis, the first anchor segment defining a fourth angle with respect to the longitudinal axis, and a second anchor segment extending from the first anchor segment, the second anchor segment defining a fifth angle with respect to the longitudinal axis greater than the fourth angle.

14. The filter according to claim 13, wherein the hook comprises a curved configuration in an operative condition and a generally linear configuration in a constrained condition.

15. The filter according to claim 14, further comprising a bio-active agent coupled to the filter and a radiopaque material disposed proximate the hub.

* * * * *